(12) United States Patent
Anderson et al.

(10) Patent No.: US 6,624,159 B2
(45) Date of Patent: Sep. 23, 2003

(54) HETEROCYCLE CARBOXAMIDES AS ANTIVIRAL AGENTS

(75) Inventors: David John Anderson, Kalamazoo, MI (US); Gordon L. Bundy, Kalamazoo, MI (US); Fred L. Ciske, Lawton, MI (US); David R. Graber, Kalamazoo, MI (US); Michael J. Genin, Paw Paw, MI (US); Thomas M. Judge, Otsego, MI (US); Malcolm Wilson Moon, Kalamazoo, MI (US); Mark E. Schnute, Kalamazoo, MI (US); Joseph Walter Strohbach, Mendon, MI (US); Suvit Thaisrivongs, Kalamazoo, MI (US); Atli Thorarensen, Portage, MI (US); Steven Ronald Turner, Kalamazoo, MI (US); Valerie A. Vaillancourt, Kalamazoo, MI (US); Allison J. Wolf, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/887,578

(22) Filed: Jun. 22, 2001

(65) Prior Publication Data

US 2002/0025959 A1 Feb. 28, 2002

Related U.S. Application Data

(60) Provisional application No. 60/217,559, filed on Jul. 12, 2000, and provisional application No. 60/272,143, filed on Feb. 28, 2001.

(51) Int. Cl.⁷ .................... C07D 471/06; C07D 471/16; A61K 31/535
(52) U.S. Cl. ................. 514/224.5; 514/220; 514/220.8; 514/229.2; 514/230.2; 514/233.2; 514/243; 514/248; 514/250; 514/267; 514/292; 514/294; 540/496; 540/547; 544/9; 544/32; 544/66; 544/89; 544/101; 544/111; 544/115; 544/126; 544/183; 544/234; 544/252; 544/344; 544/346; 546/84; 546/94

(58) Field of Search ................. 540/496, 547; 544/9, 32, 66, 89, 101, 111, 112, 115, 126, 183, 234, 252, 344, 346; 546/84, 94; 514/220, 220.8, 224.5, 229.2, 230.2, 233.2, 243, 248, 250, 267, 292, 294

(56) References Cited

U.S. PATENT DOCUMENTS

| 5,792,774 A | 8/1998 | Haughan et al. ............ 514/294 |
| 6,340,680 B1 * | 1/2002 | Turner et al. ............ 514/230.2 |

FOREIGN PATENT DOCUMENTS

| WO | WO00/40561 | 7/2000 | ......... C07D/215/16 |
| WO | WO01/25239 | 4/2001 | ......... C07D/491/06 |

OTHER PUBLICATIONS

Douglas, Jr. Introduction to Viral Diseases, Cecil Textbook of Medicine, 20th Edition, vol. 2, pp. 1739–1747, 1996.*
Boppana et al., PubMed Abstract (J. Infect. Dis. 171(1): 182–5), Jan. 1995*
Raftery et al., PubMed Abstract (J. Exp. Med. 190(8): 1103–14) Oct. 1999.*
Wood, Viral Infections in neutropenia—current problems and chemotherapeutic control, J. Antimicrobial Chemotherapy, 41 (Suppl. D) pp. 81–93, 1998.*

* cited by examiner

Primary Examiner—Deepak Rao
(74) Attorney, Agent, or Firm—Lucy X. Yang

(57) ABSTRACT

The present invention provides a compound of formula I

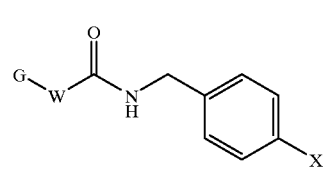

which is useful as antiviral agents, in particular, as agents against viruses of the herpes family.

46 Claims, No Drawings

HETEROCYCLE CARBOXAMIDES AS ANTIVIRAL AGENTS

CROSS REFERENCE TO RELATED APPLICATIONS

This application claims the benefit of the following provisional applications: U.S. Ser. No: 60/217,559, filed Jul. 12, 2000, and U.S. Ser. No: 60/272,143, filed Feb. 28, 2001, under 35 USC 119(e)(i).

BACKGROUND OF THE INVENTION

1. Field of the Invention

The present invention provides heterocycle carboxamide derivatives. These compounds are useful as antiviral agents, in particular, as agents against viruses of the herpes family.

2. Technology Description

The herpesviruses comprise a large family of double stranded DNA viruses. They are also a source of the most common viral illnesses in man. Eight of the herpes viruses, herpes simplex virus types 1 and 2 (HSV-1 and HSV-2), varicella zoster virus (VZV), human cytomegalovirus (HCMV), Epstein-Barr virus (EBV), and human herpes viruses 6, 7, and 8 (HHV-6, HHV-7, and HHV-8), have been shown to infect humans.

HSV-1 and HSV-2 cause herpetic lesions on the lips and genitals, respectively. They also occasionally cause infections of the eye and encephalitis. HCMV causes birth defects in infants and a variety of diseases in immunocompromised patients such as retinitis, pneumonia, and gastrointestinal disease. VZV is the causative agent of chicken pox and shingles. EBV causes infectious mononucleosis. It can also cause lymphomas in immunocompromised patients and has been associated with Burkitt's lymphoma, nasopharyngeal carcinoma, and Hodgkins disease. HHV-6 is the causative agent of roseola and may be associated with multiple sclerosis and chronic fatigue syndrome. HHV-7 disease association is unclear, but it may be involved in some cases of roseola. HHV-8 has been associated with Karposi's sarcoma, body cavity based lymphomas, and multiple myeloma.

U.S. Pat. No. 5,792,774 discloses specific quinoline derivatives that are alleged to have therapeutic utility via inhibition of Phosphodiesterase IV esterase and/or Tumor Necrosis factor activity.

Despite the above teachings, there still exists a need in the art for novel compounds that demonstrate desirable antiviral activity.

BRIEF SUMMARY OF THE INVENTION

In accordance with the present invention, novel compounds which demonstrate antiviral activity are provided. More specifically, the compounds are specific heterocycle carboxamide derivatives which are useful as antiviral agents, particularly against herpes viruses.

Even more specifically, the present invention provides a compound of formula I,

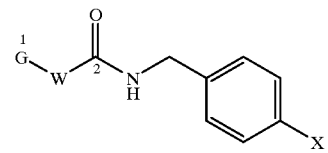

wherein,

X is Cl, Br, F, CN or $NO_2$;

G is
  (a) $C_{1-4}$alkyl which is fully saturated or partially unsaturated and is substituted by hydroxy, or
  (b) $C_{1-4}$alkyl substituted by $NR^1R^2$ or 4-tetrahydropyran;

$R^1$ is $C_{2-7}$alkyl substituted by hydroxy, $C_{1-4}$alkoxy, aryl, or heteroaryl;

$R^2$ is hydrogen or $C_{1-7}$alkyl;

or $R^1$ and $R^2$ together with the nitrogen to which they are attached form (a) a morpholine which may be optionally substituted by aryl or $C_{1-7}$alkyl; or (b) a pyrrolidine ring substituted by hydroxy;

W is a heterocycle of formula W1, W2, W3, W4, W5, W6, W7 or W8

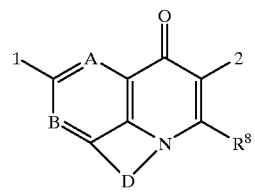

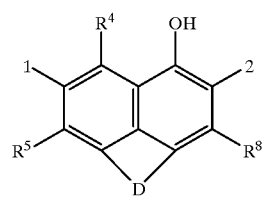

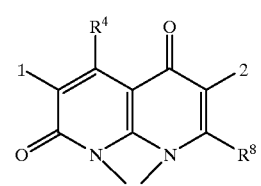

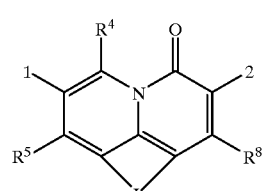

-continued

W5

[chemical structure]

W6

[chemical structure]

W7

[chemical structure]

W8

[chemical structure]

A is $CR^4$ or nitrogen;
B is $CR^5$ or nitrogen;
D is
  (a) —$(CR^{13}R^{14})_a$—, where a is 2 or 3,
  (b) —$(CR^{15}R^{16})_4$—,
  (c) —Y—$CR^{13}R^{14}$—$CR^{13}R^{14}$—,
  (d) —$CR^{13}R^{14}$—Y—$CR^{13}R^{14}$—,
  (e) —Y—$CR^{13}R^{14}$—Y—,
  (f) —$CR^{13}R^{14}$—$CR^{13}R^{14}$—Y—,
  (g) —Y—$(CR^{15}R^{16})_n$—,
  (h) —Y—$CR^{15}$=$CR^{15}$—,
  (i) —Y—$CR^{15}$=N—,
  (j) —$CR^{15}$=$CR^{15}$—Y—,
  (k) —N=$CR^{15}$—Y—,
  (l) —$(CR^{15}R^{16})_b$—N=$CR^{15}$—, where b is 0 or 1
  (m) —$CR^{15}$=N—$(CR^{15}R^{16})_b$—, where b is 0 or 1
  (n) —N=N—,
  (o) —N=$CR^{15}$—$(CR^{15}R^{16})_b$—, where b is 0 or 1
  (p) —$CR^{15}$=$CR^{15}$—,
  (q) —N=N—Y—,
  (r) —Y—N=N—,
  (s) —Y—N=$CR^{15}$—, or
  (t) —$CR^5R^{16}$—Y—$CR^{15}R^{16}$—$CR^{15}R^{16}$—;

E is $CR^8$ or nitrogen;
J is $CR^{15}$ or nitrogen;
K is
  (a) —$(CR^{15}R^{16})_a$—, where a is 2 or 3, or
  (b) —$CR^{15}$=$CR^{15}$—,
L is
  (a) —$(CR^{15}R^{16})_a$—, where a is 2 or 3, or
  (b) —Y—$(CR^{15}R^{16})$—$(CR^{15}R^{16})$—;
Y is oxygen, $S(O)_m$, or $NR^7$;
with the provisos that:
  when W is of formula W1; G is $C_{1-4}$alkyl which is fully saturated and is substituted by hydroxy or morpholinyl, in which morpholinyl is attached through nitrogen; A is $CR^4$; B is $CR^5$; and $R^8$ is hydrogen then at least one of $R^{13}$, $R^{14}$, or $R^7$ is not hydrogen or $C_{1-7}$alkyl;
  when W is of formula W1, A is $CR^4$, B is $CR^5$, D is —Y—$CR^{13}R^{14}$—$CR^{13}R^{14}$—, and $R^8$ is hydrogen then Y is not oxygen;
  when W is of formula W1, A is $CR^4$, and B is $CR^5$ then D is not —$CR^{15}$=$CR^{15}$—;
$R^4$ is H, halogen, or $C_{1-4}$alkyl optionally substituted by one to three halogens;
$R^5$ is
  (a) H,
  (b) halo,
  (c) $OR^{12}$,
  (d) $SR^{12}$,
  (e) $C_{1-7}$alkyl which may be partially unsaturated and optionally substituted by one or more substituents selected from $OR^{12}$, $SR^{12}$, $NR^{10}R^{11}$, or halo,
  (f) $C_{3-8}$cycloalkyl which may be partially unsaturated and is optionally substituted by one or more substituents selected from halogen, $OR^{12}$, $SR^{12}$, or $NR^{10}R^{11}$,
  (g) (C=O)$R^9$,
  (h) $S(O)_mR^9$,
  (i) (C=O)$OR^2$,
  (j) $NHSO_2R^9$,
  (k) nitro, or
  (l) cyano;
$R^7$ is
  (a) H,
  (b) $C_{1-7}$alkyl which may be partially unsaturated and optionally substituted by one or more substituents selected from $OR^{12}$, $SR^{12}$, $NR^{10}R^{11}$, or halo,
  (c) $C_{3-8}$cycloalkyl which may be partially unsaturated and is optionally substituted by one or more substituents selected from halogen, $OR^{12}$, $SR^{12}$, or $NR^{10}R^{11}$,
  (d) aryl,
  (e) het,
  (f) (C=O)$R^9$, or
  (g) $S(O)_mR^9$;
$R^8$ is
  (a) H,
  (b) $C_{1-7}$alkyl which may be partially unsaturated and optionally substituted by one or more substituents selected from $OR^{12}$, $SR^{12}$, $NR^{10}R^{11}$, or halo,
  (c) $OR^{12}$, or
  (d) $SR^{12}$;
$R^9$ is
  (a) $C_{1-7}$alkyl optionally substituted by $OR^{12}$ or $NR^2R^2$,
  (b) $C_{3-8}$cycloalkyl optionally substituted by $OR^{12}$ or $NR^2R^2$,
  (c) $NR^{10}R^{11}$,
  (d) aryl, or (e) het, wherein said het is bound through a carbon atom;

$R^{10}$ and $R^{11}$ are independently
(a) H,
(b) aryl,
(c) $C_{1-7}$alkyl which may be partially unsaturated and is optionally substituted by one or more substituents selected from $CONR^2R^2$, $CO_2R^2$, het, aryl, cyano, or halo,
(d) $C_{2-7}$alkyl which may be partially unsaturated and is substituted by one or more substituents selected from $NR^2R^2$, $OR^2$, or $SR^2$,
(e) $C_{3-8}$cycloalkyl which may be partially unsaturated and is optionally substituted by one or more substituents selected from halogen, $OR^2$, $SR^2$, or $NR^2R^2$, or
(f) $R^{10}$ and $R^{11}$ together with the nitrogen to which they are attached form a het;

$R^{12}$ is
(a) H,
(b) aryl,
(c) het
(d) $C_{1-7}$alkyl optionally substituted by aryl, or halogen,
(e) $C_{2-7}$alkyl substituted by $OR^2$, $SR^2$, or $NR^2R^2$, or
(f) $C_{3-8}$cycloalkyl which may be partially unsaturated and is optionally substituted by one or more substituents selected from halogen, $OR^2$, $SR^2$, or $NR^2R^2$;

$R^{13}$, $R^{14}$, $R^{15}$, and $R^{16}$ are independently
(a) H
(b) $C_{1-7}$alkyl which may be partially unsaturated and optionally substituted by one or more $OR^{12}$, $SR^{12}$, $NR^{10}R^{11}$, or halo groups,
(c) $C_{3-8}$cycloalkyl which may be partially unsaturated and is optionally substituted by one or more substituents selected from halogen, $OR^{12}$, $SR^{12}$, or $NR^{10}R^{11}$,
(d) aryl,
(e) het, wherein said het is bound through a carbon atom,
(f) $OR^{12}$,
(g) $SR^{12}$,
(h) $NR^{10}R^{11}$;
(i) (C=O)$OR^2$, or
(j) $R^{13}$ and $R^{14}$ or $R^{15}$ and $R^{16}$ together with the carbon to which they are attached form (C=O);

each m is independently 0, 1 or 2;
each n is independently 1 or 3;
aryl is a phenyl radical or an ortho-fused bicyclic carbocyclic radical wherein at least one ring is aromatic, and aryl may be optionally substituted with one or more substituents selected from halo, OH, cyano, $NR^2R^2$, $CO_2R^2$, $CF_3$, $C_{1-6}$alkoxy, and $C_{1-6}$alkyl which maybe further substituted by one to three $SR^2$, $NR^2R^2$, $OR^2$, or $CO_2R^2$ groups;
het is a four- (4), five- (5), six- (6), or seven- (7) membered saturated or unsaturated heterocyclic ring having 1, 2, or 3 heteroatoms selected from oxygen, sulfur, or nitrogen, which is optionally fused to a benzene ring, or any bicyclic heterocycle group, and het may be optionally substituted with one or more substituents selected from halo, OH, cyano, phenyl, $CO_2R^2$, $CF_3$, $C_{1-6}$alkoxy, oxo, oxime, and $C_{1-6}$ alkyl which may be further substituted by one to three $SR^2$, $NR^2R^2$, $OR^2$, or $CO_2R^2$ groups;

halo or halogen is F, Cl, Br, I;
1 represents the point of attachment between W and G;
2 represents the point of attachment between W and the carbonyl group of Formula (I);
and pharmaceutically acceptable salts thereof.

In particularly preferred embodiments, X is Cl and G is 4-morpholinylmethyl.

Another embodiment of the present invention provides a pharmaceutical composition comprising a compound of formula (I) as defined above, or a pharmaceutically acceptable salt thereof, and a pharmaceutically acceptable carrier. In preferred embodiments, the composition preferably comprises a therapeutically effective amount of the compound or salt.

Still another embodiment of the present invention provides a method for treating a disease or condition in a mammal caused by a viral infection, particularly a herpes viral infection, comprising administering to the mammal a therapeutically effective amount of a compound of formula (I) or a pharmaceutically acceptable salt thereof.

A further embodiment of the present invention comprises the use of a compound of formula (I) or a pharmaceutically acceptable salt thereof to prepare a medicament for treating or preventing diseases or disorders caused by a viral infection, and particularly a herpes viral infection.

A final embodiment of the present invention comprises a method for inhibiting a viral DNA polymerase, comprising contacting (in vitro or in vivo) the polymerase with an effective inhibitory amount of a compound of formula (I) or a pharmaceutically acceptable salt thereof.

An object of the present invention is to provide novel compounds having biological activity.

A further object of the present invention is to provide novel pharmaceutical compositions.

Still another object of the present invention is to provide a method for treating a disease or condition in a mammal caused by a viral infection, particularly a herpes virus infection.

Another object of the present invention is to provide a method for inhibiting a viral DNA polymerase.

These, and other objects, will readily be apparent to those skilled in the art as reference is made to the detailed description of the preferred embodiment.

DETAILED DESCRIPTION OF THE PREFERRED EMBODIMENT

In describing the preferred embodiment, certain terminology will be utilized for the sake of clarity. Such terminology is intended to encompass the recited embodiment, as well as all technical equivalents which operate in a similar manner for a similar purpose to achieve a similar result.

1. Terminology Definitions

The following definitions are used, unless otherwise described: halo is fluoro, chloro, bromo, or iodo. Alkyl denotes both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more (e.g., 1, 2, 3, or 4) double or triple bonds in the chain.

Aryl denotes a phenyl radical or an ortho-fused bicyclic carbocyclic radical wherein at least one ring is aromatic. Het is a four- (4), five- (5), six- (6), or seven- (7) membered saturated or unsaturated ring containing 1, 2 or 3 heteroatoms selected from the group consisting of non-peroxide oxygen, sulfur, and nitrogen, which is optionally fused to a benzene ring, or any bicyclic heterocyclic group. Het includes "heteroaryl", which encompasses a radical attached via a ring carbon of a monocyclic aromatic ring containing five or six ring atoms consisting of carbon and 1, 2, 3, or 4 heteroatoms each selected from the group consisting of non-peroxide oxygen, sulfur, and N(X) wherein X is absent or is H, O, $C_{1-4}$alkyl, phenyl or benzyl.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art.

The carbon atom content of various hydrocarbon-containing moieties is indicated by a prefix designating a lower and upper number of carbon atoms in the moiety, i.e., the prefix $C_{i-j}$ indicates a moiety of the integer "i" to the integer "j" carbon atoms, inclusive. Thus, for example, $C_{1-7}$alkyl refers to alkyl of one to seven carbon atoms, inclusive.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents. The compounds of the invention include compounds of formula (I) having any combination of the values, specific values, more specific values, and preferred values described herein.

Mammal denotes human and animals, specifically including food animals and companion animals.

2. The Invention

The present invention comprises compounds of formula (I) as defined above, and their pharmaceutically acceptable salts.

For the compounds of formula (I), alkyl can be methyl, ethyl, propyl, isopropyl, butyl, iso-butyl, sec-butyl, pentyl, 3-pentyl, hexyl, heptyl, etc.; $C_{3-8}$cycloalkyl can be cyclopropyl, cyclobutyl, cyclopentyl, cyclohexyl, cycloheptyl, or cyclooctyl; alkoxy can be methoxy, ethoxy, propoxy, isopropoxy, butoxy, iso-butoxy, sec-butoxy, pentoxy, 3-pentoxy, hexyloxy, 1-methylhexyloxy, or heptyloxy; het can be azetidinyl, 3,3-dihydroxy-1-azetinyl, pyrrolidino, piperidino, morpholino, thiomorpholino, or heteroaryl; and heteroaryl can be furyl, imidazolyl, triazolyl, triazinyl, oxazolyl, isoxazolyl, thiazolyl, isothiazolyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

When alkyl is partially unsaturated, it can be vinyl, allyl, 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl, 5-hexenyl, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, or 5-hexynyl.

Specific examples of W1 include,

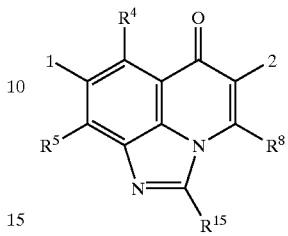

W1.1

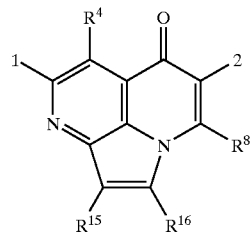

W1.2

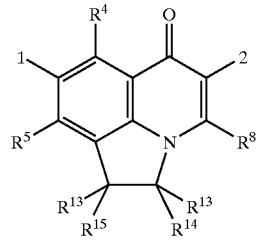

W1.3

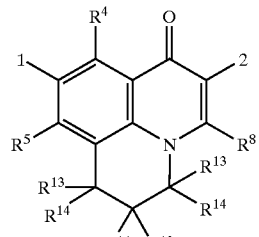

W1.4

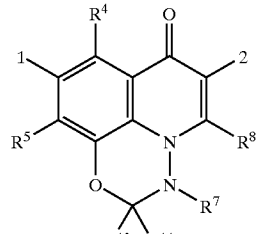

W1.5

W1.6
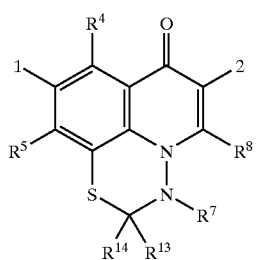
W1.7
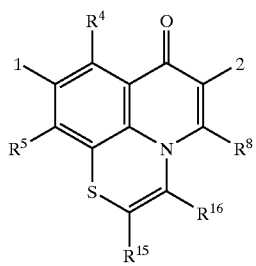
W1.8
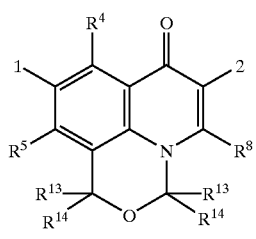
W1.9
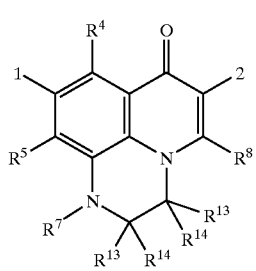
W1.10
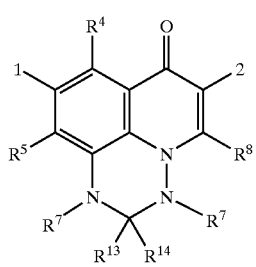
W1.11
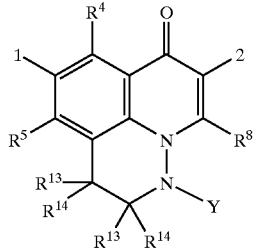
W1.12
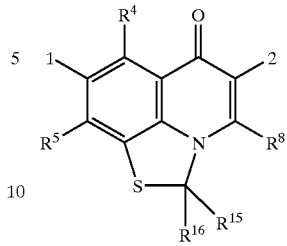
W1.13
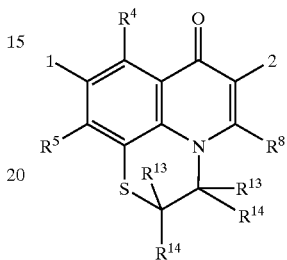
W1.14
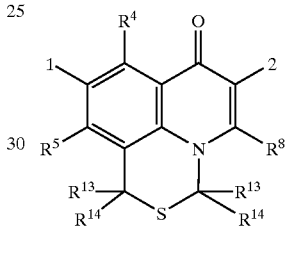
W1.15
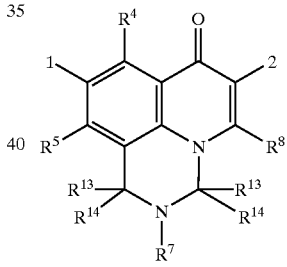
W1.16
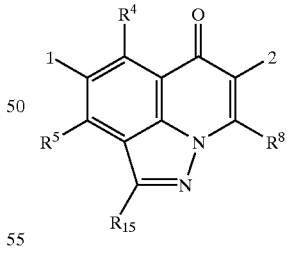
W1.17
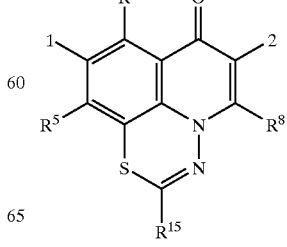

-continued
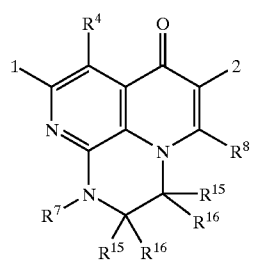
W1.18
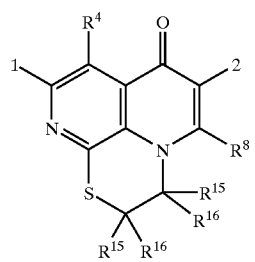
W1.19
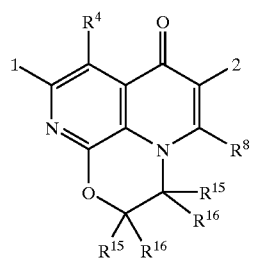
W1.20
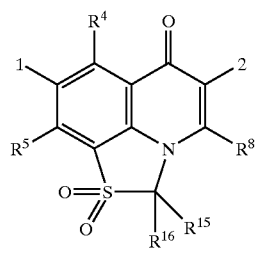
W1.21
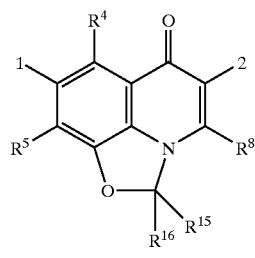
W1.22
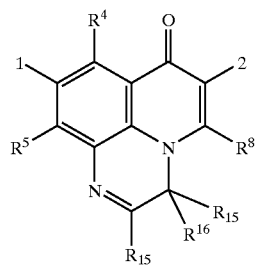
W1.23
-continued
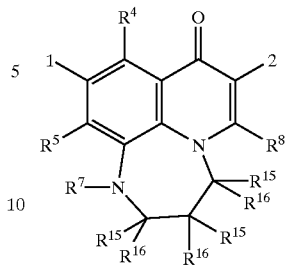
W1.24
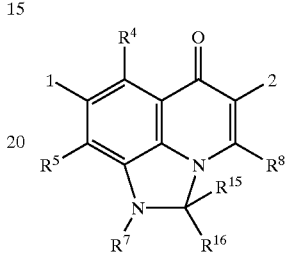
W1.25
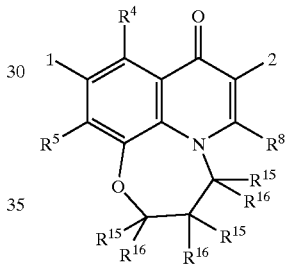
W1.26
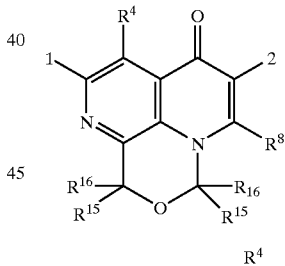
W1.27
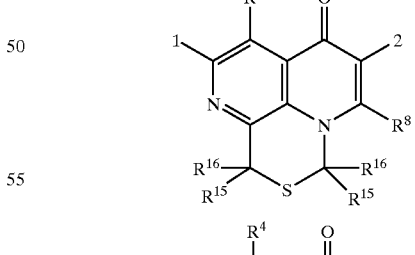
W1.28
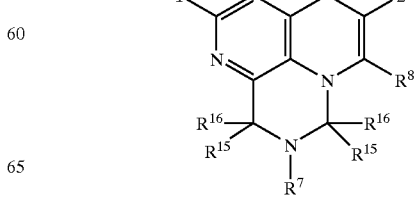
W1.29

-continued
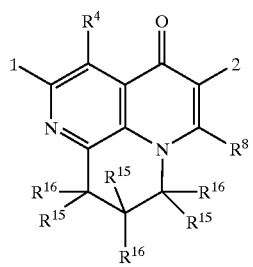
W1.30
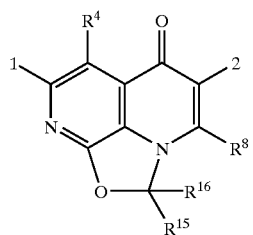
W1.31
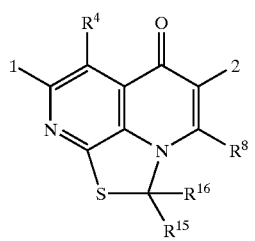
W1.32
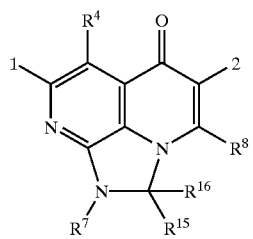
W1.33
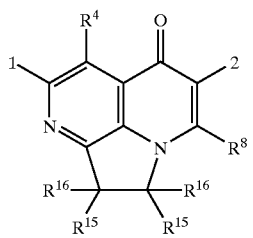
W1.34
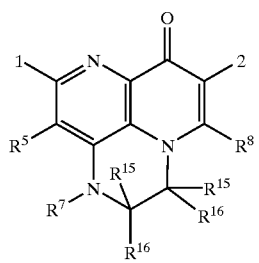
W1.35
-continued
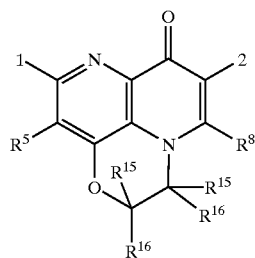
W1.36
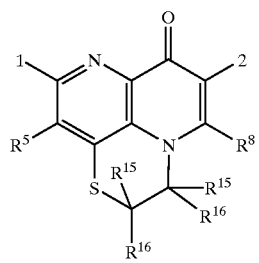
W1.37
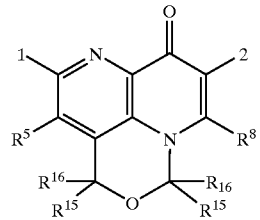
W1.38
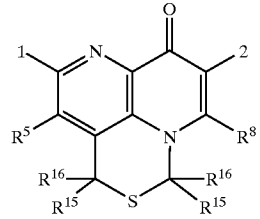
W1.39
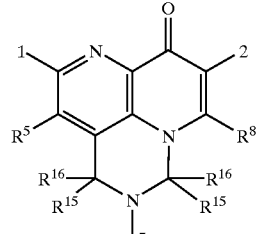
W1.40
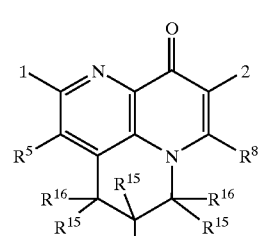
W1.41

-continued
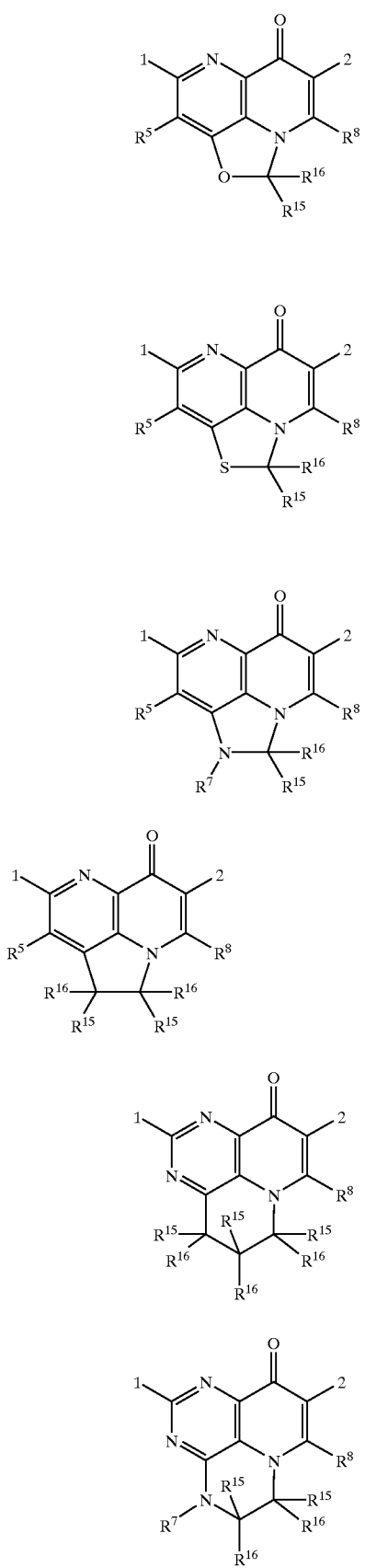
W1.42
W1.43
W1.44
W1.45
W1.46
W1.47
-continued
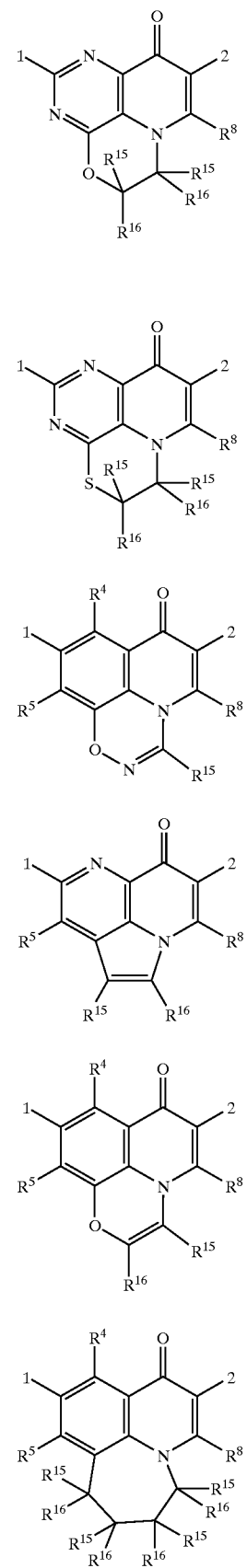
W1.48
W1.49
W1.50
W1.51
W1.52
W1.53

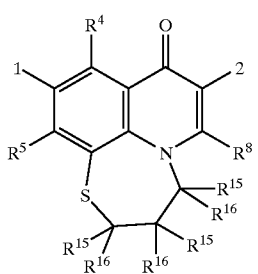 W1.54
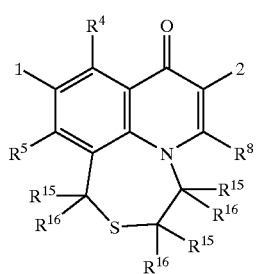 W1.59
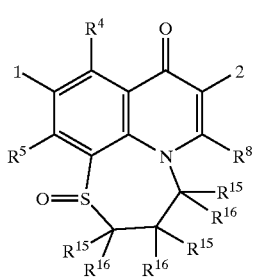 W1.55
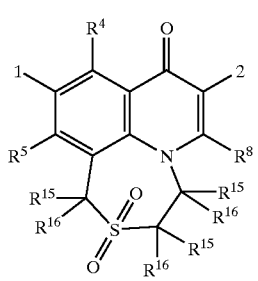 W1.60
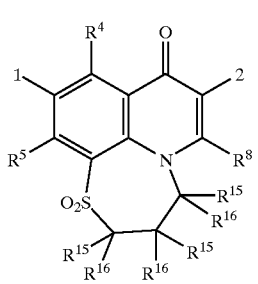 W1.56
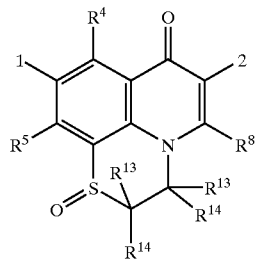 W1.61
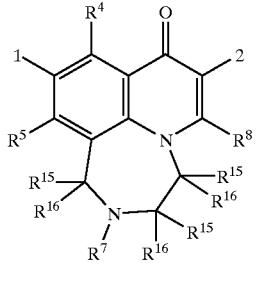 W1.57
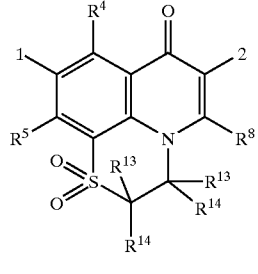 W1.62
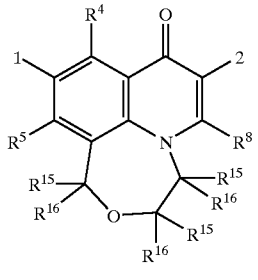 W1.58
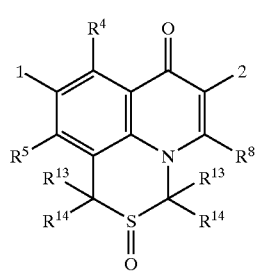 W1.63

W1.64
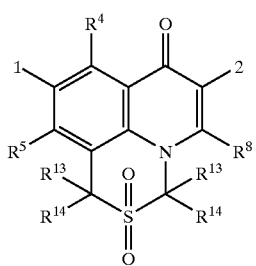
W1.65
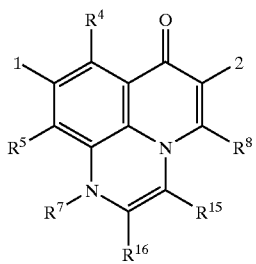
Specific examples of W2 include,
W2.1
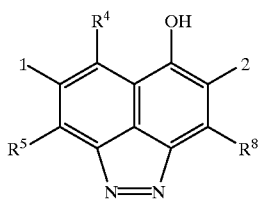
W2.2
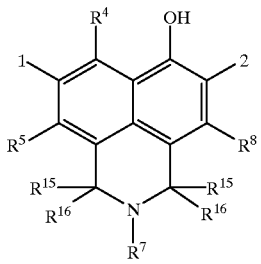
W2.3
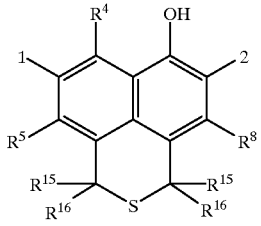
W2.4
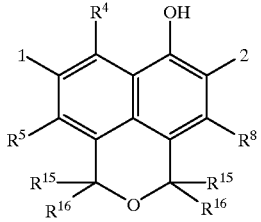
W2.5
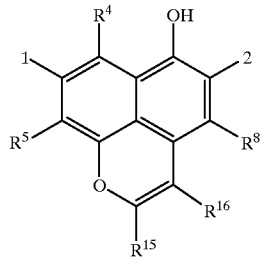
W2.6
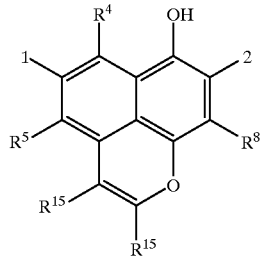
W2.7
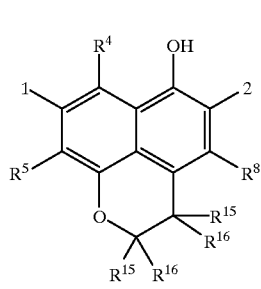
W2.8
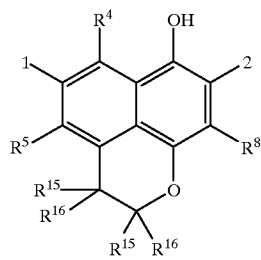
W2.9
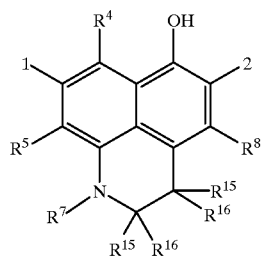
W2.10
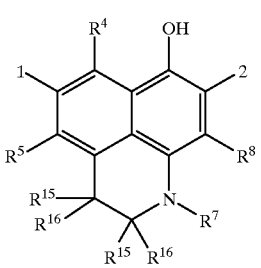

W2.11 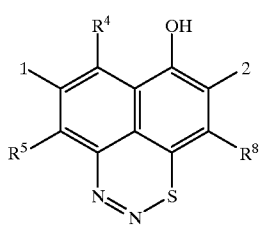
W2.12 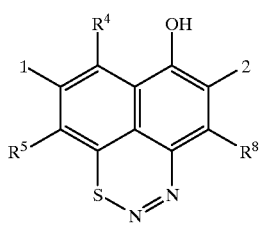
W2.13 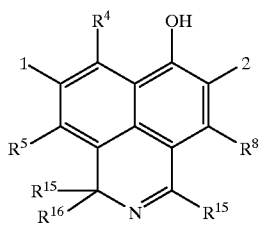
W2.14 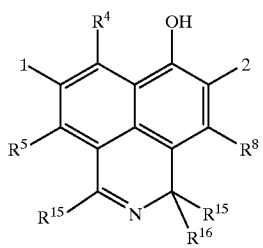
Specific examples of W3 include:
W3.1 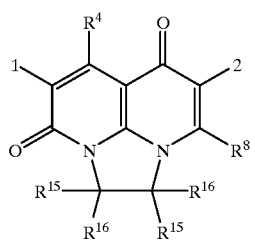
W3.2 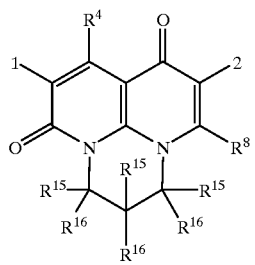
W3.1 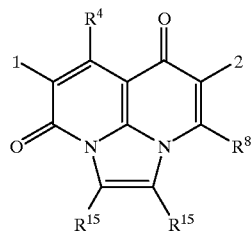
Specific examples of W4 include,
W4.1 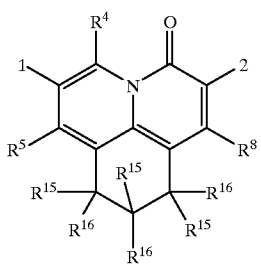
W4.2 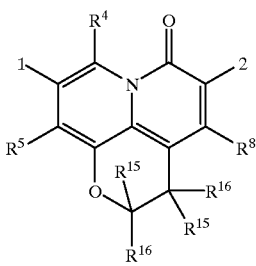
W4.3 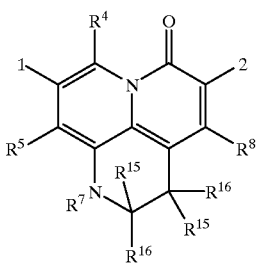
W4.4 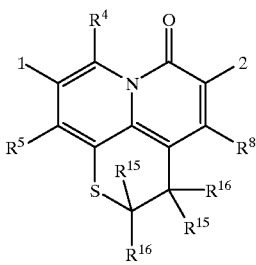

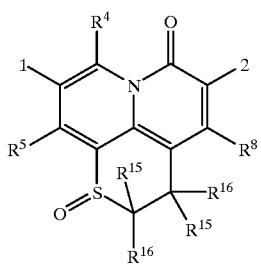
W4.5
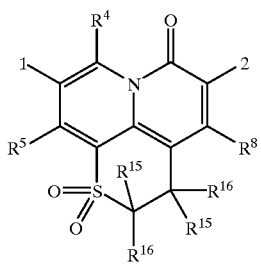
W4.6
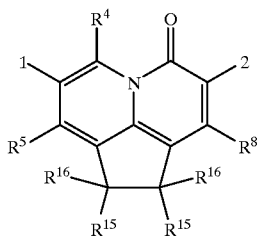
W4.7
Specific examples of W5 include:
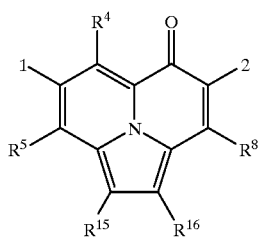
W5.1
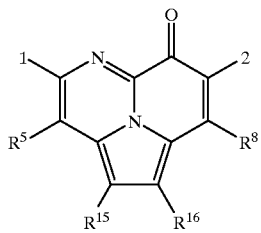
W5.2
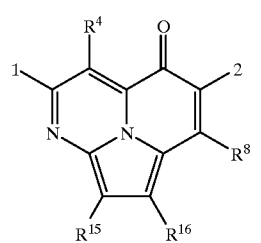
W5.3
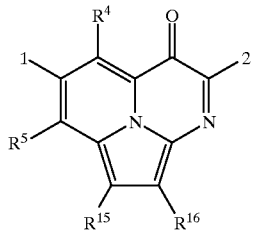
W5.4
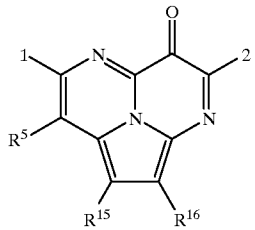
W5.5
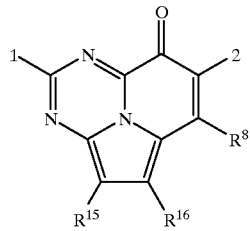
W5.6
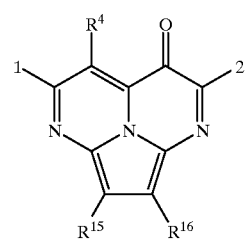
W5.7
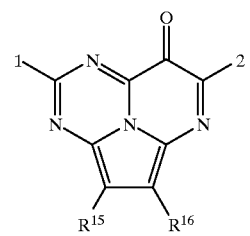
W5.8
Specific examples of W6 include:
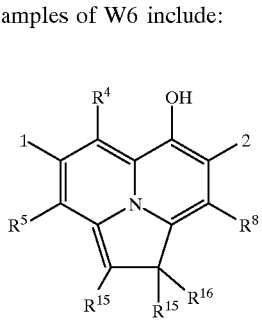
W6.1

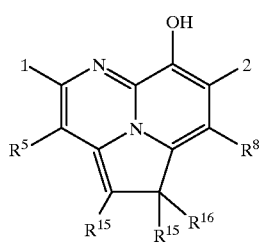 W6.2
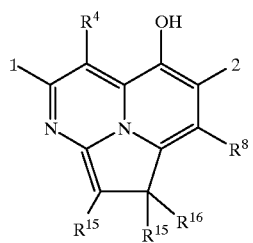 W6.3
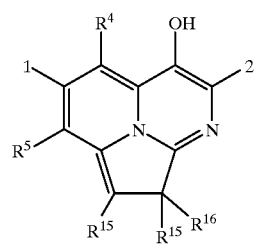 W6.4
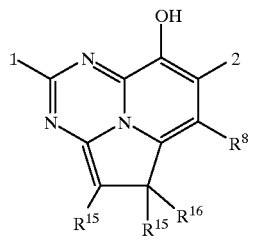 W6.5
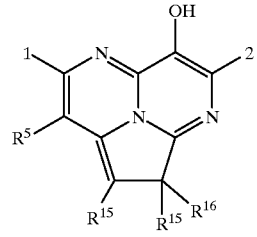 W6.6
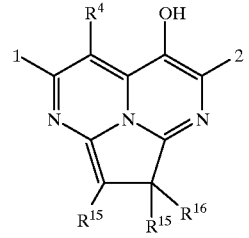 W6.7
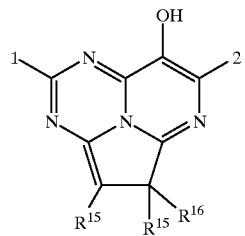 W6.8
Specific examples of W7 include,
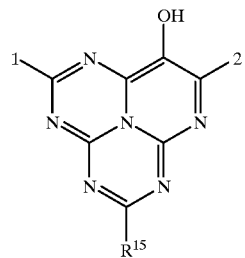 W7.1
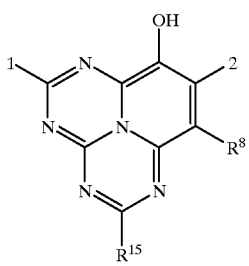 W7.2
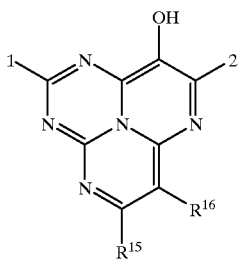 W7.3
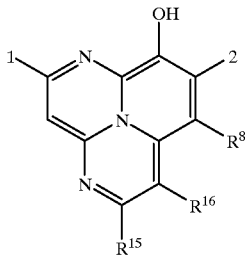 W7.4

-continued
W7.5
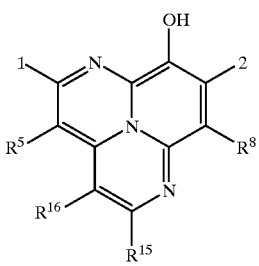
W7.6
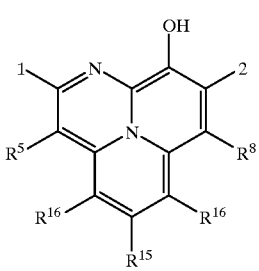
W7.7
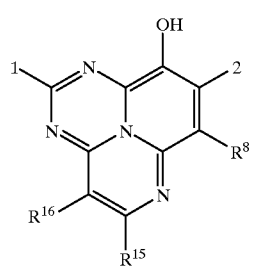
W7.8
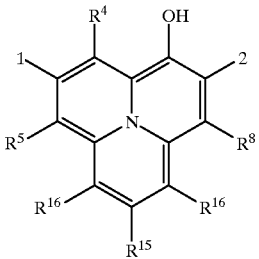
Specific examples of W8 include:
W8.1
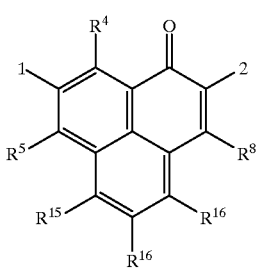
-continued
W8.2
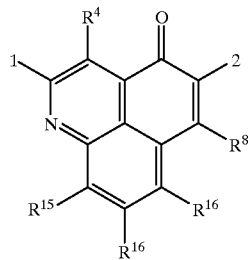
W8.3
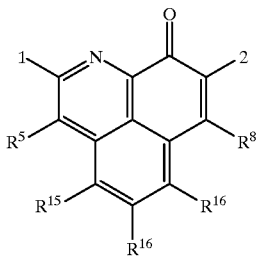
W8.4
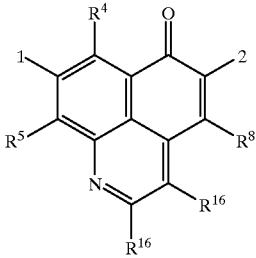
W8.5
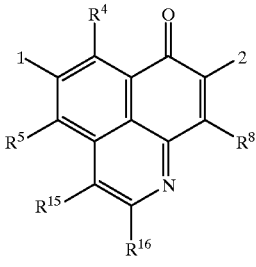
W8.6
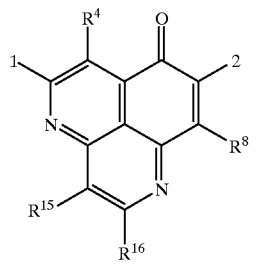
Particularly preferred compounds are those where X is Cl and G is 4-morpholinylmethyl.
Examples of the present invention include, but are not limited to the following:
N-(4-chlorobenzyl)-8-(4-morpholinylmethyl)-6-oxo-6H-imidazo[4,5,1-ij]quinoline-5-carboxamide;

N-(4-chlorobenzyl)-8-(3-hydroxy-1-propynyl)-6-oxo-6H-imidazo[4,5,1-ij]quinoline-5-carboxamide;

N-(4-chlorobenzyl)-8-(3-hydroxypropyl)-6-oxo-6H-imidazo[4,5,1-ij]quinoline-5-carboxamide;

1-amino-N-(4-chlorobenzyl)-8-(3-hydroxy-1-propynyl)-6-oxo-1,2-dihydro-6H-pyrrolo[3,2,1-ij]quinoline-5-carboxamide;

1-amino-N-(4-chlorobenzyl)-8-(3-hydroxypropyl)-6-oxo-1,2-dihydro-6H-pyrrolo-[3,2,1-ij]quinoline-5-carboxamide;

1-amino-N-(4-chlorobenzyl)-8-(4-morpholinylmethyl)-6-oxo-1,2-dihydro-6H-pyrrolo[3,2,1-ij]quinoline-5-carboxamide;

N-(4-chlorobenzyl)-2-(hydroxymethyl)-8-(3-hydroxy-1-propynyl)-6-oxo-1,2-dihydro-6H-pyrrolo[3,2,1-ij]quinoline-5-carboxamide;

N-(4-chlorobenzyl)-8-(3-hydroxyprop-1-ynyl)-2,2-dimethyl-6-oxo-1,2-dihydro-6H-pyrrolo[3,2,1-ij]quinoline-5-carboxamide;

3-benzyl-N-(4-chlorobenzyl)-9-(3-hydroxy-1-propynyl)-7-oxo-2,3-dihydro-7H-[1,3,4]oxadiazino[6,5,4-ij]quinoline-6-carboxamide;

3-benzyl-N-(4-chlorobenzyl)-9-(3-hydroxypropyl)-7-oxo-2,3-dihydro-7H-[1,3,4]oxadiazino[6,5,4-ij]quinoline-6-carboxamide;

3-benzyl-N-(4-chlorobenzyl)-9-(4-morpholinylmethyl)-7-oxo-2,3-dihydro-7H-[1,3,4]oxadiazino[6,5,4-ij]quinoline-6-carboxamide;

3-benzyl-N-(4-chlorobenzyl)-9-(tetrahydro-2H-pyran-4-ylmethyl)-7-oxo-2,3-dihydro-7H-[1,3,4]oxadiazino[6,5,4-ij]quinoline-6-carboxamide;

N-(4-chlorobenzyl)-9-(3-hydroxyprop-1-ynyl)-3-methyl-7-oxo-2,3-dihydro-7H-[1,3,4]oxadiazino[6,5,4-ij]quinoline-6-carboxamide;

3-benzyl-N-(4-chlorobenzyl)-9-(3-hydroxy-1-propynyl)-7-oxo-2,3-dihydro-7H-[1,3,4]thiadiazino[6,5,4-ij]quinoline-6-carboxamide;

3-benzyl-N-(4-chlorobenzyl)-9-(3-hydroxypropyl)-7-oxo-2,3-dihydro-7H-[1,3,4]thiadiazino[6,5,4-ij]quinoline-6-carboxamide;

3-benzyl-N-(4-chlorobenzyl)-9-(4-morpholinylmethyl)-7-oxo-2,3-dihydro-7H-[1,3,4]thiadiazino[6,5,4-ij]quinoline-6-carboxamide;

3-benzyl-N-(4-chlorobenzyl)-9-(tetrahydro-2H-pyran-4-ylmethyl)-7-oxo-2,3-dihydro-7H-[1,3,4]thiadiazino[6,5,4-ij]quinoline-6-carboxamide;

N-(4-chlorobenzyl)-3-methyl-9-(morpholin-4-ylmethyl)-7-oxo-7H-[1,4]thiazino[2,3,4-ij]quinoline-6-carboxamide;

N-(4-chlorobenzyl)-3-methyl-7-oxo-9-(tetrahydro-2H-pyran-4-ylmethyl)-7H-[1,4]thiazino[2,3,4-ij]quinoline-6-carboxamide;

N-(4-chlorobenzyl)-9-(3-hydroxypropyl)-3-methyl-7-oxo-7H-[1,4]thiazino[2,3,4-ij]quinoline-6-carboxamide;

N-(4-chlorobenzyl)-9-(3-hydroxyprop-1-ynyl)-3-methyl-7-oxo-7H-[1,4]thiazino[2,3,4-ij]quinoline-6-carboxamide;

N-(4-chlorobenzyl)-9-(morpholin-4-ylmethyl)-7-oxo-2-pyridin-3-yl-7H-[1,4]thiazino[2,3,4-ij]quinoline-6-carboxamide;

N-(4-chlorobenzyl)-9-(3-hydroxy-1-propynyl)-7-oxo-3-phenyl-1H,7H-[1,3]oxazino[5,4,3-ij]quinoline-6-carboxamide;

N-(4-chlorobenzyl)-9-(3-hydroxypropyl)-7-oxo-3-phenyl-1H,7H-[1,3]oxazino[5,4,3-ij]quinoline-6-carboxamide;

N-(4-chlorobenzyl)-7-oxo-3-phenyl-9-(tetrahydro-2H-pyran-4-ylmethyl)-1H,7H-[1,3]oxazino [5,4,3-ij]quinoline-6-carboxamide;

N-(4-chlorobenzyl)-9-(4-morpholinylmethyl)-7-oxo-3-phenyl-1H,7H-[1,3]oxazino[5,4,3-ij]quinoline-6-carboxamide;

N-(4-chlorobenzyl)-9-(3-hydroxy-1-propynyl)-1-methyl-7-oxo-3-phenyl-2,3-dihydro-1H,7H-pyrido[1,2,3-de]quinoxaline-6-carboxamide;

N-(4-chlorobenzyl)-9-(3-hydroxypropyl)-1-methyl-7-oxo-3-phenyl-2,3-dihydro-1H,7H-pyrido[1,2,3-de]quinoxaline-6-carboxamide;

N-(4-chlorobenzyl)-9-(tetrahydro-2H-pyran-4-ylmethyl)-1-methyl-7-oxo-3-phenyl-2,3-dihydro-1H,7H-pyrido[1,2,3-de]quinoxaline-6-carboxamide;

N-(4-chlorobenzyl)-9-(4-morpholinylmethyl)-1-methyl-7-oxo-3-phenyl-2,3-dihydro-1H,7H-pyrido[1,2,3-de]quinoxaline-6-carboxamide;

N-(4-chlorobenzyl)-9-(3-hydroxy-1-propynyl)-2,3,7-trioxo-2,3-dihydro-1H,7H-pyrido[1,2,3-de]quinoxaline-6-carboxamide;

N-(4-chlorobenzyl)-9-(3-hydroxypropyl)-2,3,7-trioxo-2,3-dihydro-1H,7H-pyrido[1,2,3-de]quinoxaline-6-carboxamide;

N-(4-chlorobenzyl)-9-(4-morpholinylmethyl)-2,3,7-trioxo-2,3-dihydro-1H,7H-pyrido[1,2,3-de]quinoxaline-6-carboxamide;

N-(4-chlorobenzyl)-9-(3-hydroxy-1-propynyl)-2,7-dioxo-2,3-dihydro-1H,7H-pyrido[1,2,3-de]quinoxaline-6-carboxamide;

N-(4-chlorobenzyl)-9-(3-hydroxypropyl)-2,7-dioxo-2,3-dihydro-1H,7H-pyrido[1,2,3-de]quinoxaline-6-carboxamide;

N-(4-chlorobenzyl)-9-(3-hydroxy-1-propynyl)-3,7-dioxo-2,3-dihydro-1H,7H-pyrido[1,2,3-de]quinoxaline-6-carboxamide;

N-(4-chlorobenzyl)-9-(3-hydroxypropyl)-3,7-dioxo-2,3-dihydro-1H,7H-pyrido[1,2,3-de]quinoxaline-6-carboxamide;

N-(4-chlorobenzyl)-9-(4-morpholinylmethyl)-3,7-dioxo-2,3-dihydro-1H,7H-pyrido[1,2,3-de]quinoxaline-6-carboxamide;

N-(4-chlorobenzyl)-9-(4-morpholinylmethyl)-2,7-dioxo-2,3-dihydro-1H,7H-pyrido[1,2,3-de]quinoxaline-6-carboxamide;

N-(4-chlorobenzyl)-9-(3-hydroxy-1-propynyl)-1-methyl-2,7-dioxo-2,3-dihydro-1H,7H-pyrido[1,2,3-de]quinoxaline-6-carboxamide;

3-benzyl-N-(4-chlorobenzyl)-9-(3-hydroxy-1-propynyl)-1-methyl-7-oxo-2,3-dihydro-1H,7H-[1,2,4]triazino[5,6,1-ij]quinoline-6-carboxamide;

3-benzyl-N-(4-chlorobenzyl)-9-(3-hydroxypropyl)-1-methyl-7-oxo-2,3-dihydro-1H,7H-[1,2,4]triazino[5,6,1-ij]quinoline-6-carboxamide;

3-benzyl-N-(4-chlorobenzyl)-9-(4-morpholinylmethyl)-1-methyl-7-oxo-2,3-dihydro-1H,7H-[1,2,4]triazino[5,6,1-ij]quinoline-6-carboxamide;

3-benzyl-N-(4-chlorobenzyl)-9-(tetrahydro-2H-pyran-4-ylmethyl)-1-methyl-7-oxo-2,3-dihydro-1H,7H-[1,2,4]triazino[5,6,1-ij]quinoline-6-carboxamide;

1-benzyl-N-(4-chlorobenzyl)-5-(3-hydroxy-1-propynyl)-2,7-dioxo-2,3-dihydro-1H,7H-pyrido[3,2,1-ij]cinnoline-8-carboxamide;

1-benzyl-N-(4-chlorobenzyl)-5-(3-hydroxypropyl)-2,7-dioxo-2,3-dihydro-1H,7H-pyrido[3,2,1-ij]cinnoline-8-carboxamide;

1-benzyl-N-(4-chorobenzyl)-5-(4-morpholinylmethyl)-2,7-dioxo-2,3-dihydro-1H,7H-pyrido[3,2,1-ij]cinnoline-8-carboxamide;

1-benzyl-N-(4-chlorobenzyl)-5-(tetrahydro-2H-pyran-4-ylmethyl)-2,7-dioxo-2,3-dihydro-1H,7H-pyrido[3,2,1-ij]cinnoline-8-carboxamide;

N-(4-Chlorobenzyl)-5-(3-hydroxyprop-1-ynyl)-1-methyl-7-oxo-2,3-dihydro-1H,7H-pyrido[3,2,1-ij]cinnoline-8-carboxamide;

N-(4-chlorobenzyl)-9-(3-hydroxy-1-propynyl)-7-oxo-3-phenyl-1H,7H-[1,3]thiazino[5,4,3-ij]quinoline-6-carboxamide;

N-(4-chlorobenzyl)-9-(3-hydroxypropyl)-7-oxo-3-phenyl-1H,7H-[1,3]thiazino[5,4,3-ij]quinoline-6-carboxamide;

N-(4-chlorobenzyl)-9-(tetrahydro-2H-pyran-4-ylmethyl)-7-oxo-3-phenyl-1H,7H-[1,3]thiazino[5,4,3-ij]quinoline-6-carboxamide;

N-(4-chlorobenzyl)-9-(4-morpholinylmethyl)-7-oxo-3-phenyl-1H,7H-[1,3]thiazino[5,4,3-ij]quinoline-6-carboxamide;

N-(4-chlorobenzyl)-9-(3-hydroxypropyl)-2-methyl-7-oxo-3-phenyl-2,3-dihydro-1H,7H-pyrido[3,2,1-ij]quinazoline-6-carboxamide;

N-(4-chlorobenzyl)-9-(3-hydroxy-1-propynyl)-2-methyl-7-oxo-3-phenyl-2,3-dihydro-1H,7H-pyrido[3,2,1-ij]quinazoline-6-carboxamide;

N-(4-chlorobenzyl)-9-(4-morpholinylmethyl)-2-methyl-7-oxo-3-phenyl-2,3-dihydro-1H,7H-pyrido[3,2,1-ij]quinazoline-6-carboxamide;

N-(4-chlorobenzyl)-9-(tetrahydro-2H-pyran-4-ylmethyl)-2-methyl-7-oxo-3-phenyl-2,3-dihydro-1H,7H-pyrido[3,2,1-ij]quinazoline-6-carboxamide;

2-benzyl-N-(4-chlorobenzyl)-9-(4-morpholinylmethyl)-7-oxo-2,3-dihydro-1H,7H-pyrido[3,2,1-ij]quinazoline-6-carboxamide;

2-benzyl-N-(4-chlorobenzyl)-9-(4-morpholinylmethyl)-3,7-dioxo-2,3-dihydro-1H,7H-pyrido[3,2,1-ij]quinazoline-6-carboxamide;

N-(4-chlorobenzyl)-9-(3-hydroxy-1-propynyl)-2-(4-morpholinyl)-7-oxo-7H-[1,3,4]thiadiazino[6,5,4-ij]quinoline-6-carboxamide;

N-(4-chlorobenzyl)-9-(3-hydroxypropyl)-2-(4-morpholinyl)-7-oxo-7H-[1,3,4]thiadiazino[6,5,4-ij]quinoline-6-carboxamide;

N-(4-chlorobenzyl)-2-(4-morpholinyl)-9-(4-morpholinylmethyl)-7-oxo-7H-[1,3,4]thiadiazino[6,5,4-ij]quinoline-6-carboxamide;

N-(4-chlorobenzyl)-2-(4-morpholinyl)-9-(tetrahydro-2H-pyran-4-methyl)-7H-[1,3,4]thiadiazino[6,5,4-ij]quinoline-6-carboxamide;

N-(4-chlorobenzyl)-9-(3-hydroxypropyl)-7-oxo-2,3-dihydro-1H,7H-pyrazino[3,2,1-ij][1,7]naphthyridine-6-carboxamide;

N-(4-chlorobenzyl)-9-(4-morpholinylmethyl)-7-oxo-2,3-dihydro-1H,7H-pyrazino[3,2,1-ij][1,7]naphthyridine-6-carboxamide;

N-(4-chlorobenzyl)-9-(3-hydroxy-1-propynyl)-7-oxo-2,3-dihydro-1H,7H-pyrazino[3,2,1-ij][1,7]naphthyridine-6-carboxamide;

N-(4-chlorobenzyl)-9-(3-hydroxypropyl)-7-oxo-2,3-dihydro-7H-[1,4]thiazino[2,3,4-ij][1,7]naphthyridine-6-carboxamide;

N-(4-chlorobenzyl)-9-(4-morpholinylmethyl)-7-oxo-2,3-dihydro-7H-[1,4]thiazino[2,3,4-ij][1,7]naphthyridine-6-carboxamide;

N-(4-chlorobenzyl)-9-(3-hydroxy-1-propynyl)-7-oxo-2,3-dihydro-7H-[1,4]thiazino[2,3,4-ij][1,7]naphthyridine-6-carboxamide;

N-(4-chlorobenzyl)-9-(3-hydroxy-1-propynyl)-7-oxo-2,3-dihydro-7H-[1,4]oxazino[2,3,4-ij][1,7]naphthyridine-6-carboxamide;

N-(4-chlorobenzyl)-9-(4-morpholinylmethyl)-7-oxo-2,3-dihydro-7H-[1,4]oxazino[2,3,4-ij][1,7]naphthyridine-6-carboxamide;

N-(4-chlorobenzyl)-9-(3-hydroxypropyl)-7-oxo-2,3-dihydro-7H-[1,4]oxazino[2,3,4-ij][1,7]naphthyridine-6-carboxamide;

N-(4-chlorobenzyl)-9-(3-hydroxypropyl)-3,7-dioxo-3H,7H-pyrido[1,2,3-de]quinoxaline-6carboxamide;

N-(4-chlorobenzyl)-9-(3-hydroxy-1-propynyl)-3,7-dioxo-3H,7H-pyrido[1,2,3-de]quinoxaline-6-carboxamide;

N-(4-chlorobenzyl)-9-(4-morpholinylmethyl)-3,7-dioxo-3H,7H-pyrido[1,2,3-de]quinoxaline-6-carboxamide;

N-(4-chlorobenzyl)-2-[(4-chlorobenzyl)amino]-9-(4-morpholinylmethyl)-7-oxo-3H,7H-pyrido[1,2,3-de]quinoxaline-6-carboxamide;

2-(benzylamino)-N-(4-chlorobenzyl)-9-(4-morpholinylmethyl)-7-oxo-3H,7H-pyrido[1,2,3-de]quinoxaline-6-carboxamide;

N-(4-chlorobenzyl)-10-(3-hydroxypropyl)-2,4,8-trioxo-1,2,3,4-tetrahydro-8H-[1,4]diazepino[3,2,1-ij]quinoline-7-carboxamide;

N-(4-chlorobenzyl)-10-(3-hydroxy-1-propynyl)-2,4,8-trioxo-1,2,3,4-tetrahydro-8H-[1,4]diazepino[3,2,1-ij]quinoline-7-carboxamide;

N-(4-chlorobenzyl)-10-(4-morpholinylmethyl)-2,4,8-trioxo-1,2,3,4-tetrahydro-8H-[1,4]diazepino[3,2,1-ij]quinoline-7-carboxamide;

N-(4-chlorobenzyl)-10-(4-morpholinylmethyl)-2,8-dioxo-1,2,3,4-tetrahydro-8H-[1,4]diazepino[3,2,1-ij]quinoline-7-carboxamide;

N-(4-chlorobenzyl)-8-(4-morpholinylmethyl)-2,6-dioxo-1,2-dihydro-6H-imidazo[4,5,1-ij]quinoline-5-carboxamide;

N-(4-chlorobenzyl)-8-(3-hydroxy-1-propynyl)-2,6-dioxo-1,2-dihydro-6H-imidazo[4,5,1-ij]quinoline-5carboxamide;

N-(4-chlorobenzyl)-8-(3-hydroxypropyl)-2,6-dioxo-1,2-dihydro-6H-imidazo[4,5,1-ij]quinoline-5-carboxamide;

N-(4-chlorobenzyl)-8-(4-morpholinylmethyl)-2,6-dioxo-1-[2-(1-piperidinyl)ethyl]-1,2-dihydro-6H-imidazo[4,5,1-ij]quinoline-5-carboxamide;

N-(4-chlorobenzyl)-1-[2-(4-methyl-1-piperazinyl)ethyl]-8-(4-morpholinylmethyl)-2,6-dioxo-1,2-dihydro-6H-imidazo[4,5,1-ij]quinoline-5-carboxamide;

N-(4-chlorobenzyl)-10-(4-morpholinylmethyl)-8-oxo-3,4-dihydro-2H,8H-[1,4]oxazepino[2,3,4-ij]quinoline-7-carboxamide;

N-(4-chlorobenzyl)-3-methyl-9-(morpholin-4-ylmethyl)-7-oxo-7H-[1,4]oxazino[2,3,4-ij]quinoline-6-carboxamide;

N-(4-chlorobenzyl)-3-methyl-7-oxo-9-(tetrahydro-2H-pyran-4-ylmethyl)-7H-[1,4]oxazino[2,3,4-ij]quinoline-6-carboxamide;

N-(4-chlorobenzyl)-9-(3-hydroxypropyl)-3-methyl-7-oxo-7H-[1,4]oxazino[2,3,4-ij]quinoline-6-carboxamide;

N-(4-chlorobenzyl)-9-(3-hydroxyprop-1-ynyl)-3-methyl-7-oxo-7H-[1,4]oxazino [2,3,4-ij]quinoline-6-carboxamide;

N-(4-chlorobenzyl)-9-(morpholin-4-ylmethyl)-7-oxo-2-pyridin-3-yl-7H-[1,4]oxazino[2,3,4-ij]quinoline-6-carboxamide;

2-benzyl-N-(4-chlorobenzyl)-10-(4-morpholinylmethyl)-3,8-dioxo-1,2,3,4-tetrahydro-8H-[1,4]diazepino[6,7,1-ij]quinoline-7-carboxamide;

N-(4-chlorobenzyl)-5-(3-hydroxypropyl)-4,7-dioxo-1,2-dihydro-4H,7H-imidazo[1,2,3-ij][1,8]naphthyridine-8-carboxamide;

N-(4-chlorobenzyl)-5-(4-morpholinylmethyl)-4,7-dioxo-1,2-dihydro-4H,7H-imidazo[1,2,3-ij][1,8]naphthyridine-8-carboxamide;

N-(4-chlorobenzyl)-5-(3-hydroxy-1-propynyl)-4,7-dioxo-1,2-dihydro-4H,7H-imidazo[1,2,3-ij][1,8]naphthyridine-8-carboxamide;

N-(4-chlorobenzyl)-6-(4-morpholinylmethyl)-3-oxo-9,10-dihydro-3H,8H-pyrido [3,2,1-ij]quinoline-2-carboxamide;

N-(4-chlorobenzyl)-3-methyl-9-(4-morpholinylmethyl)-2,7-dioxo-2,3-dihydro-1H,7H-pyrido[1,2,3-de]quinoxaline-6-carboxamide hydrobromide;

and pharmaceutically acceptable salts thereof.

Representative examples of the synthesis of compounds falling within the scope of formulas W1-W8 are as follows.

The following Charts A–BQ describe the preparation of the compounds of the present invention. All of the starting materials are prepared by procedures described in these charts or by procedures analogous thereto, which would be well known to one of ordinary skill in organic chemistry. All of the final compounds of the present invention are prepared by procedures described in these charts or by procedures analogous thereto, which would be well known to one of ordinary skill in organic chemistry. All of the variables used in the charts are as defined below or as in the claims.

W1.1. 6-Oxo-6H-imidazo[4,5,1-ij]quinoline-5-carboxamides The preparation of specific examples of heterocycle W1.1 is described in Chart A. 2-Nitroaniline is iodinated with iodine monochloride to afford A.1 (Wilson, et.al., *Aust. J. Chem.*, 1983, 36, 2317–2326) which is heated with diethyl ethoxymethylenemalonate in a mixture of diphenyl ether/biphenyl, initially at 150° C. to generate diethyl 2-[(2-amino-4-iodoanilino)methylene]malonate and then at 240° C. to cyclize this intermediate to ethyl 4-hydroxy-6-iodo-8-nitro-3-quinolinecarboxylate (A.2). Stannous chloride reduction of A.2 affords ethyl 8-amino-4-hydroxy-6-iodo-3-quinolinecarboxylate A.3 which reacts with 4-chlorobenzylamine to give 8-amino-N-(4-chlorobenzyl)-4-hydroxy-6-iodo-3-quinolinecarboxamide A.4. Intermediate A.4 reacts with ethyl orthoformate to give N-(4-chlorobenzyl)-8-iodo-6-oxo-6H-imidazo[4,5,1-ij]quinoline-5-carboxamide (A.5). Palladium mediated carbonylation of A.5 in presence of tributyl tin hydride or trioctylsilane (Kotsuki et. al., *Synthesis* 1996, 470) affords A.6 which is reductively aminated with morpholine and sodium cyanoborohydride to give A.7. Specific examples in which G=3-hydroxypropyl or 3-hydroxy-1-propynyl are prepared as described in Chart B. Palladium catalyzed coupling of A.5 with an electron-rich acetylene (e.g. propargyl alcohol, Z=CH$_2$OH) gives B.1 (Sonogashira, K.; Tohada, Y.; Hagihara, N. *Tetrahedron Lett.* 1975, 50, 4467. or Fisher, M. J. et. al. *J. Med. Chem.* 1997, 40, 2085.). Saturation of the alkyne by hydrogenation catalyzed by palladium on carbon in alcoholic solvents affords alkyl derivatives of formula B.2 (Z=CH$_2$OH).

CHART A

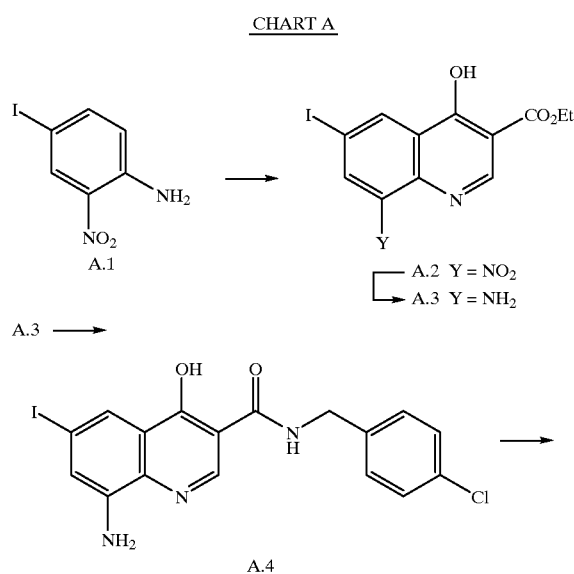

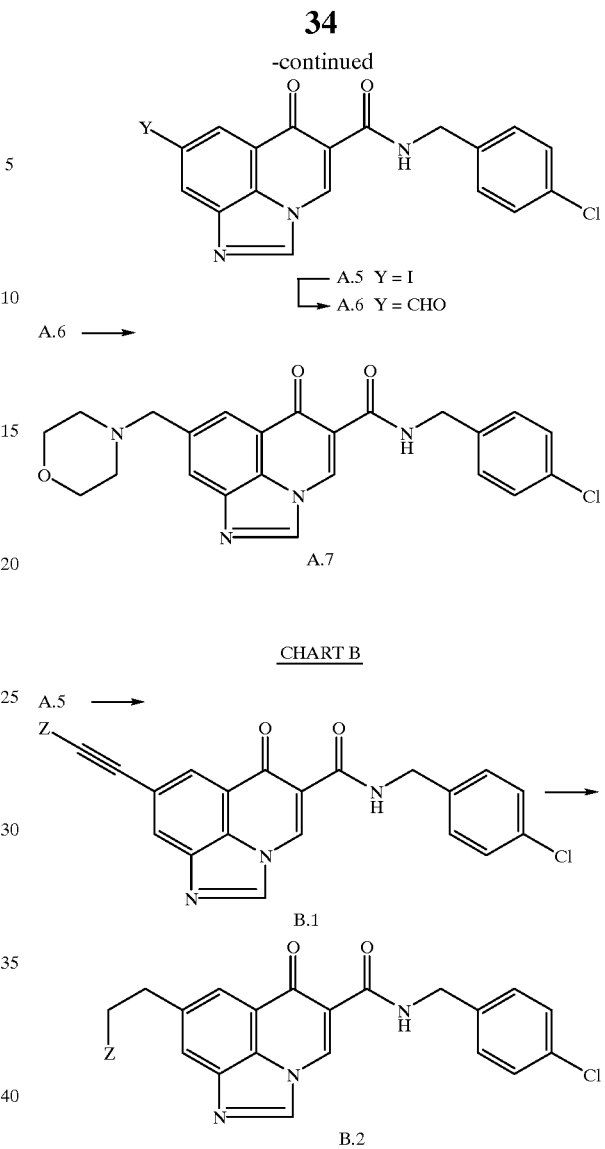

CHART B

W1.3. 6-Oxo-1,2-dihydro-6H-pyrrolo[3,2,1-ij]quinoline-5-carboxamides. The preparation of specific examples of heterocycle W1.3 is described in Chart C. Condensation of an indoline C.1 (e.g. 2,2-dimethylindoline, R$^{13}$=2,2-dimethyl) with diethyl ethoxymethylenemalonate followed by cyclization of the resulting enamine C.2 in a mixture of polyphosphoric acid or Eaton's Reagent affords esters of the formula C.3. Halogenation such as bromination employing bromine in acetic acid provides compounds of the general formula C.4. The resulting product is then coupled with an electron-rich acetylene (e.g. propargyl alcohol, Z=CH$_2$OH) catalyzed by PdCl$_2$(PPh$_3$)$_2$ and copper(I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) to provide the corresponding alkynyl derivative C.5. The resulting ester is reacted with a substituted benzylamine (e.g. 4-chlorobenzylamine, 4-fluorobenzylamine, or 4-bromobenzylamine) in the presence of sodium methoxide or other appropriate amidation catalyst to afford amides of the formula C.6. Saturation of the alkyne by hydrogenation catalyzed by palladium on carbon in alcoholic solvents affords alkyl derivatives of formula C.7 (e.g. Z=CH$_2$OH).

CHART C

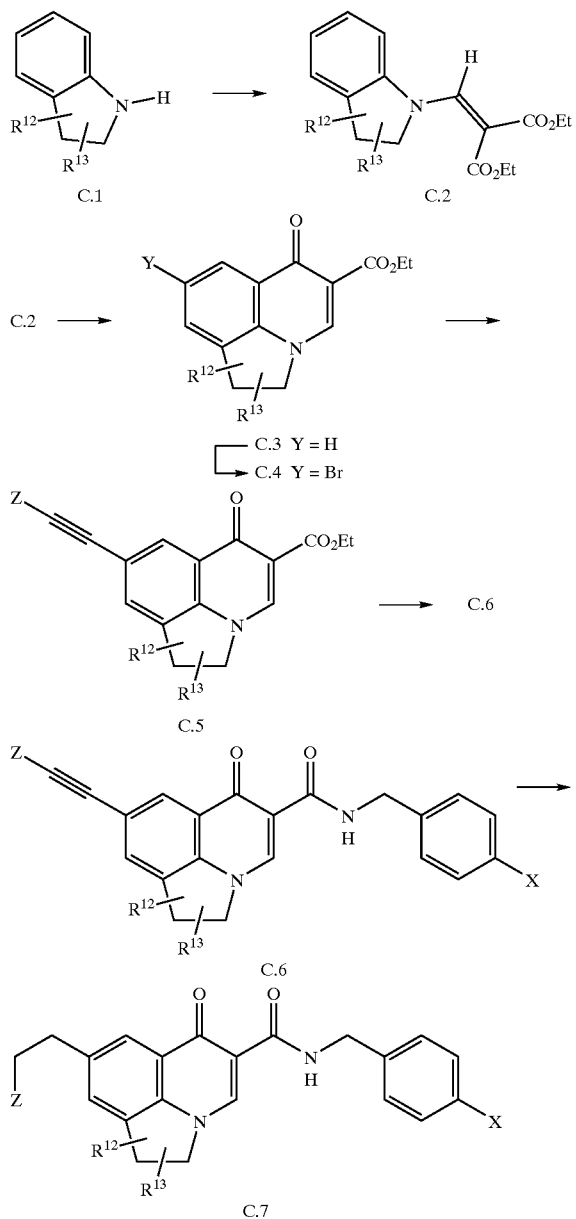

CHART D

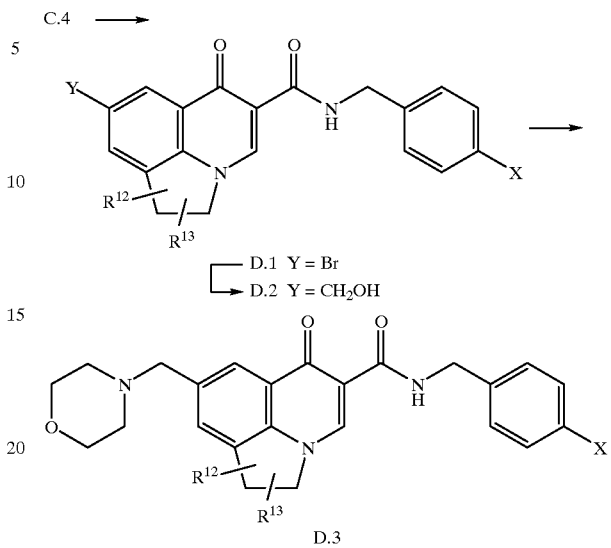

As shown in Chart E, radical bromination of compound C.5 (R=H) with N-bromosuccinimide, benzoyl peroxide, and carbon tetrachloride affords the benzylic bromide E.1. Displacement of the bromide with excess azide in an appropriate solvent such as DMF or THF at temperatures from 0–100° C. provides E.2. Elaboration of the ester to the carboxamide as described in previous examples gives intermediates of the formula E.3. This azide is reduced to give the amine E.4 by treating the azide with triphenylphosphine in THF followed by water hydrolysis of the iminophosphorane intermediate at temperatures from 10–65° C. Saturation of the alkyne by hydrogenation catalyzed by palladium on carbon in alcoholic solvents affords alkyl derivatives of formula E.5 (e.g. Z=CH$_2$OH). The amine can then be alkylated or acylated via conditions well known to those skilled in the art to give analogs defined by NR$^{10}$R$^{11}$.

CHART E

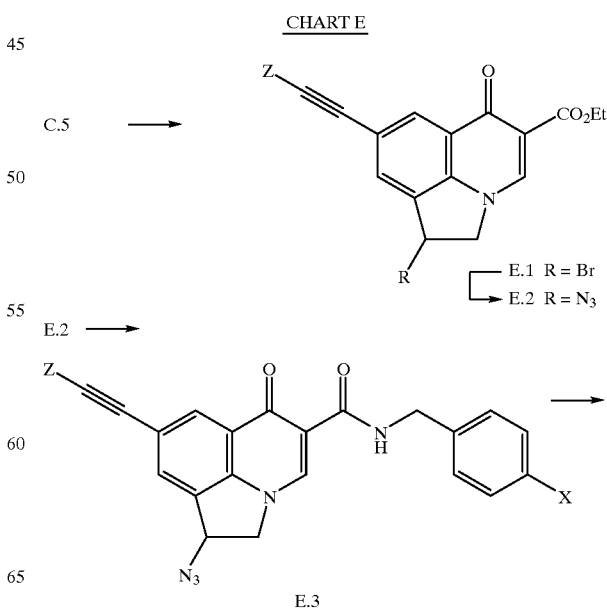

Alternatively, intermediates of the formula C.4 are derivatized as shown in Chart D. The resulting ester is reacted with a substituted benzylamine (e.g. 4-chlorobenzylamine, 4-fluorobenzylamine, or 4-bromobenzylamine) in the presence of sodium methoxide or other appropriate amidation catalyst to afford amides of the formula D.1. Coupling of compounds of the formula D.1 with hydroxymethyl(tributyl)stannane (Danheiser, R. L.; Romines, K. R.; Koyama, H. Org. Syn. 1992, 71, 133–139) and a palladium catalyst (e.g. tetrakistriphenylphosphine palladium) affords compounds of the formula D.2. Treatment of the resulting alcohol with methanesulfonyl chloride in the presence of an amine base (e.g. collidine) followed by a primary or secondary amine (HNR$^1$R$^2$, e.g. morpholine) provides compounds of the formula D.3.

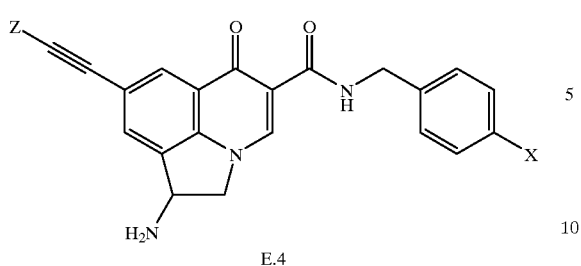

E.4

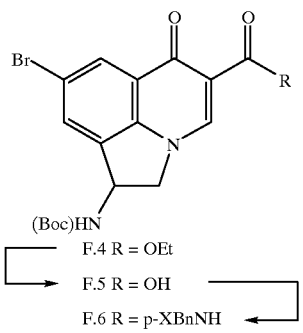

F.4 R = OEt
F.5 R = OH
F.6 R = p-XBnNH

E.4 →

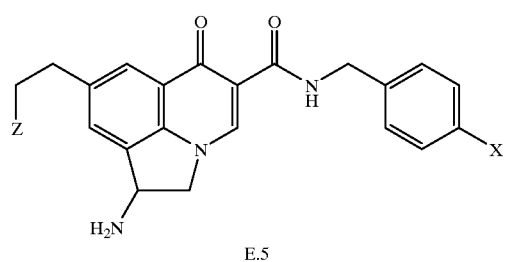

E.5

F.6 →

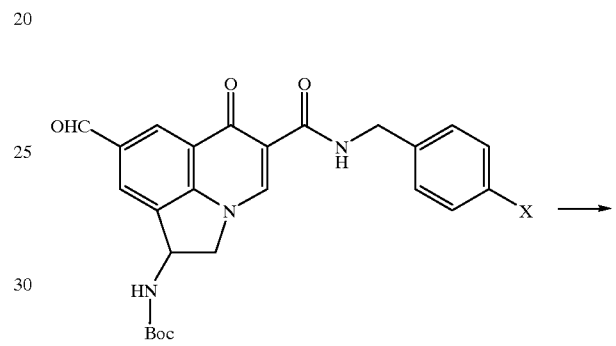

F.7

Alternatively as described in Chart F, intermediate C.3 (R=H) can be subjected to the same benzylic bromination conditions to give bromide F.1, followed by displacement of the bromide to give the azide F.2. The azide can then be reduced to the amine F.3 as described above and elaborated to the Boc-protected derivative F.4 by treating with di-t-butyldicarbonate and an appropriate base (triethylamine, NaHCO$_3$). Conversion of the ethyl ester to the carboxamide F.6 can be achieved as described in prior examples. Palladium catalyzed carbonylation of the aryl iodide in the presence of tributyltin hydride provides the aryl aldehyde F.7. Reductive amination of F.7 with a primary or secondary amine (e.g. morpholine) and sodium cyanoborohydride affords F.8. Removal of the Boc-group with HCl in dioxane or trifluoroacetic acid results in analog F.9, which can be alkylated or acylated to give a variety of analogs.

CHART F

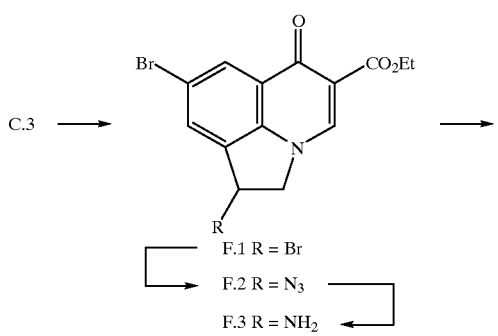

F.1 R = Br
F.2 R = N$_3$
F.3 R = NH$_2$

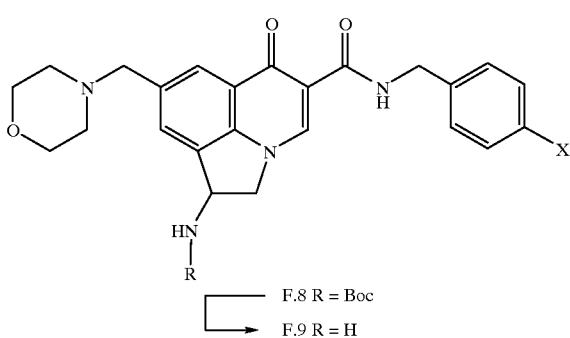

F.8 R = Boc
F.9 R = H

More specifically examples of heterocycle W1.3 are prepared as described in Chart G. Reduction of indoline-2-carboxylic acid (G.1) with borane in THF affords alcohol G.2. Protection of the indoline nitrogen as the benzyl carbamate can be achieved using benzyl chloroformate, THF, and aqueous sodium bicarbonate to give G.3. Iodination using NIS in DMF at elevated temperatures (40–80° C.) provides compound G.4. The carbamate is removed using HBr in acetic acid to give acetate G.5, which is cyclized via a two-step protocol using diethyl ethoxymethylenemalonate and Eaton's Reagent (or polyphosphoric acid) to give G.6. Condensation of this ester with a benzylamine (e.g. 4-chlorobenzylamine, 4-bromobenzylamine, or 4-fluorobenzylamine) at high temperatures affords amides of the formula G.7. This material is then coupled with an electron-rich acetylene (e.g. propargyl alcohol) catalyzed by PdCl$_2$(PPh$_3$)$_2$ and copper(I) iodide either in diethylamine or in a mixture of DMF and triethylamine to provide the corresponding alkynyl derivative G.8. Saturation of the alkyne by hydrogenation catalyzed by palladium on carbon in alcoholic solvents affords alkyl derivatives of formula

G.9.

CHART G

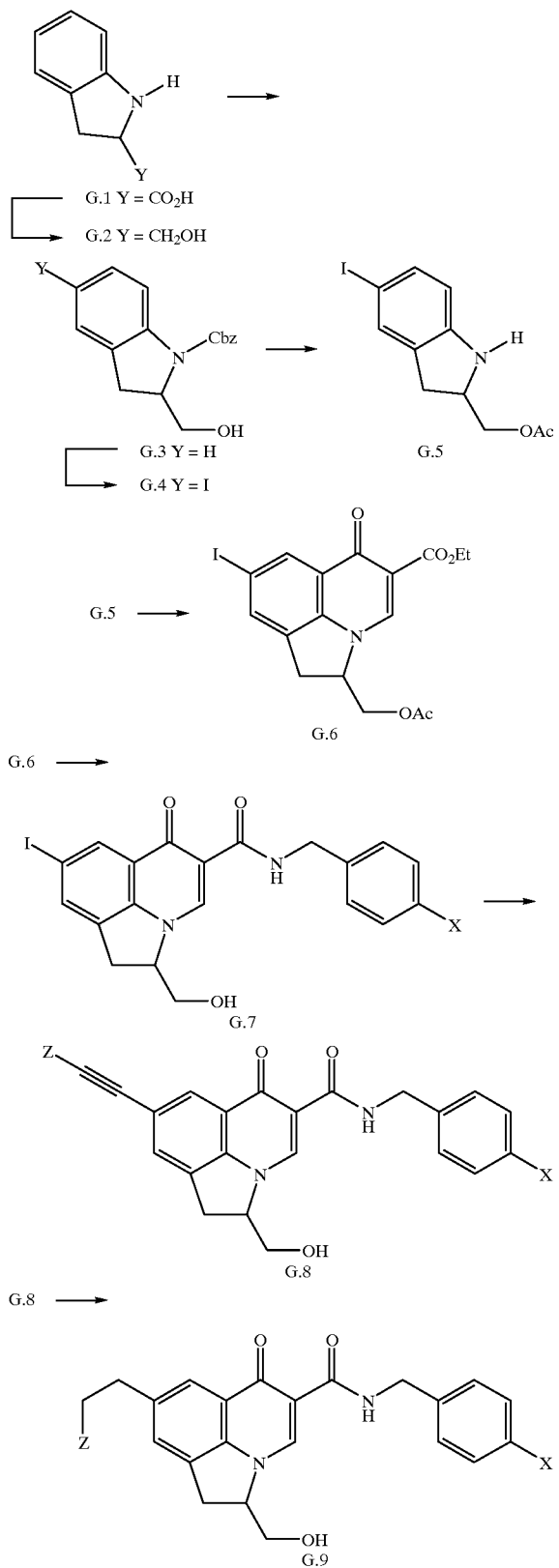

W1.5. 7-Oxo-2,3-dihydro-7H-[1,3,4]oxadiazino[6,5,4-ij] quinoline-6-carboxamides. The preparation of specific examples of heterocycle W1.5 is described in Chart H following an established literature precedent (*J. Med. Chem.* 1988, 31, 991–1001.). Reaction of β-ketoesters of the formula H.1 (prepared as described in Chart J, where Y=iodo; Chart K, where Y=morpholinylmethyl; and Chart L, where Y=4-tetrahydropyranylmethyl) with acetic anhydride and triethylorthoformate followed by treatment of the resulting enol ether with a formyl-substituted hydrazine (e.g. 1-formyl-1-methylhydrazine, $R^7$=methyl, U.S. Pat. No. 5,985,874) affords derivatives of the general formula H.2. Treatment of H.2 with potassium hydroxide followed by formic acid and formaldehyde affords cyclized compounds of the general formula H.3. The resulting carboxylic acid H.3 is then coupled with a benzylamine (e.g. 4-chlorobenzylamine, 4-fluorobenzylamine, or 4-bromobenzylamine) mediated by 1,1'-carbonyldiimidazole (or other suitable carboxylic acid activating agent) to provide amides of the general formula H.4.

CHART H

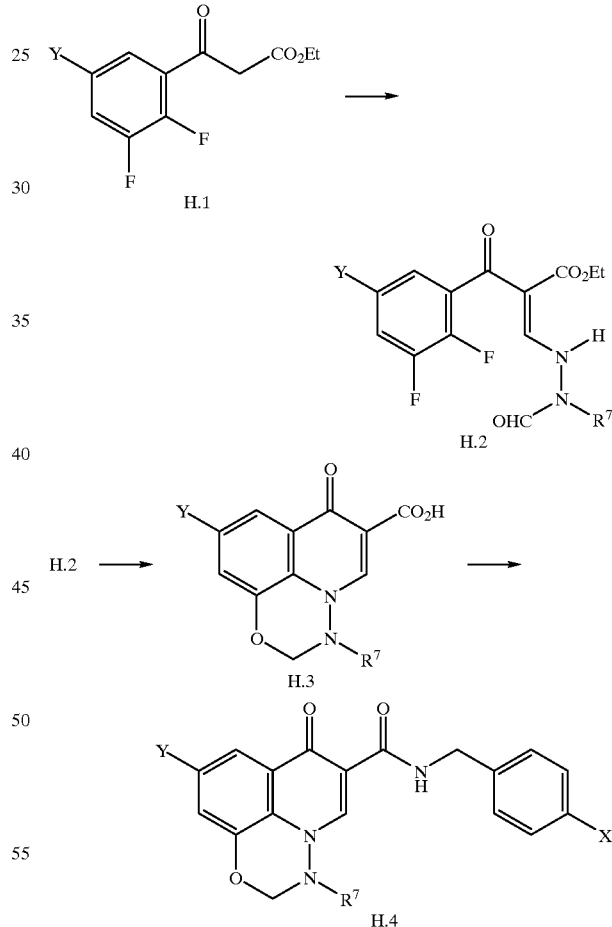

As described in Chart I, to prepare derivatives where G=3-hydroxypropyl or 3-hydroxy-1-propynyl, intermediate H.4 (Y=iodo) is further derivatized by Sonogashira coupling with an electron-rich acetylene (e.g. propargyl alcohol, Z=$CH_2OH$) catalyzed by $PdCl_2(PPh_3)_2$ and copper(I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J.*

*Med. Chem.* 1997, 40, 2085.) provides the corresponding alkynyl derivatives of formula I.1 (Z=CH$_2$OH). Saturation of the alkyne by hydrogenation catalyzed by palladium on carbon in alcoholic solvents affords alkyl derivatives of formula I.2 (Z=CH$_2$OH).

CHART I

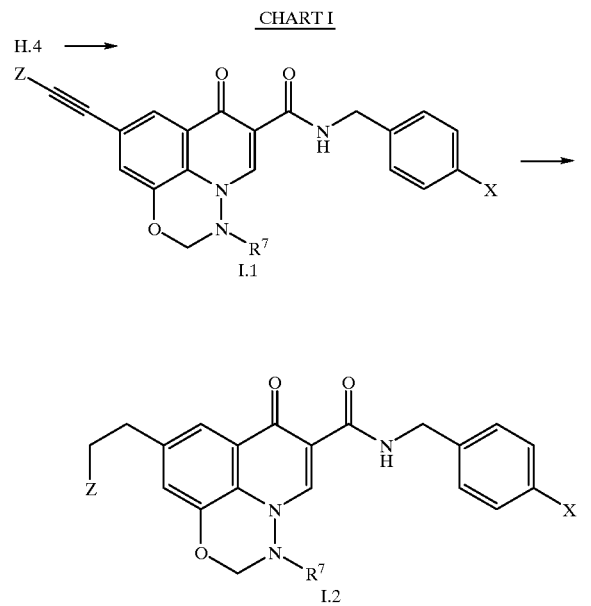

H.1 (Y=iodo) is prepared as described in Chart J. Iodination of 2,3-difluorobenzoic acid J.1 affords 2,3-difluoro-5-iodobenzoic acid J.2. Conversion of J.2 to its corresponding imidazolide with 1,1'-carbonyldiimidazole followed by treatment with the trimethylsilyl ester of ethyl hydrogen malonate in the presence of DBU (Wang, X.; William, T. M.; Napier, J. J.; Ghannam, A. *Tetrahedron Lett.* 1994, 35, 9323–9326.) provides β-ketoester H.1 (Y=iodo) which may be employed as in Chart H.

CHART J

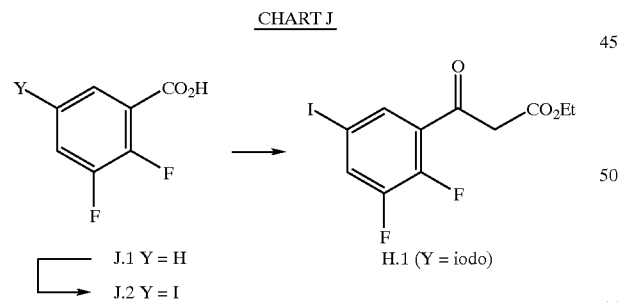

H.1 (Y=morpholinylmethyl) is prepared as described in Chart K. Reductive amination of 3,4-difluoro-4-trifluoromethylbenzaldehyde K.1 with morpholine in the presence of triacetoxyborohydride and acetic acid affords K.2. Hydrolysis of K.2 in sulfuric acid provides carboxylic acid K.3. Conversion of K.3 according to methods analogous to those described in Chart J affords β-ketoester H.1 (Y=morpholinylmethyl) which may be employed as in Chart H.

CHART K

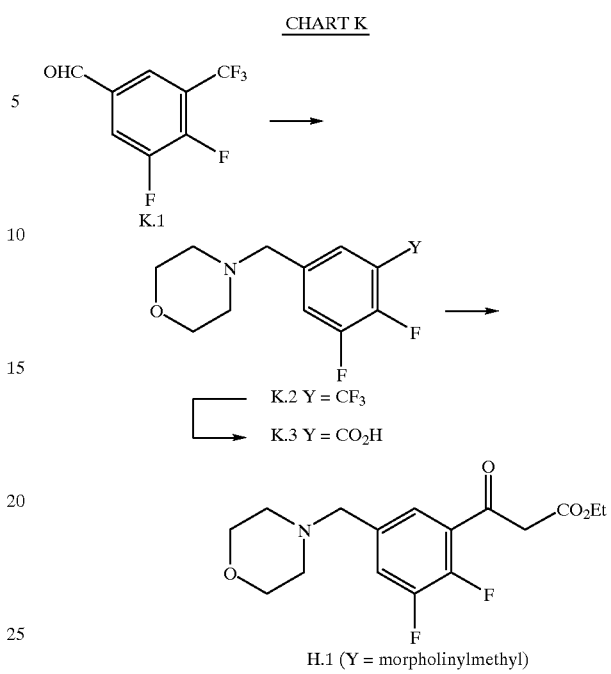

H.1 (Y=4-tetrahydropyranylmethyl) is prepared as described in Chart L. Wittig olefination between K.1 and 4-tetrahydropyranylphosphonium bromide (Bestmann, H. J.; Stransky, W.; Vostrowsky, O. *Chem. Ber.* 1979, 109, 1694–1700.) employing sodium hexamethyldisilazide as base provides the olefin L.1. Saturation of the olefin by hydrogenation of L.1 employing palladium on carbon as catalyst affords L.2. Hydrolysis of L.2 in sulfuric acid provides carboxylic acid L.3. Conversion of L.3 according to methods analogous to those described in Chart J affords β-ketoester H.1 (Y=4-tetrahydropyranylmethyl) which may be employed as in Chart H.

CHART L

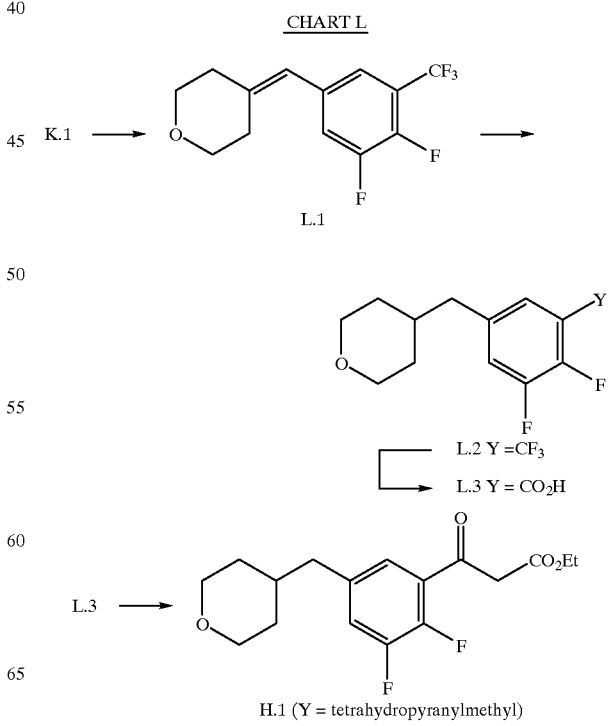

W1.6. 7-Oxo-2,3-dihydro-7H-[1,3,4]thiadiazino[6,5,4-ij]quinoline-6-carboxamides. The preparation of specific examples of heterocycle W1.6 is described in Chart M following an established literature precedent (*Bull. Chem. Soc. Jpn.* 1996, 69, 1371–1376.). Alcohol AM.4 (Y=morpholinylmethyl, tetrahydropyranylmethyl, or iodo) is treated with thionyl chloride followed by sodium thiol and then sodium hydride to afford the quinoline M.1. The resulting ester is then treated with a benzylamine (e.g. 4-chlorobenzylamine, 4-bromobenzylamine, or 4-fluorobenzylamine) at high temperature to afford the corresponding amides of the general formula M.2. Specific examples where G=3-hydroxypropyl or 3-hydroxy-1-propynyl are prepared as described in Chart N from intermediate M.2 (Y=iodo) by Sonogashira coupling with an electron-rich acetylene (e.g. propargyl alcohol, Z=CH$_2$OH) catalyzed by PdCl$_2$(PPh$_3$)$_2$ and copper(I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) provides the corresponding alkynyl derivatives of formula N.1 (Z=CH$_2$OH). Saturation of the alkyne by hydrogenation catalyzed by palladium on carbon in alcoholic solvents affords alkyl derivatives of formula N.2 (Z=CH$_2$OH).

CHART M

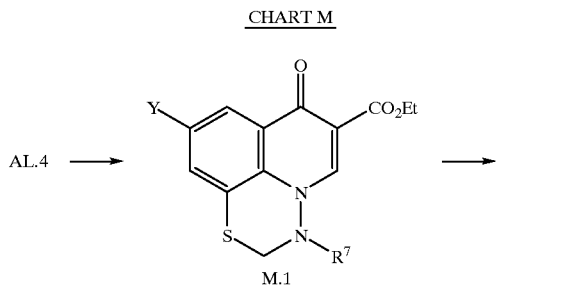

CHART N

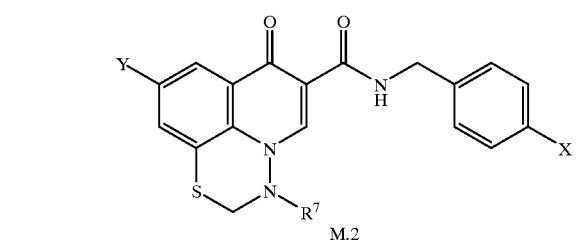

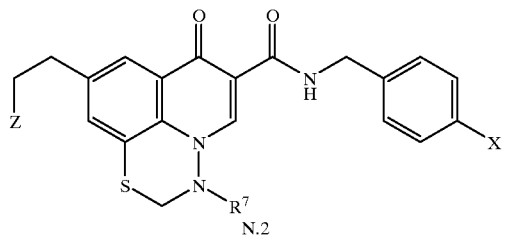

W1.7. 7-Oxo-7H-[1,4]thiazino[2,3,4-ij]quinoline-6-carboxamide. Representative examples of heterocycle W1.7 are prepared as described in Chart O in analogy to reported pyridobenzthiazino ring synthesis (Okada, T. et. al. *J. Heterocyclic Chem.* 1991, 28, 1067). The reaction of intermediate H.1 (Y=iodo, morpholinylmethyl, or tetrahydropyranylmethyl) with acetic anhydride and triethylorthoformate followed by condensation of the resulting enol ether with an allylic amine (e.g. 3-amino-1-butene, Roberts, J. D.; Mazur, R. H. *J. Am. Chem. Soc.* 1951, 73, 2509) affords the enamine of formula O.1. Cyclization of O.1 in the presence of a base (e.g. sodium hydride) provides quinolones of the formula O.2. Subsequent ozonolysis affords the carboxaldehyde O.3 which upon treatment with sodium hydrosulfide in DMF provides the tricycle O.4. Treatment of O.4 with thionylchloride followed by lithium chloride promoted elimination at elevated temperatures affords O.5. The resulting ester is saponified under dilute acid conditions and coupled with a benzylamine (e.g. 4-chlorobenzylamine) mediated by 1,1'-carbonyldiimidazole (or other suitable carboxylic acid activating agent) to provide amides of the general formula O.7. In the case where Y=iodo, compounds of the general formula O.7 are further derivatized as described in Chart P. Sonogashira coupling between O.7 (Y=iodo) and an electron-rich acetylene (e.g. propargyl alcohol, Z=CH$_2$OH) catalyzed by PdCl$_2$(PPh$_3$)$_2$ and copper(I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) provides the corresponding alkynyl derivatives of formula P.1 (Z=CH$_2$OH). Saturation of the alkyne by hydrogenation catalyzed by palladium on carbon in alcoholic solvents affords alkyl derivatives of formula P.2 (Z=CH$_2$OH).

CHART O

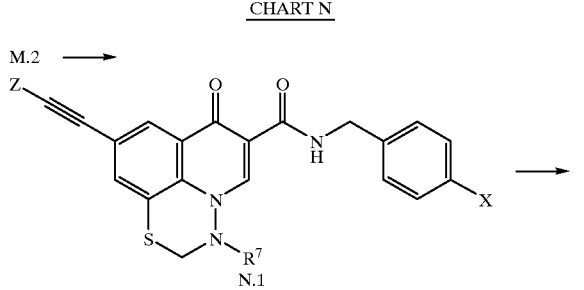

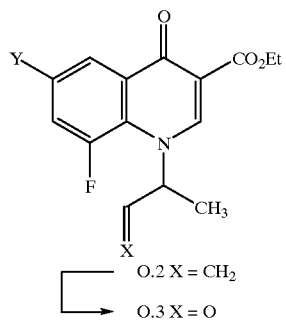

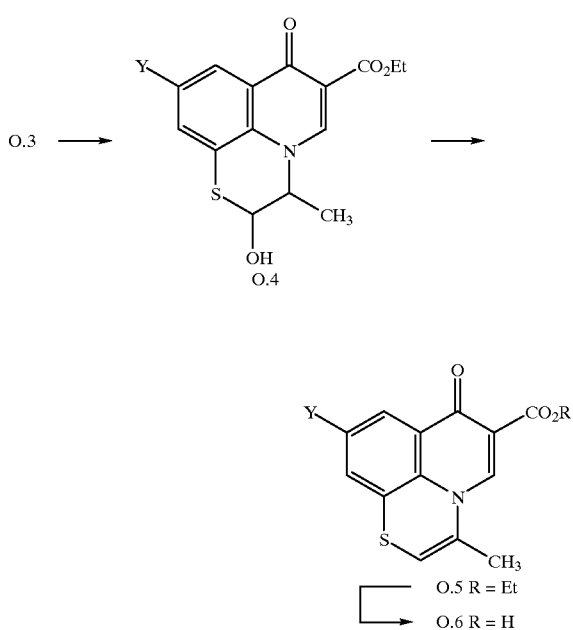

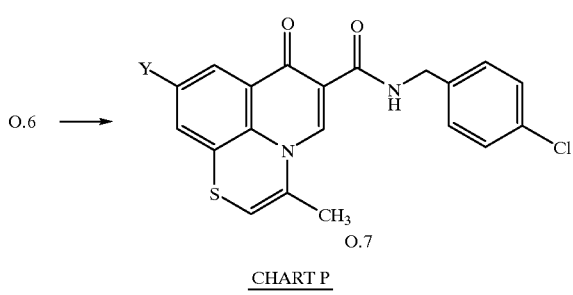

CHART P

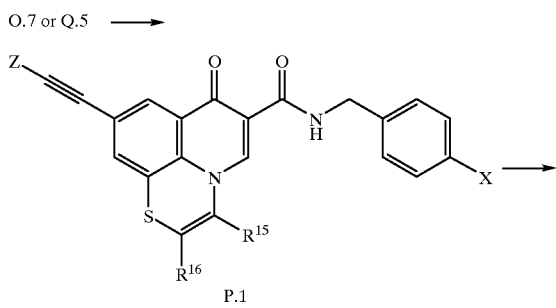

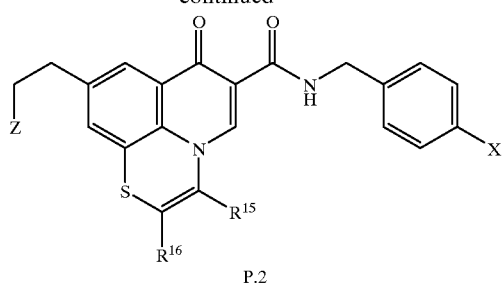

Additional examples of heterocycle W1.7 are prepared as described in Chart Q. 4-Iodo-2-fluoroaniline (Q.1) is condensed with diethyl ethoxymethylenemalonate under thermal conditions to provide 4-hydroxyquinoline Q.2. The resulting ester is converted to the corresponding amide of the formula Q.3 by either heating with a substituted benzylamine (e.g. 4-chlorobenzylamine), or by saponification of the ester to the acid, activation of the acid using a suitable agent (e.g. 1,1'-carbonyldiimidazole), and condensation with the above substituted benzylamine. The hydroxyquinolines are then reacted with an α-bromo ketones to afford compounds of the formula Q.4 (R is a subset of $R^{15}$ including optionally substituted alkyl or cycloalkyl, aryl, or het). The resulting ketones are treated with sodium hydrosulfide in DMF to afford compounds of the formula Q.5 directly, or in cases where elimination is not spontaneous, the intermediate alcohol is transformed as described above in Chart O. Intermediate Q.5 is transformed to the corresponding derivatives where G is optionally unsaturated $C_{1-4}$alkyl substituted by hydroxy in a manner analogous to that previously described in Chart P (P.1, P.2). Alternatively, Q.5 is formylated employing carbon monoxide, a palladium catalyst, and an appropriate reducing agent to provide carboxaldehydes of the formula Q.6. Subsequent reductive amination between Q.6 and a primary or secondary amine (e.g. morpholine) affords compounds of the formula Q.7.

CHART Q

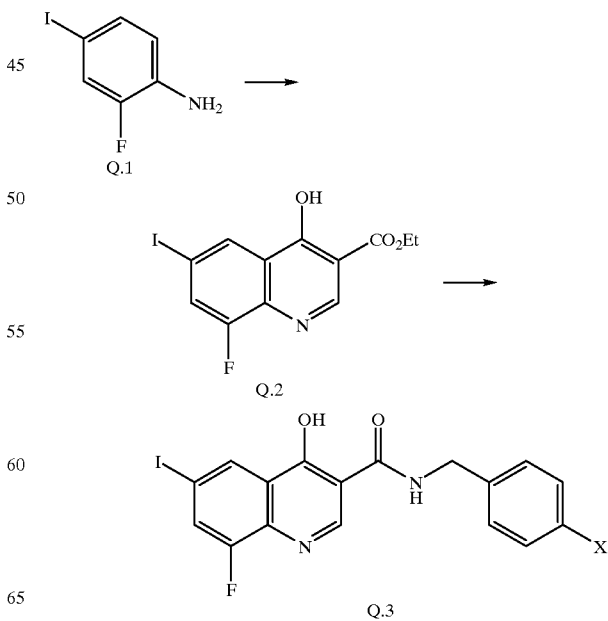

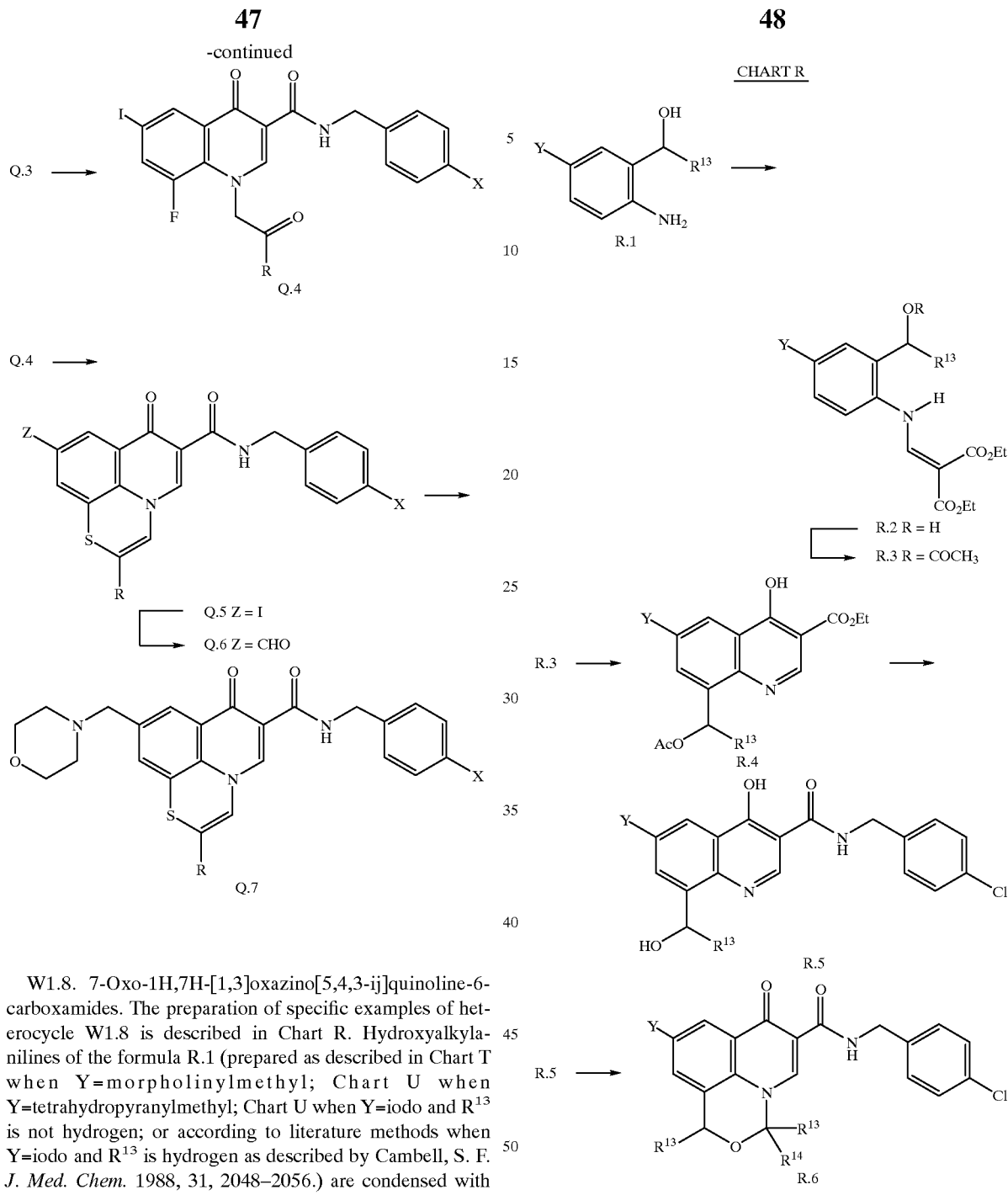

CHART R

W1.8. 7-Oxo-1H,7H-[1,3]oxazino[5,4,3-ij]quinoline-6-carboxamides. The preparation of specific examples of heterocycle W1.8 is described in Chart R. Hydroxyalkylanilines of the formula R.1 (prepared as described in Chart T when Y=morpholinylmethyl; Chart U when Y=tetrahydropyranylmethyl; Chart U when Y=iodo and $R^{13}$ is not hydrogen; or according to literature methods when Y=iodo and $R^{13}$ is hydrogen as described by Cambell, S. F. *J. Med. Chem.* 1988, 31, 2048–2056.) are condensed with diethyl ethoxymethylenemalonate to provide the corresponding enamine R.2. Acylation of the hydroxyl group employing the conditions of Tani, J. et.al. *Chem. Pharm. Bull.* 1982, 30, 3517. affords malonate R.3. Cyclization of R.3 under thermal conditions or in a mixture of Eaton's reagent affords quinoline derivatives of the formula R.4. The resulting ester is then heated with a benzylamine (e.g. 4-chlorobenzylamine) to afford a corresponding carboxamide such as R.5. Treatment of R.5 with an acetal or ketal and p-toluenesulfonic acid in N-methylpyrrolidinone as solvent (EP 373,531) affords tricycles of the formula R.6. Compounds of formula R.5 react with 1,1'-carbonyldiimidazole in DMF to give the 3,7-dioxo-1H,7H-[1,3]oxazino[5,4,3-ij] quinolines of structure R.6 ($R^{13}$ and $R^{14}$=O).

In the case where Y=iodo, the intermediate R.6 is further elaborated as described in Chart S by Sonogashira coupling with an electron-rich acetylene (e.g. propargyl alcohol, Z=CH$_2$OH) catalyzed by PdCl$_2$(PPh$_3$)$_2$ and copper(I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) to provide the corresponding alkynyl derivatives of formula S.1 (Z=CH$_2$OH). Saturation of the alkyne by hydrogenation catalyzed by palladium on carbon in alcoholic solvents affords alkyl derivatives of formula S.2 (Z=CH$_2$OH).

CHART S

R.6 →

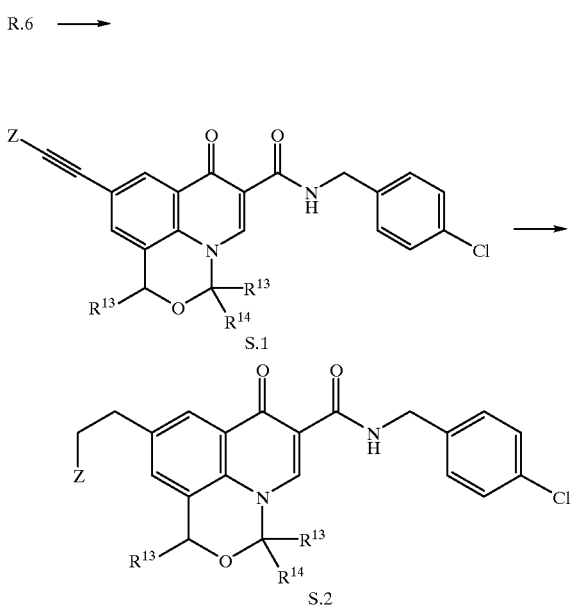

R.1 (Y=morpholinylmethyl) is prepared as described in Chart T. Methyl 3-bromomethyl-6-nitrobenzoate T.1 (*Bioorg. Med. Chem. Lett.* 1997, 7, 1921.) is treated with morpholine to afford the N-benzylmorpholine T.2. Reduction of the nitro functionality with tin(II) chloride provides the aniline T.3 which is further reduced with diisobutyl aluminum hydride to afford R.1 (Y=morpholinylmethyl, $R^{13}$=hydrogen). To prepare compounds in which $R^{13}$ is other than hydrogen, this material can be further elaborated by manganese dioxide oxidation (*J. Heterocyclic Chem.* 1993, 30, 1533; *J. Med. Chem.* 1988, 31, 2048) to afford the corresponding carboxaldehyde T.4. The reaction of T.4 with alkyl- or aryllithium and Grignard reagents (e.g. phenyl magnesium bromide) (*Aust. J. Chem.* 1992, 45, 21.) provides hydroxyanilines R.1 (Y=morpholinylmethyl, $R^{13}$= optionally substituted alkyl, aryl, or het).

R.1 (Y=tetrahydropyranylmethyl) is prepared as described in Chart U. Wittig olefination between 3-methylcarboxylate4-nitrobenzaldehyde U.1 (*J. Med. Chem.* 1988, 41, 1476.) and 4-tetrahydropyranylphosphonium bromide (Bestmann, H. J.; Stransky, W.; Vostrowsky, O. *Chem. Ber.* 1979, 109, 1694–1700.) employing sodium hexamethyldisilazide as base provides the olefin U.2. Hydrogenation of U.2 catalyzed by palladium on carbon provides the aniline U.3 which is further reduced with diisobutyl aluminum hydride to afford R.1 (Y=tetrahydropyranylmethyl, $R^{13}$=hydrogen). To prepare compounds in which $R^{13}$ is other than hydrogen, this material can be further elaborated as above by manganese dioxide oxidation to afford the corresponding carboxaldehyde U.4. The reaction of U.4 with alkyl- or aryllithium and Grignard reagents (e.g. phenyl magnesium bromide) provides hydroxyanilines R.1 (Y=tetrahydropyranylmethyl, $R^{13}$=optionally substituted alkyl, aryl, or het).

CHART X

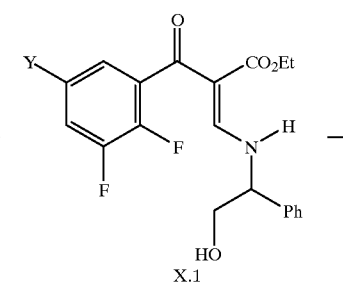
H.1 →

X.1

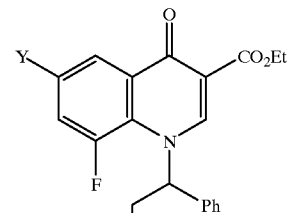

X.2 Z = OH
X.3 Z = Br

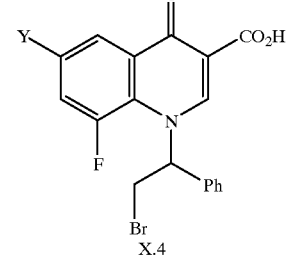
X.3 →

X.4

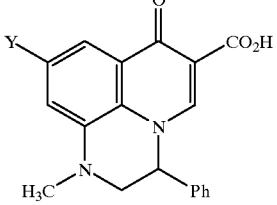
X.4 →

X.5

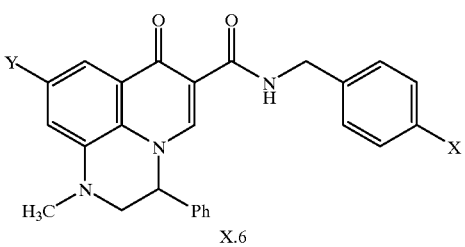

X.6

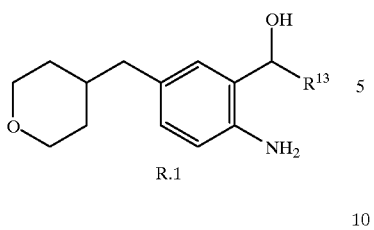
R.1

R.1 (Y=iodo, $R^{13}$=optionally substituted alkyl, aryl, or het) is prepared as described in Chart V. 2-Hydroxymethyl-4-iodoaniline (R.1, Y=iodo, $R^{13}$=hydrogen) (Cambell, S. F. *J. Med. Chem.* 1988, 31, 2048–2056.) is oxidized with manganese dioxide to afford the corresponding carboxaldehyde V.1. The reaction of U.4 with alkyl- or aryl-Grignard reagents (e.g. phenyl magnesium bromide) provides hydroxyanilines R.1 (Y=iodo, $R^{13}$=optionally substituted alkyl, aryl, or het).

CHART V

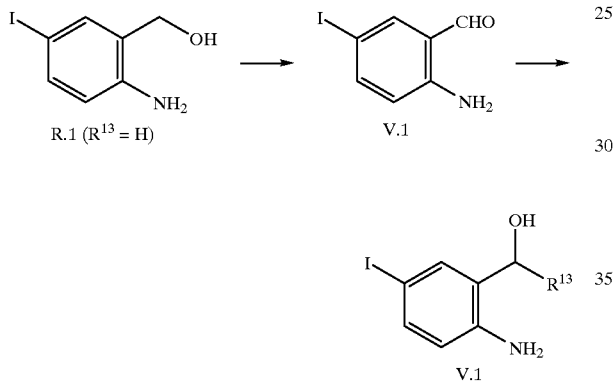

W1.9. 7-Oxo-2,3-dihydro-1H,7H-pyrido[1,2,3-de] quinoxaline-6-carboxamides. The preparation of specific examples of heterocycle W1.9 is described in Chart X following an established literature precedent (*Chem. Pharm. Bull.* 1994, 42, 2569.). Reaction of β-ketoesters of the formula H.1 (prepared as described in Chart I, where Y=iodo; Chart J, where Y=morpholinylmethyl; and Chart K, where Y=4-tetrahydropyranylmethyl) with acetic anhydride and triethylorthoformate followed by treatment of the resulting enol ether with an β-aminoalcohol (e.g. 2-aminophenylethanol, Y=phenyl) affords derivatives of the general formula X.1. Cyclization of X.1 in the presence of a sodium carbonate employing N,N-dimethylformamide as solvent provides quinoline X.2. Bromination of the resulting alcohol employing carbon tetrabromide and triphenylphosphine provides alkyl bromide X.3. Hydrolysis of the ester under acidic conditions followed by treatment of the resulting acid X.4 with a primary amine (e.g. methylamine) affords the quinoline X.5. The carboxylic acid is then coupled with a benzylamine (e.g. 4-chlorobenzylamine) mediated by 1,1'-carbonyldiimidazole (or other suitable carboxylic acid activating agent) to provide amides of the general formula X.6.

To prepare derivatives where G=3-hydroxypropyl or 3-hydroxy-1-propynyl, intermediate X.6 is further derivatized as in Chart Y by Sonogashira coupling with an electron-rich acetylene (e.g. propargyl alcohol, Z=$CH_2OH$) catalyzed by $PdCl_2(PPh_3)_2$ and copper(I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) to provide the corresponding alkynyl derivatives of formula Y.1 (Z=$CH_2OH$). Saturation of the alkyne by hydrogenation catalyzed by palladium on carbon in alcoholic solvents affords alkyl derivatives of formula Y.2 (Z=CH₂OH).

CHART Y

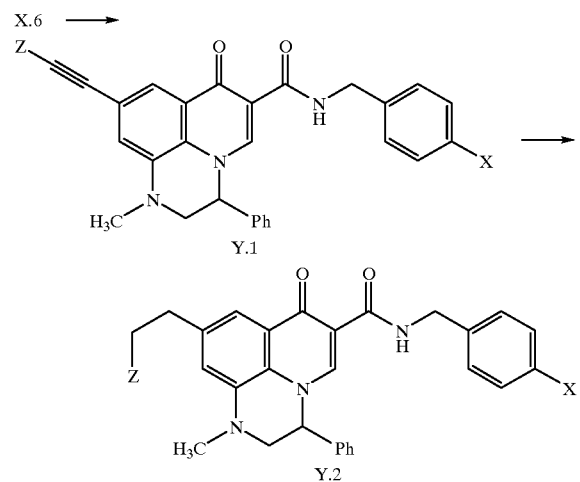

The preparation of other specific examples of heterocycles W1.9 are shown in Charts Y-AD. Compounds of the formula Z.1 (prepared as in Chart AA where Y=morpholinylmethyl; Chart AB where Y=3-hydroxypropyl or 3-hydroxy-1-propynyl) react with oxalyl chloride to afford 2,3,7-trioxo-2,3-dihydro-1H,7H-pyrido[1,2,3-de]quinoxaline-6-carboxamides of the general formula Z.2.

CHART Z

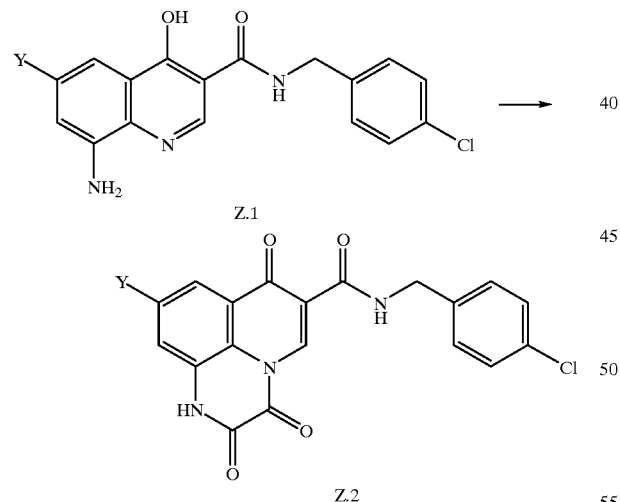

Z.1 (Y=morpholinylmethyl) is prepared as described in Chart AA. 2-Nitro-4-methylaniline (AA.1) is heated with diethyl ethoxymethylenemalonate to afford enamine AA.2 which is cyclized by refluxing in Dowtherm A to give 3-quinolinecarboxylate AA.3 (Peet, N. P. *J. Med. Chem.* 1985, 28, 298–302). Ester AA.3 is reacted with N-bromosuccinimide in 1,2-dichloroethane to give alkyl bromide AA.4. The crude reaction product is treated with morpholine to give AA.5 which is reduced by hydrogenation over palladium on carbon catalyst to provide AA.6. The resulting ester is reacted with a substituted benzylamine (e.g. 4-chlorobenzylamine, 4-fluorobenzylamine, or 4-bromobenzylamine) to give amides of the formula Z.1 (Y=morpholinylmethyl) which may be employed as described in Chart Z.

Z.1 (Y=3-hydroxypropyl and 3-hydroxy-1-propynyl) is prepared as described in Chart AB. Sonogashira coupling of A.2 with an electron-rich acetylene (e.g. propargyl alcohol, Z=CH₂OH) provides the alkynyl-substituted quinoline AB.1. Stannous chloride reduction of the nitro group provides the aminoquinoline Z.1. (Y=3-hydroxy-1-propynyl, Z=CH₂OH). Saturation of the alkyne by hydrogenation catalyzed by palladium on carbon in alcoholic solvents affords alkyl derivatives of formula Z.1 (Y=3-hydroxypropyl, Z=CH₂OH).

CHART AA

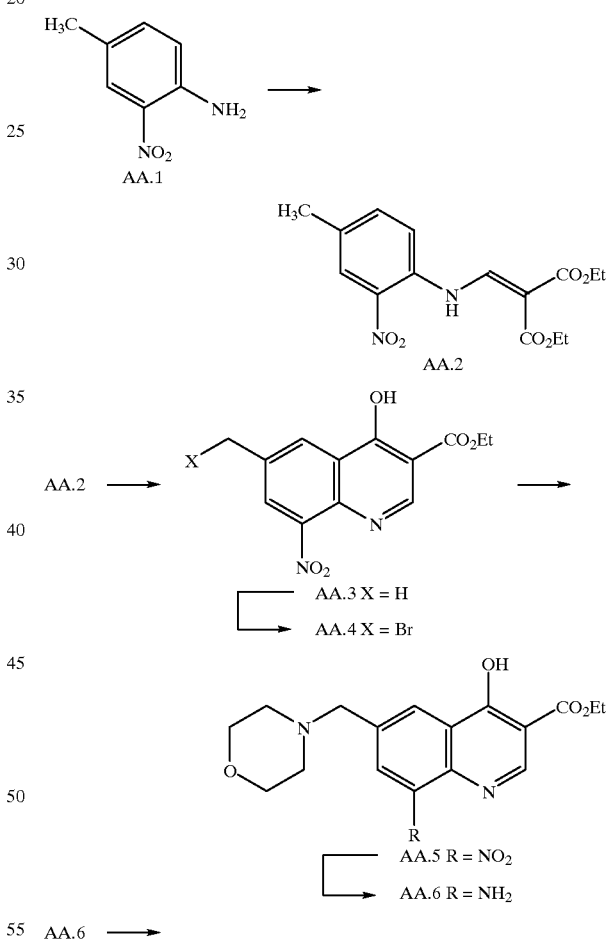

AA.6 ⟶

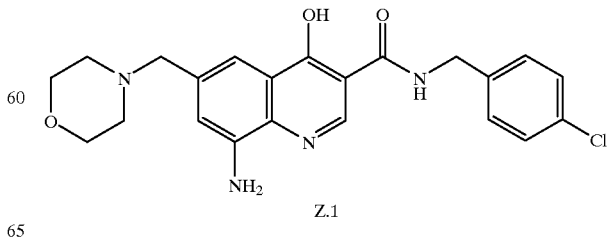

CHART AB

A.2 →

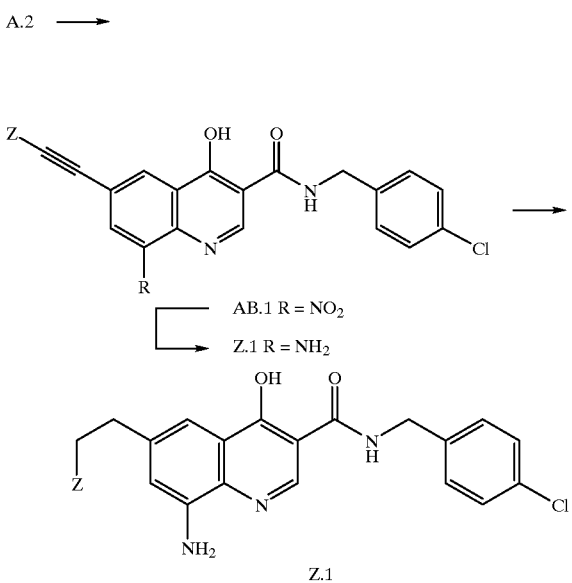

AB.1 R = NO$_2$
Z.1 R = NH$_2$

Alternatively, compounds of the formula Z.1 (Y=morpholinylmethyl, 3-hydroxypropyl, and 3-hydroxy-1-propynyl) react with bromoacetic anhydride (R=H) or 2-bromoalkanoyl bromides (e.g. 2-bromopropionyl bromide, R=methyl) to give tricyclic compounds of the formula AC.1, Chart AC. Likewise, compounds of the formula Z.1 (Y=morpholinylmethyl, 3-hydroxypropyl, and 3-hydroxy-1-propynyl) react with ethyl bromoacetate to afford 3,7-dioxo-2,3-dihydro-1H,7H-pyrido[1,2,3-de] quinoxaline-6-carboxamides according to the general formula AD.1, Chart AD.

CHART AC

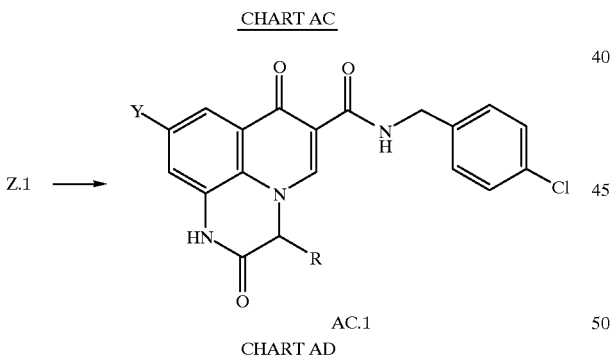

Z.1 →

AC.1

CHART AD

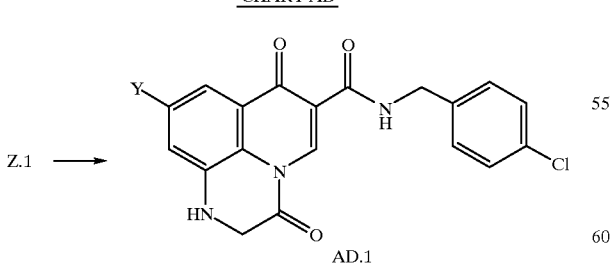

Z.1 →

AD.1

Additional examples of heterocycle W1.9. are prepared as described in Chart AE. The previously described β-ketoester H.1 is reacted with triethyl orthoformate in refluxing acetic anhydride to provide enol ether AE.1, which is further reacted with a mono-tert-butyloxycarbonyl protected ethyl-enediamine derivitive (where R is defined according to $R^{13}$) to afford compounds of the formula AE.2. Treatment of AE.2 with cesium carbonate in DMF effects cyclization to afford tricycles of the formula AE.3. Palladium catalyzed carbonylation using carbon monoxide gas and tri-n-butylstannane provides carboxaldehyde AE.4, and subsequent reductive amination with morpholine and sodium triacetoxyborohydride affords compounds of the formula AE.5. Aminolysis of the resulting ester using a substituted benzylamine (e.g. 4-chlorobenzylamine, 4-fluorobenzylamine, or 4-bromobenzylamine) in methanol with catalytic sodium methoxide provides AE.6, which is converted to AE.7 on exposure to trifluoromethanesulfonic acid. The nitrogen of the quinoxaline ring in AE.7 may be alkylated, acylated, sulfonylated, etc. giving compounds of formula AE.8.

CHART AE

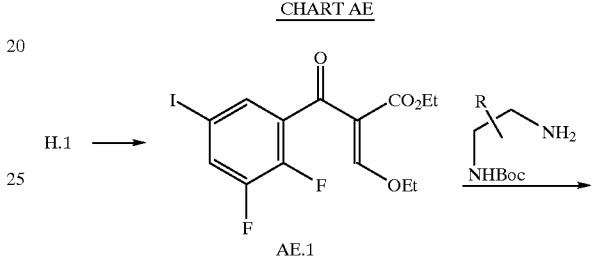

H.1 →

AE.1

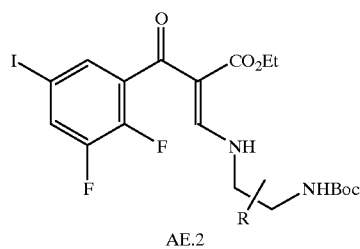

AE.2

AE.2 →

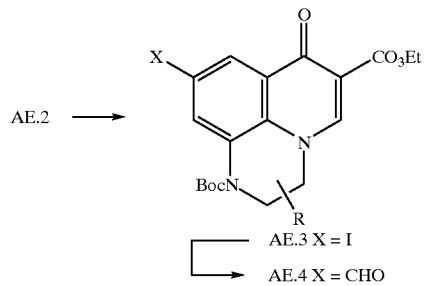

AE.3 X = I
AE.4 X = CHO

AE.4 →

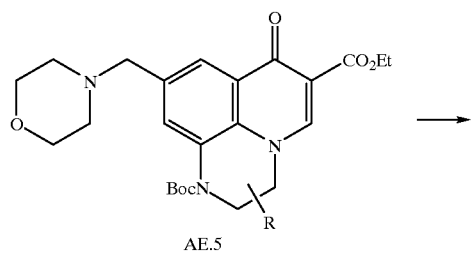

AE.5

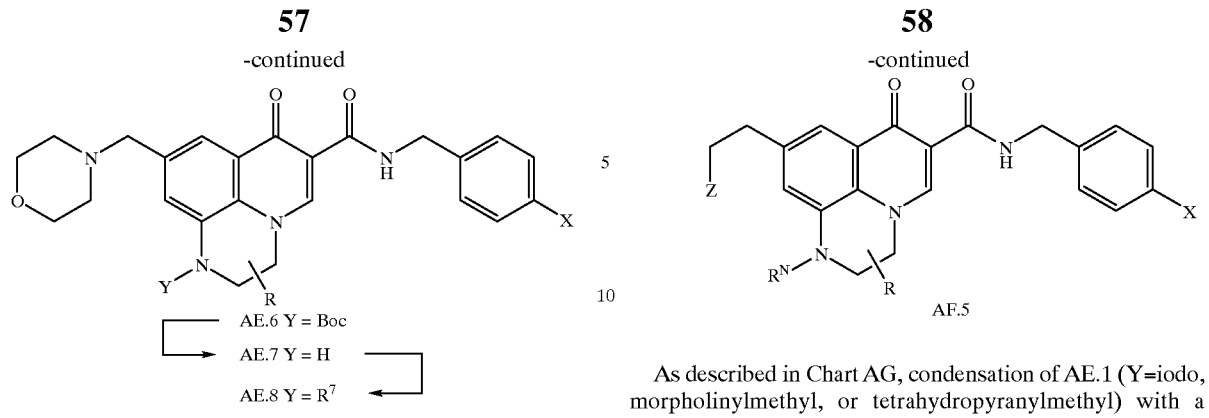

AE.6 Y = Boc
AE.7 Y = H
AE.8 Y = R[7]

Alternatively, esters of the formula AE.3 are reacted with a substituted benzylamine (e.g. 4-chlorobenzylamine, 4-fluorobenzylamine, or 4-bromobenzylamine) in methanol employing catalytic sodium methoxide to provide amides of the structure AF.1, which is converted to AF.2 on exposure to trifluoromethanesulfonic acid. The nitrogen of the quinoxaline ring in AF.2 may be alkylated, acylated, sulfonylated, etc. ($R^N$ as defined according to $R^7$) giving compounds of formula AF.3. Palladium catalyzed coupling of AF.3 with an electron-rich acetylene (e.g. propargyl alcohol, Z=CH$_2$OH) gives AF.4 (Sonogashira, K.; Tohada, Y.; Hagihara, N. *Tetrahedron Lett.* 1975, 50, 4467. or Fisher, M. J. et. al. *J. Med. Chem.* 1997, 40, 2085.). Saturation of the alkyne by hydrogenation catalyzed by palladium on carbon in alcoholic solvents affords alkyl derivatives of formula AF.5 (Z=CH$_2$OH).

As described in Chart AG, condensation of AE.1 (Y=iodo, morpholinylmethyl, or tetrahydropyranylmethyl) with a 2-aminoalkanoic amide (e.g. glycine methylamide) followed by treatment with a base such as sodium hydride provides compounds illustrated by formula AG.1. The resulting ester is treated with a benzylamine (e.g. 4-chlorobenzylamine) at high temperature to afford the corresponding carboxamides of the general formula AG.2. In the case where Y=iodo, AG.2 is further derivatived as in Chart AH employing a Sonogashira coupling with an electron-rich acetylene (e.g. propargyl alcohol, Z=CH$_2$OH) gives AH.1. Saturation of the alkyne by hydrogenation catalyzed by palladium on carbon in alcoholic solvents affords alkyl derivatives of formula AF.5 (Z=CH$_2$OH).

CHART AF

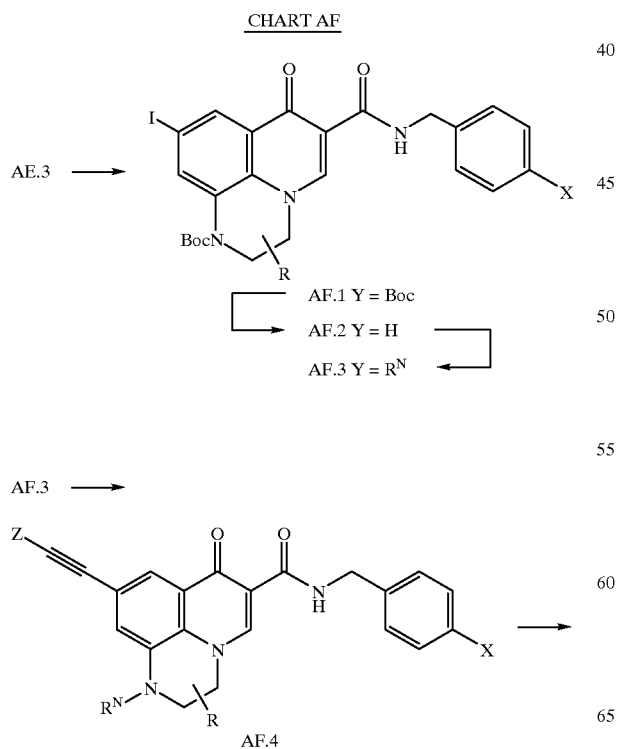

AF.1 Y = Boc
AF.2 Y = H
AF.3 Y = R[N]

CHART AG

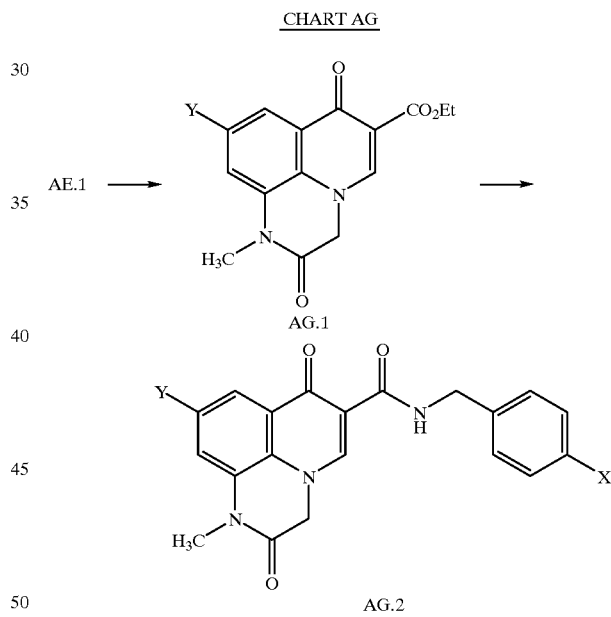

CHART AH

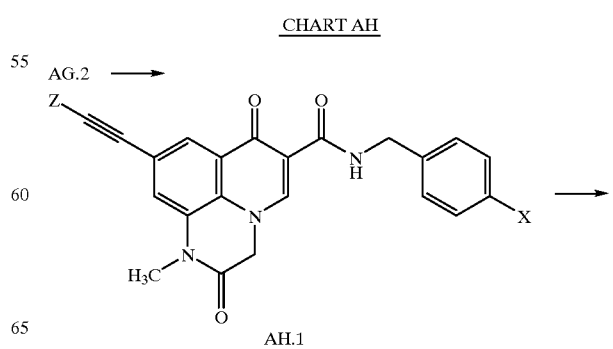

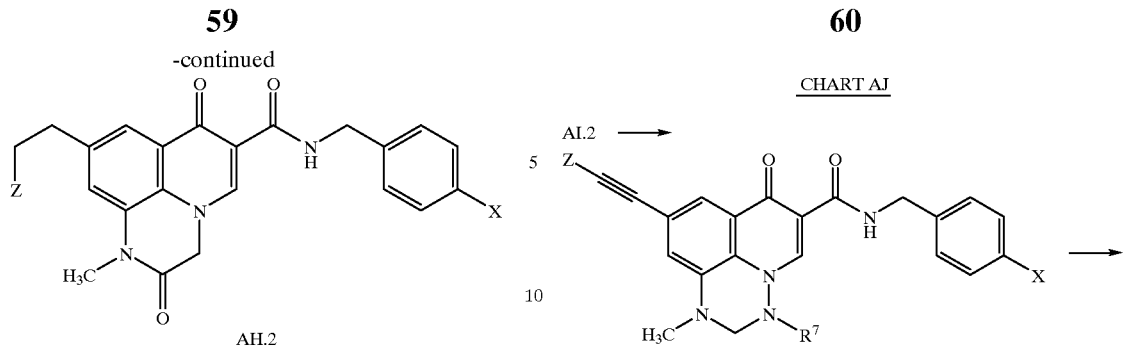

AH.2

W1.10. 7-Oxo-2,3-dihydro-1H,7H-[1,2,4]triazino[5,6,1-ij]quinoline-6-carboxamides. The preparation of specific examples of heterocycle W1.10 is described in Chart AI following an established literature precedent (*Bull Chem. Soc. Jpn.* 1996, 69, 1371–1376.). Alcohol AM.4 (Y=morpholinylmethyl, tetrahydropyranylmethyl, or iodo) is treated with thionyl chloride followed by a primary amine to afford quinoline AI.1. The resulting ester is then treated with a benzylamine (e.g. 4-chlorobenzylamine, 4-bromobenzylamine, or 4-fluorobenzylamine) at high temperature to afford the corresponding amides of the general formula AI.2 Specific examples where G=3-hydroxypropyl or 3-hydroxy-1-propynyl are prepared as described in Chart AJ from intermediate AI.2 (Y=iodo) by Sonogashira coupling with an electron-rich acetylene (e.g. propargyl alcohol, Z=CH$_2$OH) catalyzed by PdCl$_2$(PPh$_3$)$_2$ and copper(I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) provides the corresponding alkynyl derivatives of formula AJ.1 (Z=CH$_2$OH). Saturation of the alkyne by hydrogenation catalyzed by palladium on carbon in alcoholic solvents affords alkyl derivatives of formula AJ.2 (Z=CH$_2$OH).

CHART AI

W1.11. 2,7-Dioxo-2,3-dihydro-1H,7H-pyrido[3,2,1-ij]cinnoline-8-carboxamides. The preparation of specific examples of heterocycle W1.11 is described in Chart AK following an established literature precedent (*Tetrahedron* 1995, 51, 11125–11140). Intermediates of the formula AM.3 (Y=iodo, morpholinylmethyl, or tetrahydropyranylmethyl) are saponified under basic conditions and the resulting carboxylic acid is coupled with a substituted benzylamine (e.g. 4-chlorobenzylamine) promoted by 1,1'-carbonyldiimidazole (or another appropriate carboxylic acid activating agent) to provide carboxamides of the general formula AK.1. The resulting carboxamides are treated with 1,3-bis(trimethylsilyl)urea and ethyl malonyl chloride to afford AK.2. Subsequent heating of a DMSO solution of AK.2 in the presence of Cs$_2$CO$_3$ affords the pyridocinnoline AK.3. Hydrolysis and decarboxylation of AK.3 is accomplished by heating AK.2 in a mixture of hydrochloric and acetic acid to afford compounds of the formula AK.4. In the case where Y=iodo, the intermediate AK.4 is further elaborated as described in Chart AL by Sonogashira coupling with an electron-rich acetylene (e.g. propargyl alcohol, Z=CH$_2$OH) catalyzed by PdCl$_2$(PPh$_3$)$_2$ and copper(I) iodide in a mixture of DMF and triethylamine (Fisher, M. J. et. al. *J. Med. Chem.* 1997, 40, 2085.) to provide the corresponding alkynyl derivatives of formula AL.1 (Z=CH$_2$OH). Saturation of the alkyne by hydrogenation catalyzed by palladium on carbon in alcoholic solvents affords alkyl derivatives of formula AL.2 (Z=CH$_2$OH).

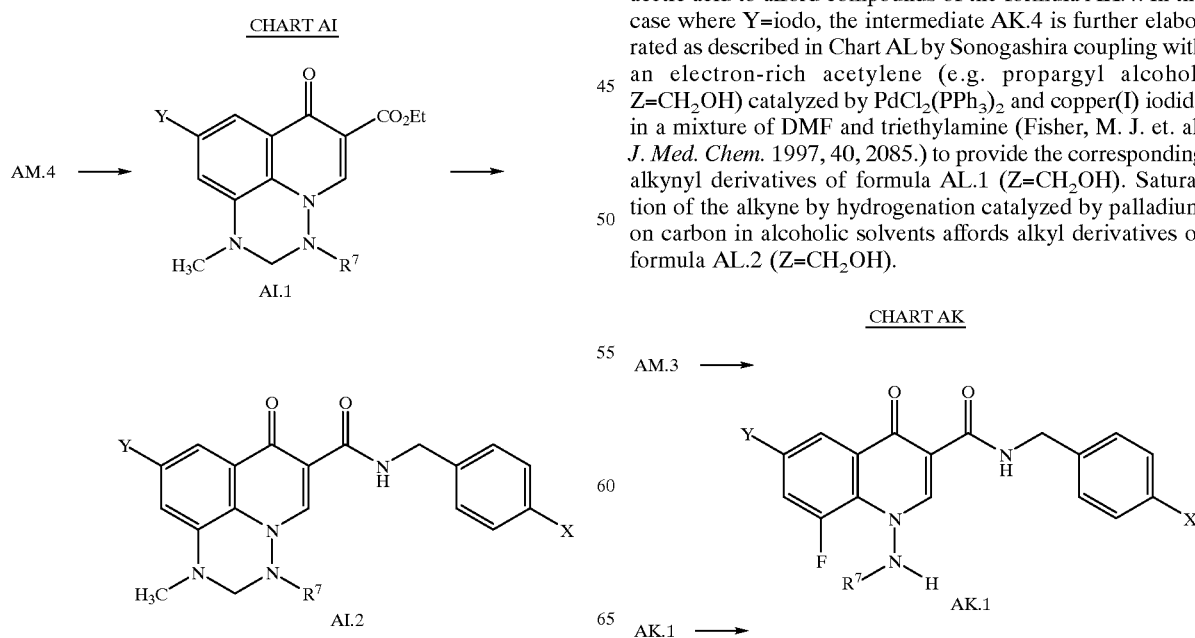

CHART AK

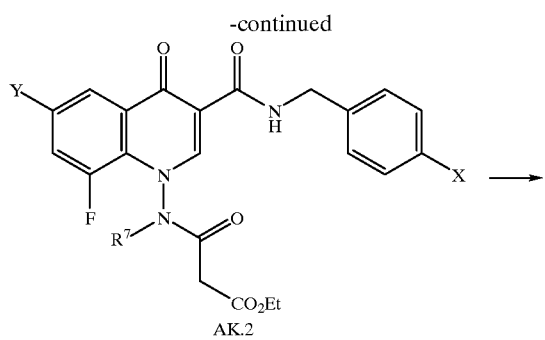

AK.2

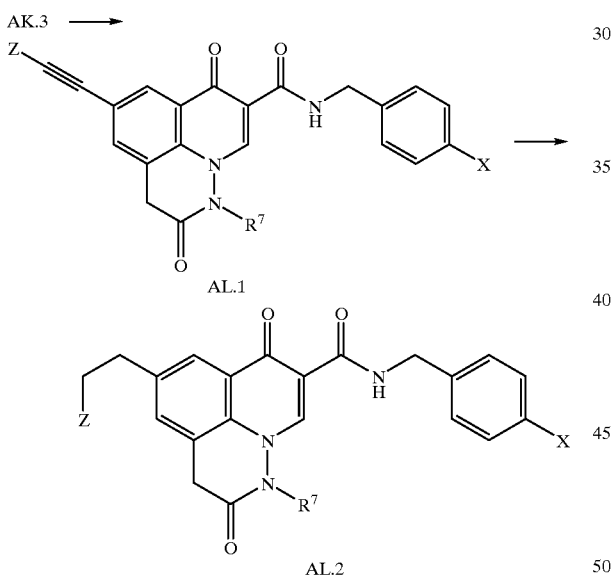

AK.3 Z = CO₂Et
AK.4 Z = H

CHART AL

AK.3 →

AL.1

AL.2

Other representative examples of heterocycle W1.11 are prepared as described in Chart AM. Ketoester H.1 (Y=iodo, morpholinylmethyl, or tetrahydropyranylmethyl) is condensed with a Boc-protected hydrazine (e.g. tert-butyl 1-methylhydrazinecarboxylate, $R^7$=methyl, prepared as described by Oliva, G. A. et. al. *J. Heterocyclic Chem.* 2000, 37, 47) to provide derivatives of the formula AM.1. Cyclization of AM.1 in the presence of a base (e.g. sodium hydride) affords quinolones of the general formula AM.2 which are subsequently deprotected using common synthetic methods (Green, T. W.; Wuts, P. G. M. *Protective Groups in Organic Synthesis,* 1999) to provide AM.3. Condensation of AM.3 with formaldehyde provides AM.4. Conversion of the hydroxyl group to an appropriate leaving group such as the chloride upon treatment with thionyl chloride and then subsequent displacement with a malonate diester anion affords quinolone malonates of the formula AM.5. Cyclization of AM.5 by heating in the presence of an inorganic base (e.g. cesium carbonate) provides AM.6. Hydrolysis and decarboxylation of AM.6 is accomplished by initially heating in the presence of an acid (e.g. acetic acid or trifluoroacetic acid) followed by further decarboxylation by heating a DMSO solution to 135–165° C. resulting in compounds of the formula AM.7. The resulting carboxylic acid is then coupled with a benzylamine (e.g. 4-chlorobenzylamine) mediated by an appropriate acid activating reagent (e.g. 1,1'-carbonyldiimidazole) to afford carboxamides of the formula AM.8. In the case where Y=iodo, the intermediate AM.8 is further elaborated as described in Chart AN by Sonogashira coupling with an electron-rich acetylene (e.g. propargyl alcohol, Z=CH₂OH) catalyzed by PdCl₂(PPh₃)₂ and copper(I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) to provide the corresponding alkynyl derivatives of formula AN.1 (Z=CH₂OH). Saturation of the alkyne by hydrogenation catalyzed by palladium on carbon in alcoholic solvents affords alkyl derivatives of formula AN.2 (Z=CH₂OH).

CHART AM

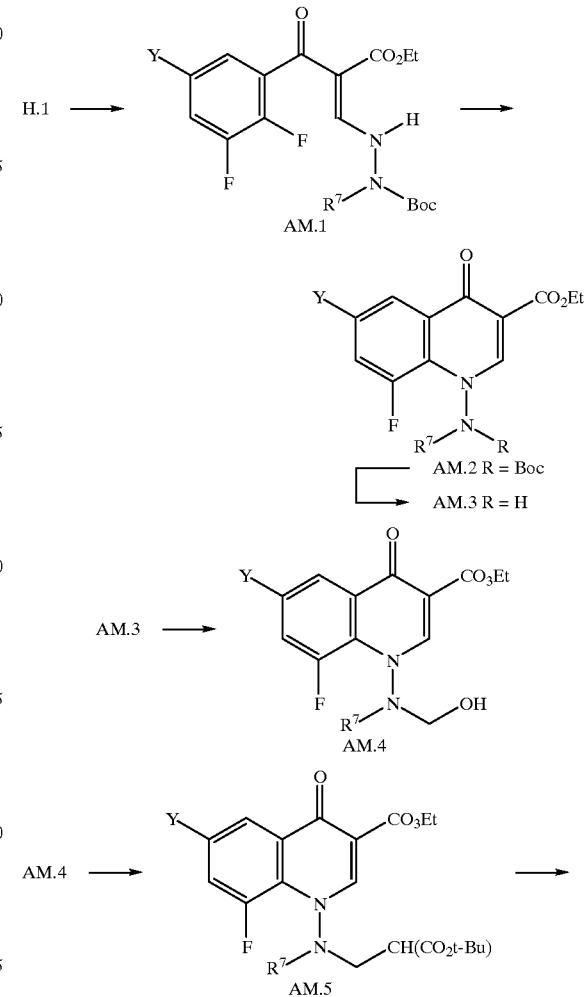

AM.1

AM.2 R = Boc
AM.3 R = H

AM.3 →

AM.4

AM.4 →

AM.5

CHART AO

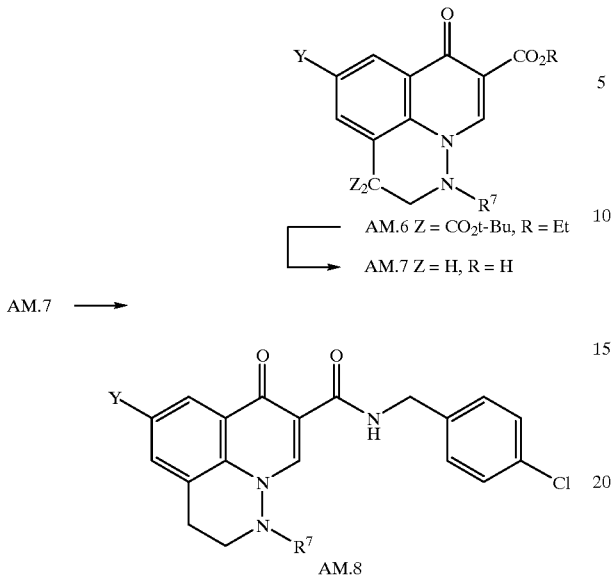

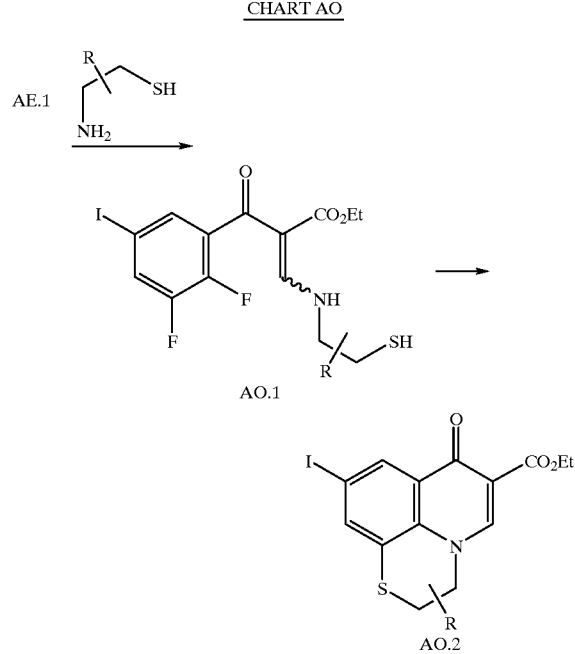

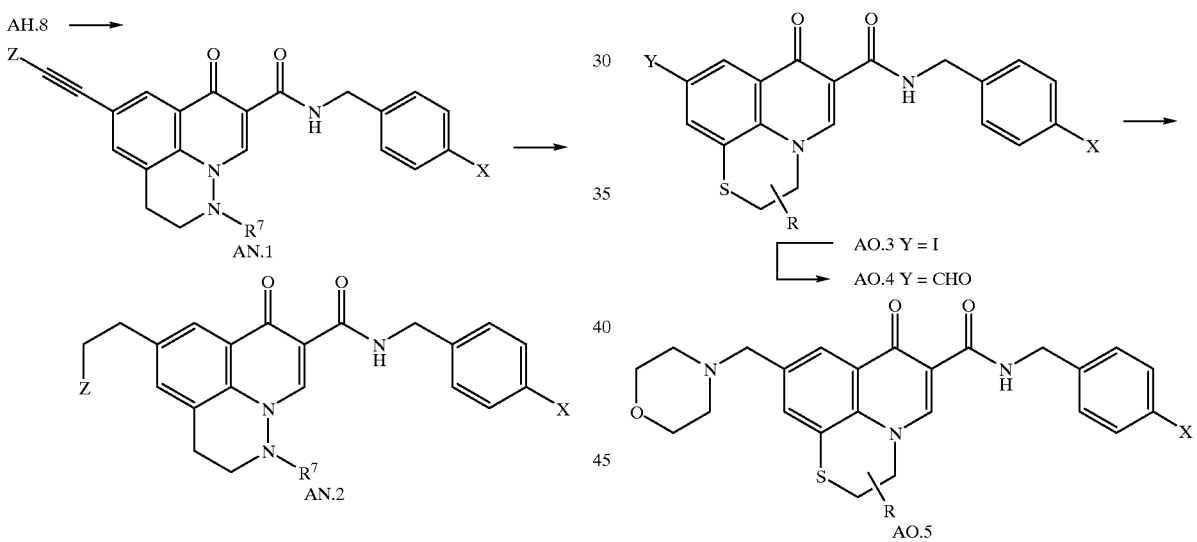

W1.13. 7-Oxo-2,3-dihydro-7H-[1,4]thiazino[2,3,4-ij] quinoline-6-carboxamides. Enol ether AE.1 is reacted with a 2-mercaptoethylamine derivative (where in R is defined according to $R^{13}$) to afford compounds of the formula AO.1 as a mixture of E/Z isomers. Treatment of AO.1 with cesium carbonate in DMF effects cyclization to benzthiazine AO.2. Aminolysis of the ethyl ester with a substituted benzylamine (e.g. 4-chlorobenzylamine, 4-fluorobenzylamine, or 4-bromobenzylamine) provides amides of the formula AO.3, which are reacted with carbon monoxide and tri-n-butylstannane under palladium catalysis to afford aldehydes of the formula AO.4. Reductive amination of the aldehyde using morpholine and sodium triacetoxyborohydride provides AO.5. Oxidation of the sulfur with meta-chloroperbenzoic acid affords derivatives of the formula AO.6 where n=1 (sulfoxide) or n=2 (sulfone).

Alternatively, amides of the formula AO.3 are reacted through palladium catalyzed coupling with of an electron-rich acetylene (e.g. propargyl alcohol, Z=CH$_2$OH) to give alkynes of the formula AP.1. Saturation of the alkyne by hydrogenation catalyzed by palladium on carbon in alcoholic solvents affords alkyl derivatives of formula AP.2 (Z=CH$_2$OH). Oxidation of the sulfur atom found in compounds AP.1 or AP.2 with meta-chloroperbenzoic acid affords sulfoxide (n=1) or sulfone (n=2) derivatives of the formulas AP.3 and AP.4, respectively.

CHART AP

AO.4 ⟶

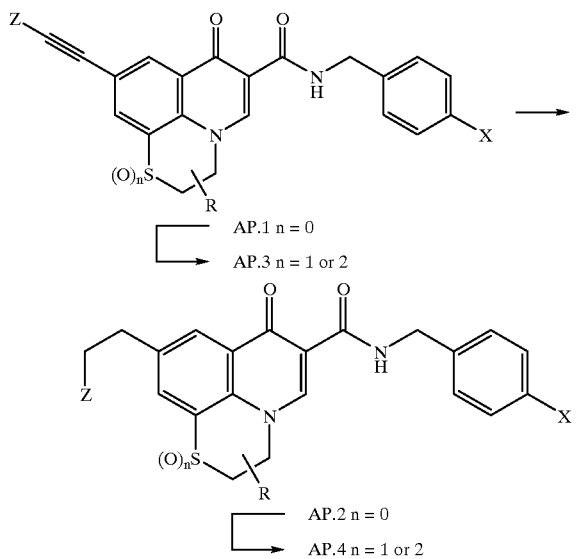

AP.1 n = 0
AP.3 n = 1 or 2

AP.2 n = 0
AP.4 n = 1 or 2

W1.14. 7-Oxo-1H,7H-[1,3]thiazino[5,4,3-ij]quinoline-6-carboxamides. The preparation of specific examples of heterocycle W1.14 is described in Chart AQ. Malonates of the formula R.2 (Y=morpholinylmethyl, tetrahydropyranylmethyl, or iodo) are converted to their corresponding thiolacetate AQ.1 by treatment with triphenylphosphine and diisopropyl azodicarboxylate in the presence of thiolacetic acid (Volante, R. P. *Tetrahedron Let.* 1981, 22, 3119–3122.). Cyclization of AQ.1 under thermal conditions or in a mixture of Eaton's reagent affords quinoline derivatives of the formula AQ.2. The resulting ester is then heated with a benzylamine (e.g. 4-chlorobenzylamine) to afford a corresponding carboxamide such as AQ.3. Treatment of AQ.3 with an acetal or ketal and p-toluenesulfonic acid in N-methylpyrrolidinone as solvent (EP 373,531) affords tricycles of the formula AQ.4.

CHART AQ

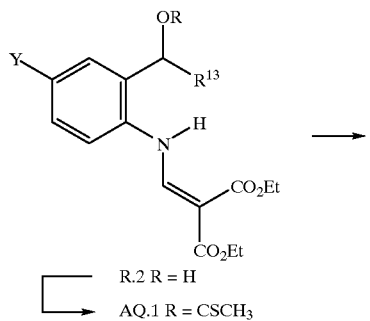

R.2 R = H
AQ.1 R = CSCH₃

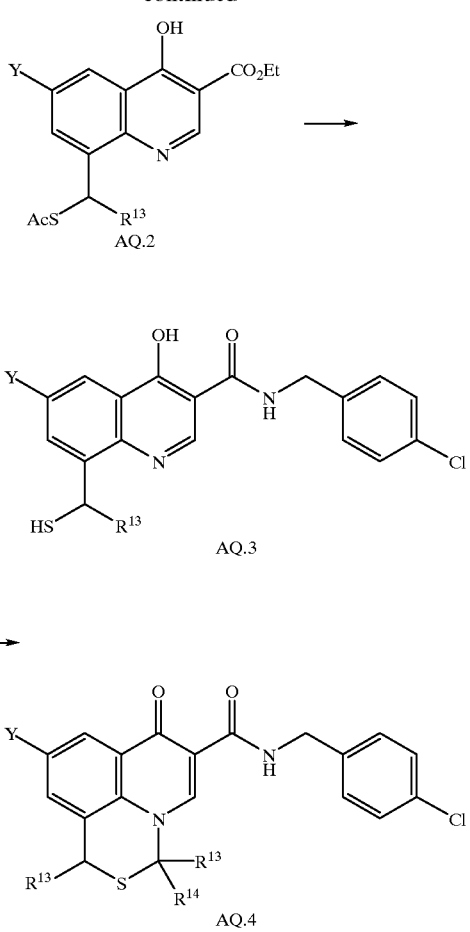

AQ.2

AQ.3

AQ.3 ⟶

AQ.4

In the case where Y=iodo, the intermediate AQ.4 is further elaborated as described in Chart AR by Sonogashira coupling with an electron-rich acetylene (e.g. propargyl alcohol, Z=CH₂OH) catalyzed by PdCl₂(PPh₃)₂ and copper (I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) to provide the corresponding alkynyl derivatives of formula AR.1 (Z=CH₂OH). Saturation of the alkyne by hydrogenation catalyzed by palladium on carbon in alcoholic solvents affords alkyl derivatives of formula AR.2 (Z=CH₂OH).

CHART AR

AQ.4 ⟶

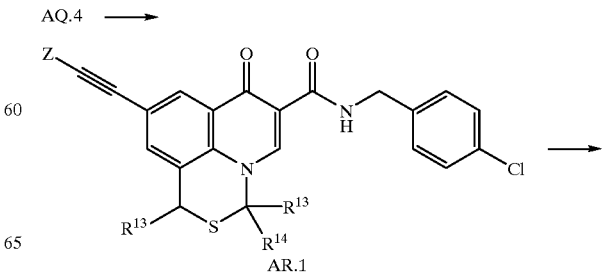

AR.1

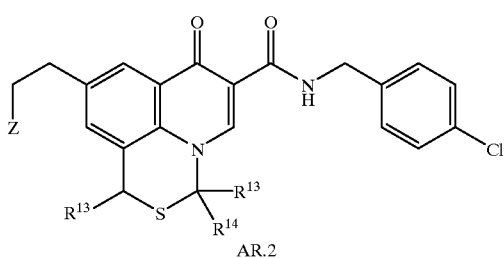

AR.2

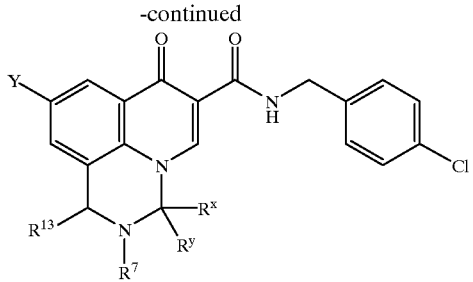

AS.5

W1.15. 7-Oxo-2,3-dihydro-1H,7H-pyrido[3,2,1-ij]quinazoline-6-carboxamides. The preparation of specific examples of heterocycle W1.15 is described in Chart AS. Alkylaminoanilines of the formula AS.1 (prepared as described in Chart AU when Y=morpholinylmethyl, tetrahydropyranylmethyl, or Y=iodo) are condensed with a variety of aldehydes and ketones (e.g. formaldehyde, $R^x=R^y=H$; benzaldehyde, $R^x$=phenyl, $R^y$=H) employing literature methods (Wagner, E. C.; Eisner, A. *J. Am. Chem. Soc.* 1937, 59, 879–883.; Kempter, G. et.al. *J. Prakt. Chem.* 1982, 324, 832–840.) to afford tetrahydroquinazolines of the formula AS.2. Condensation of AS.2 with diethyl ethoxymethylenemalonate provides the malonate derivatives AS.3 which are cyclized by heating in a mixture of Eaton's reagent to afford the substituted quinoline derivatives of the formula AS.4. The resulting ester is then heated with a benzylamine (e.g. 4-chlorobenzylamine) to afford a corresponding carboxamide such as AS.5.

CHART AS

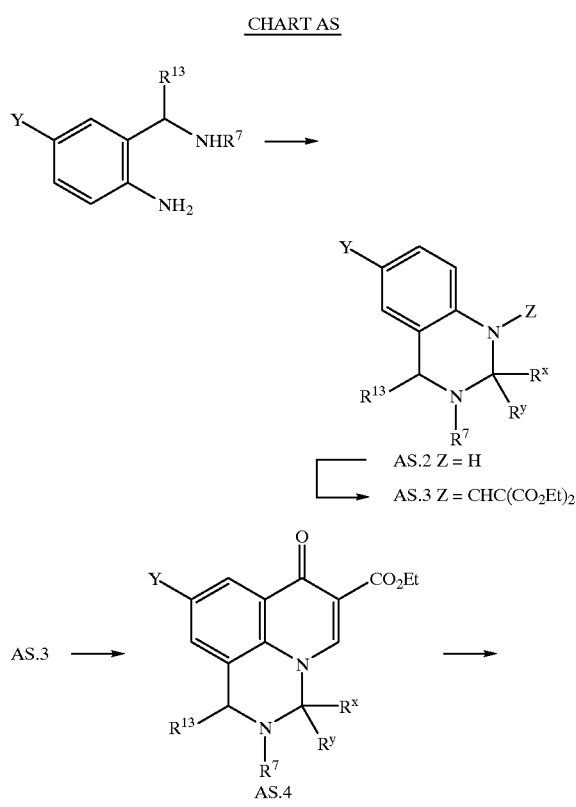

In the case where Y=iodo, the intermediate AS.5 is further elaborated as described in Chart AT by Sonogashira coupling with an electron-rich acetylene (e.g. propargyl alcohol, $Z=CH_2OH$) catalyzed by $PdCl_2(PPh_3)_2$ and copper(I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) to provide the corresponding alkynyl derivatives of formula AT.1 ($Z=CH_2OH$). Saturation of the alkyne by hydrogenation catalyzed by palladium on carbon in alcoholic solvents affords alkyl derivatives of formula AT.2 ($Z=CH_2OH$).

CHART AT

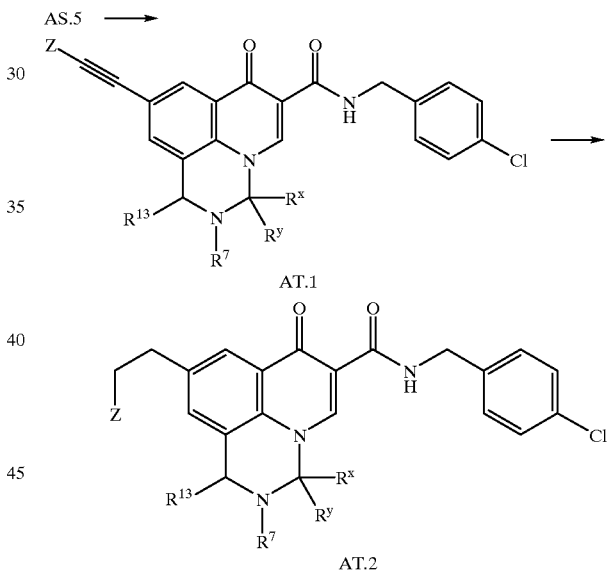

AS.1 is prepared as described in Chart AU. Hydroxyalkylamines R.1 where Y=morpholinylmethyl, tetrahydropyranylmethyl, or iodo (prepared as described previously in Charts N–P) are oxidized with manganese dioxide or other suitable oxidizing agent to afford the corresponding aldehyde or ketone AU.1. Compounds AU.1 are then converted to the amine derivatives AS.1 by a one step reductive amination employing a primary amine and sodium cyanoborohydride or in a two step sequence involving first formation of the imine by treatment with a primary amine and titanium tetrachloride and then reduction with lithium aluminum hydride (*Chem. Pharm. Bull.* 1981, 29, 2135.). Alternatively when $R^7$=aryl, compounds of the formula AS.1 ($R^z$=aryl) are prepared by a Mannich condensation with anilines AU.2 (Y=morpholinylmethyl, tetrahydropyranylmethyl, or iodo) employing procedures described in the literature (Wagner, E. C.; Eisner, A. *J. Am. Chem. Soc.* 1937, 59, 879–883.).

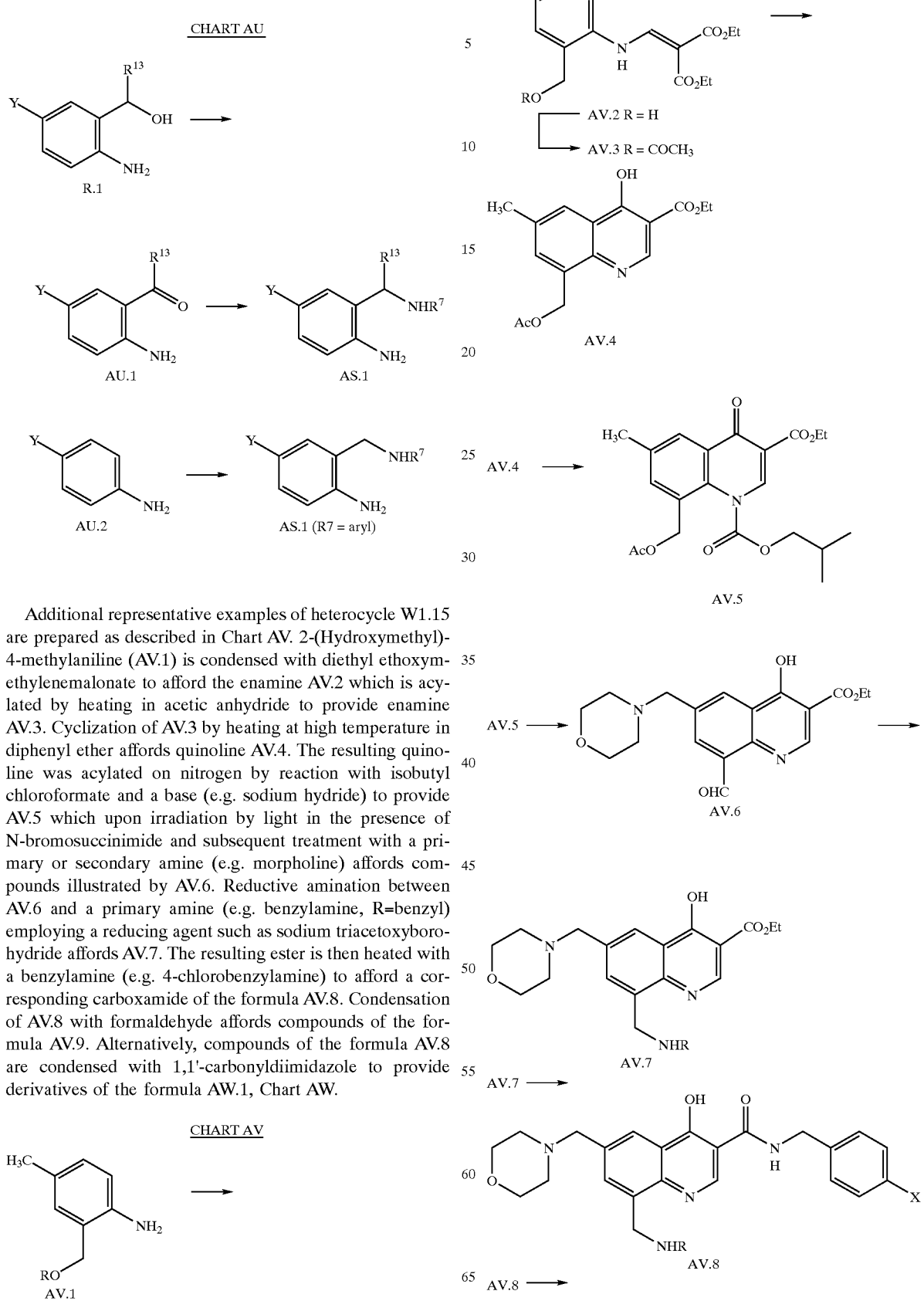

Additional representative examples of heterocycle W1.15 are prepared as described in Chart AV. 2-(Hydroxymethyl)-4-methylaniline (AV.1) is condensed with diethyl ethoxymethylenemalonate to afford the enamine AV.2 which is acylated by heating in acetic anhydride to provide enamine AV.3. Cyclization of AV.3 by heating at high temperature in diphenyl ether affords quinoline AV.4. The resulting quinoline was acylated on nitrogen by reaction with isobutyl chloroformate and a base (e.g. sodium hydride) to provide AV.5 which upon irradiation by light in the presence of N-bromosuccinimide and subsequent treatment with a primary or secondary amine (e.g. morpholine) affords compounds illustrated by AV.6. Reductive amination between AV.6 and a primary amine (e.g. benzylamine, R=benzyl) employing a reducing agent such as sodium triacetoxyborohydride affords AV.7. The resulting ester is then heated with a benzylamine (e.g. 4-chlorobenzylamine) to afford a corresponding carboxamide of the formula AV.8. Condensation of AV.8 with formaldehyde affords compounds of the formula AV.9. Alternatively, compounds of the formula AV.8 are condensed with 1,1'-carbonyldiimidazole to provide derivatives of the formula AW.1, Chart AW.

-continued

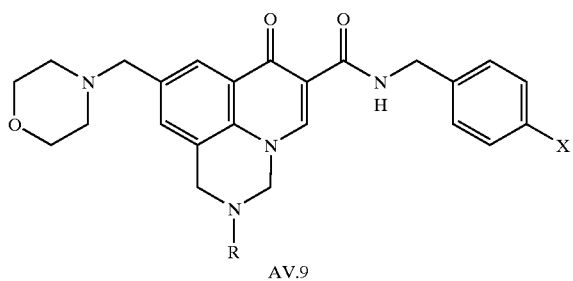

AV.9

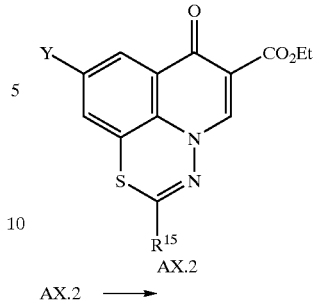

AX.2

AX.2 →

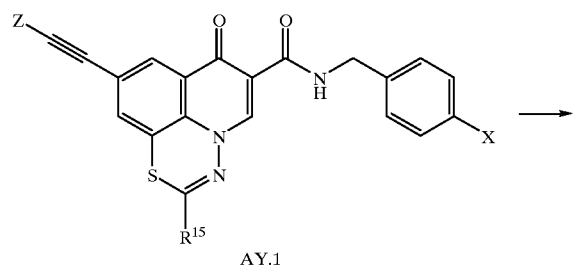

AX.3

To prepare derivatives where G=3-hydroxypropyl or 3-hydroxy-1-propynyl, intermediate AX.3 (Y=iodo) is further elaborated as in Chart AY by Sonogashira coupling with an electron-rich acetylene (e.g. propargyl alcohol, Z=CH$_2$OH) catalyzed by PdCl$_2$(PPh$_3$)$_2$ and copper(I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) to provide the corresponding alkynyl derivatives of formula AY.1 (Z=CH$_2$OH). Saturation of the alkyne by hydrogenation catalyzed by palladium on carbon in alcoholic solvents affords alkyl derivatives of formula AY.2 (Z=CH$_2$OH).

CHART AW

AV.8 ⟶

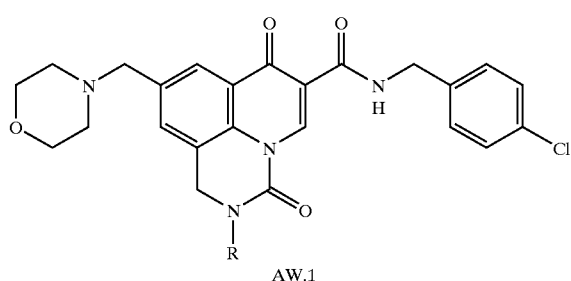

AW.1

W1.17. 7-Oxo-7H-[1,3,4]thiadiazino[6,5,4-ij]quinoline-6-carboxamide. The preparation of specific examples of heterocycle W1.17 is described in Chart AX following an established literature precedent (*Russ. J. Org. Chem.* 1999, 35, 1698–1705). Reaction of β-ketoesters of the formula H.1 (prepared as described in Chart J, where Y=iodo; Chart K, where Y=morpholinylmethyl; and Chart L, where Y=4-tetrahydropyranylmethyl) with acetic anhydride and triethylorthoformate followed by treatment of the resulting enol ether with a substituted thiosemicarbazide (e.g. morpholinothiosemicarbazide, R$^{15}$=morpholinyl) affords compounds of the formula AX.1. Upon heating AX.1 in benzene, thiadiazinoquinoline AX.2 is provided. The resulting ester is then treated with a benzylamine (e.g. 4-chlorobenzylamine, 4-bromobenzylamine, or 4-fluorobenzylamine) at high temperature to afford the corresponding amides of the general formula AX.3.

CHART AY

AX.3 ⟶

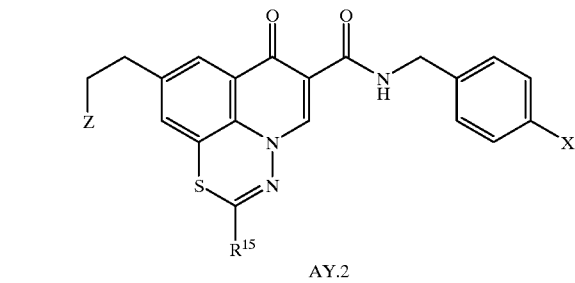

AY.1

AY.2

CHART AX

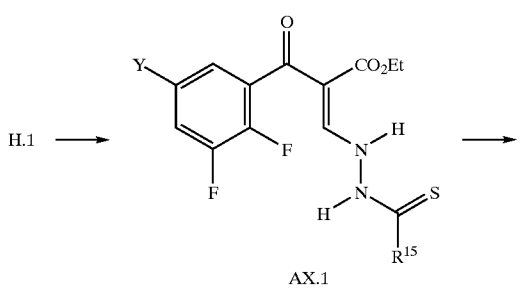

AX.1

W1.18. 7-Oxo-2,3-dihydro-1H,7H-pyrazino[3,2,1-ij][1,7]naphthyridine-6-carboxamide. Preparation of specific examples of heterocycles W1.18 follows an established literature precedent (*Collect. Czech. Chem. Commun.* 1991, 56, 2420) as shown in Chart AZ. 6-Bromo-2-chloro-3-pyridinylamine (AZ.1, *J. Med. Chem.* 1995, 38, 4830.) is thermally cyclized with methyl 2-(((4-chlorobenzyl)amino) carbonyl)-3-methoxy-2-propenoate to afford AZ.2. The nitrogen is then alkylated in the presence of potassium carbonate and 2-bromo-1-chloroethane in acetone to afford AZ.3. Reaction of AZ.3 with sodium iodide in acetone and treatment of the resulting iodide with sodium azide forms the alkyl azide AZ.4. Reduction of the azide with triphenylphosphine affords the amine AZ.5. The amine is then cyclized thermally to the pyrazine compound AZ.6. The pyrazino compound AZ.6 is then coupled under modified Negishi coupling with vinylzinc in the presence of Pd(PPh$_3$)$_4$ (Palmgren, A.; et.al *J. Org. Chem.* 1998, 63, 3764), followed by standard functional group manipulation involving oxidative cleavage with osmium tetroxide and sodium periodiate to give the aldehyde AZ.7. This aldehyde is then reacted with morpholine in the presence of acetic acid and sodium cyanoborohydride to afford AZ.8. Alternatively as described in Chart BA, AZ.6 is coupled to an electron-rich alkyne (e.g. propargyl alcohol) through a modified Sonogashira coupling (Linstrumelle, G.; et.al, *Tetrahedron Lett*, 1993, 34, 6403) to afford BA.1 (Z=CH$_2$OH). Saturation of the alkyne by hydrogenation catalyzed by palladium on carbon in alcoholic solvents affords alkyl derivatives of formula BA.2 (Z=CH$_2$OH).

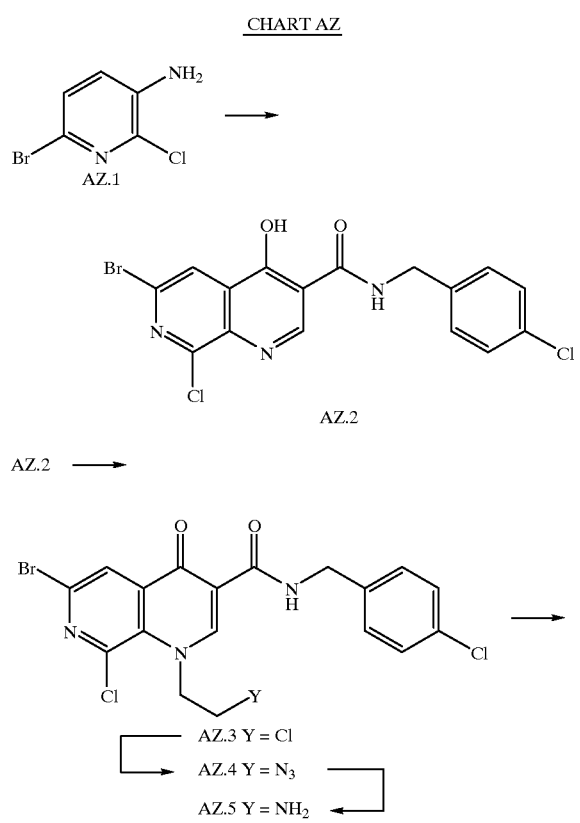

CHART AZ

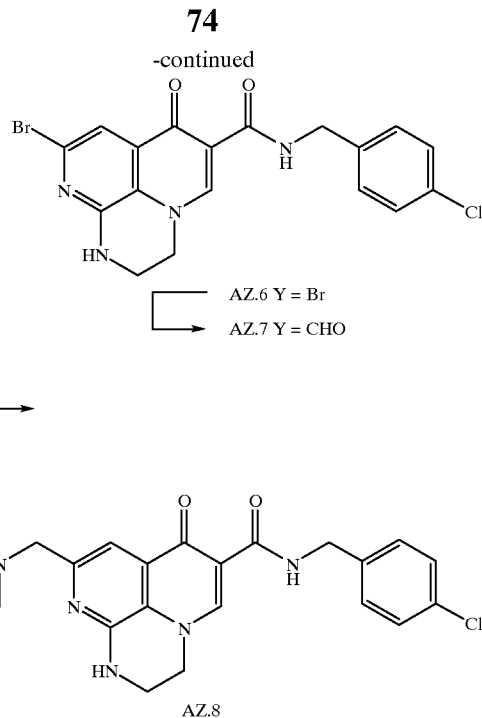

CHART BA

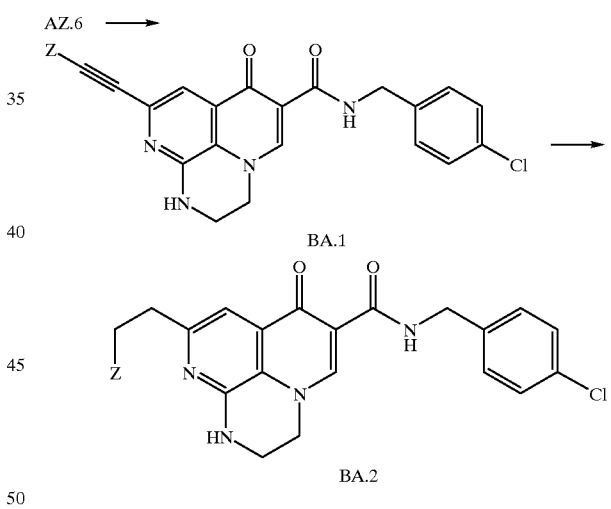

W1.19 7-Oxo-2,3-dihydro-7H-[1,4]thiazino[2,3,4-ij][1,7] naphthyridine-6-carboxamides. The preparation of specific examples of heterocycle W1.19 is described in Chart BB. Naphthyridine AZ.3 is reacted with potassium thioacetate in refluxing methanol in the presence of catalytic amount of sodium methoxide to afford BB.1. The thiazino compound BB.1 is then coupled under modified Negishi coupling conditions with vinylzinc in the presence of Pd(PPh$_3$)$_4$ (Palmgren, A.; et.al *J. Org. Chem.* 1998, 63, 3764), followed by standard functional group manipulation involving oxidative cleavage with osmium tetroxide and sodium periodiate to give the aldehyde BB.2. This aldehyde is then reacted with morpholine in the presence of acetic acid and sodium cyanoborohydride to afford BB.3. Alternatively as described in Chart BC, BB.2 is coupled to an electron-rich alkyne (e.g. propargyl alcohol) through a modified Sonogashira coupling (Linstrumelle, G.; et.al, *Tetrahedron Lett*, 1993, 34 6403) to afford BC.1 (Z=CH$_2$OH). Saturation of the alkyne by hydrogenation catalyzed by palladium on carbon in alcoholic solvents affords alkyl derivatives of formula BC.2 (Z=CH$_2$OH).

CHART BB

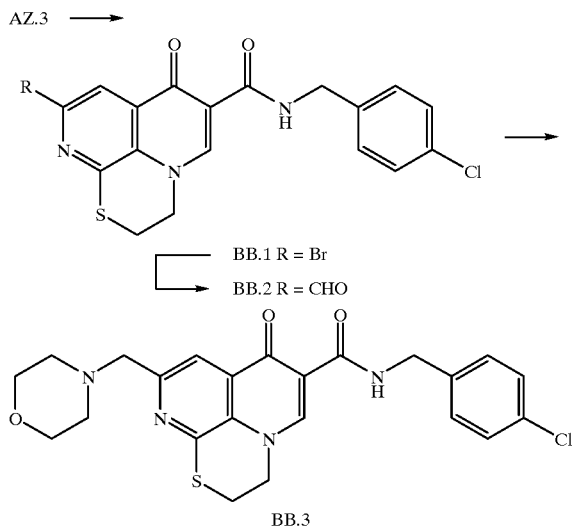

CHART BC

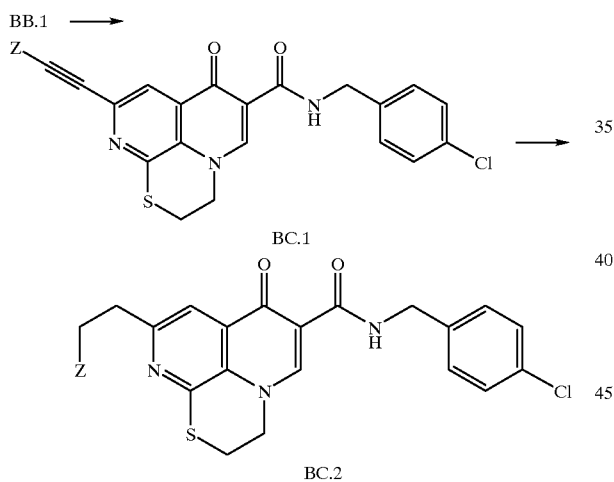

W1.20. 7-Oxo-2,3-dihydro-7H-[1,4]oxazino[2,3,4-ij][1,7]naphthyridine-6-carboxamides. The preparation of specific examples of heterocycle W1.20 is described in Chart BD. Treatment of AZ.3 with sodium iodide in acetone followed by reaction of the resulting intermediate iodide with sodium hydroxide to form the alkoxide which is then cyclized thermally to the oxazine compound BD.1. The oxazino compound BD.1 is then coupled under modified Negishi coupling with vinylzinc in the presence of Pd(PPh$_3$)$_4$ (Palmgren, A.; et.al *J. Org. Chem.* 1998, 63, 3764), followed by standard functional group manipulation involving oxidative cleavage with osmium tetroxide and sodium periodate to give the aldehyde BD.2. This aldehyde is then reacted with a primary or secondary amine (e.g. morpholine) in the presence of acetic acid and sodium cyanoborohydride to afford BD.3. Alternatively as described in Chart BE, compound BD.1 is coupled to an electron-rich acetylene (e.g. propargyl alcohol) through a modified Sonogashira coupling (Linstrumelle, G.; et.al, *Tetrahedron Lett,* 1993, 34 6403) to afford BE.1 (Z=CH$_2$OH). Saturation of the alkyne by hydrogenation catalyzed by palladium on carbon in alcoholic solvents affords alkyl derivatives of formula BE.2 (Z=CH$_2$OH).

CHART BD

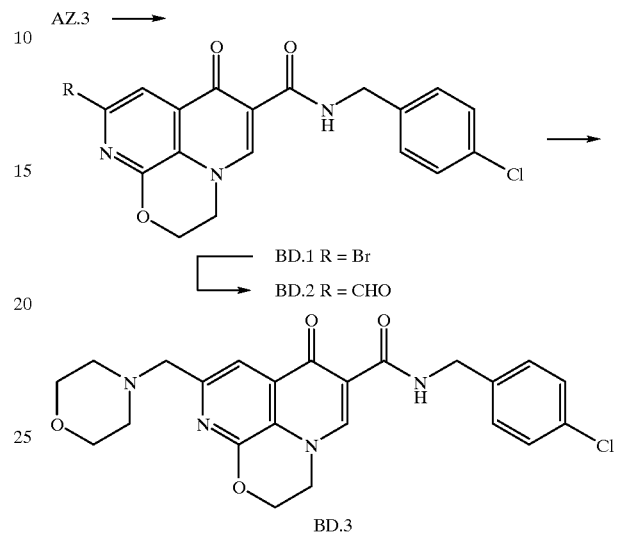

CHART BE

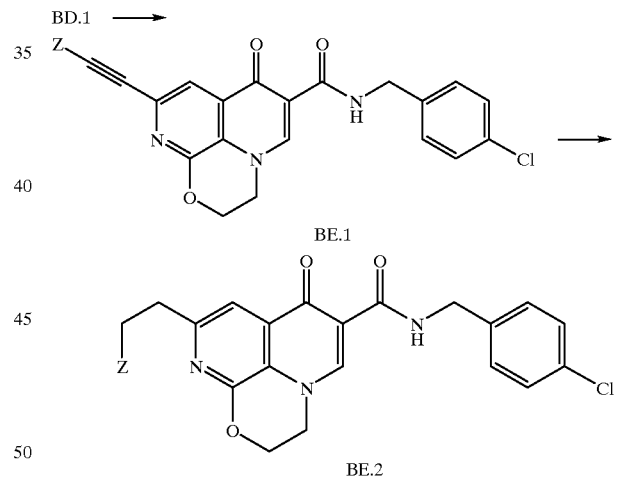

W1.23. 3,7-Dioxo-3H,7H-pyrido[1,2,3-de] quinoxaline-6-carboxamides. The preparation of specific examples of heterocycle W1.23 is described in Chart BF and Chart BG. Compounds of the formula Z.1 (Y=morpholinylmethyl, 3-hydroxypropyl, or 3-hydroxy-1-propynyl) react with butyl glyoxylate to give pyrido[1,2,3-de]quinoxalines BF.1 (Y=morpholinylmethyl, 3-hydroxy-1-propynyl, or 3-hydroxypropyl). Alternatively, as described in Chart BG compounds of the formula AC.1 react with a primary amine (e.g. 4-chlorobenzylamine, R$^{10}$=4-chlorobenzyl; benzylamine, R$^{10}$=benzyl) at high temperature to afford derivatives of the formula BG.1.

CHART BF

Z.1 →

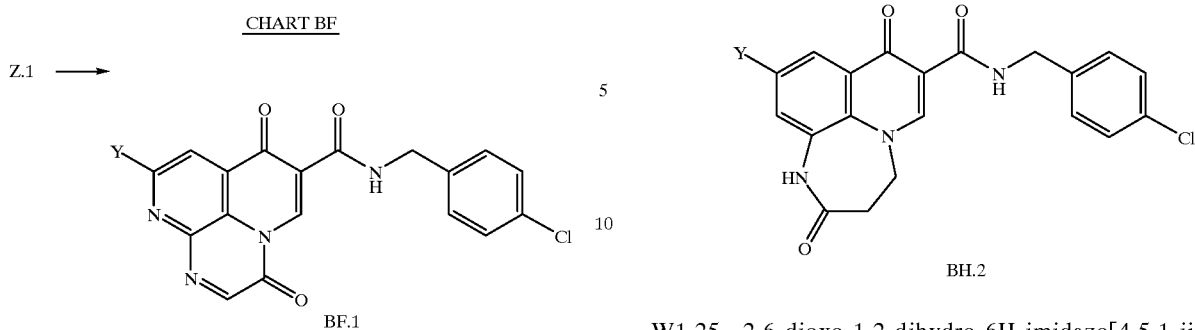

BF.1

CHART BG

AC.1 →

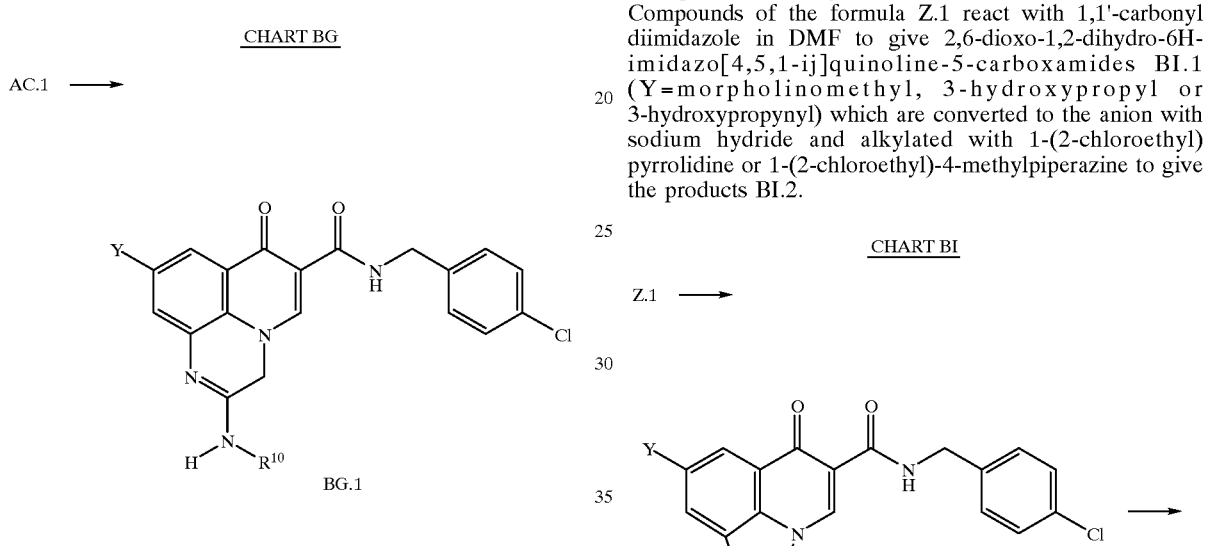

BG.1

W1.24. 2,4,8-Trioxo-1,2,3,4-tetrahydro-8H-[1,4]diazepino[3,2,1-ij]quinoline-7-carboxamides. The preparation of specific examples of heterocycle W1.24 is described in Chart BH. Compounds of the formula Z.1 (Y=morpholinylmethyl, 3-hydroxypropyl, or 3-hydroxy-1-propynyl) react with malonyl chloride to give diazepinoquinolines BH.1 (Y=morpholinylmethyl, 3-hydroxy-1-propynyl, or 3-hydroxypropyl). Alternatively, compounds of formula Z.1 react with acryloyl chloride to give diazepinoquinolines of the formula BH.2.

CHART BH

Z.1 →

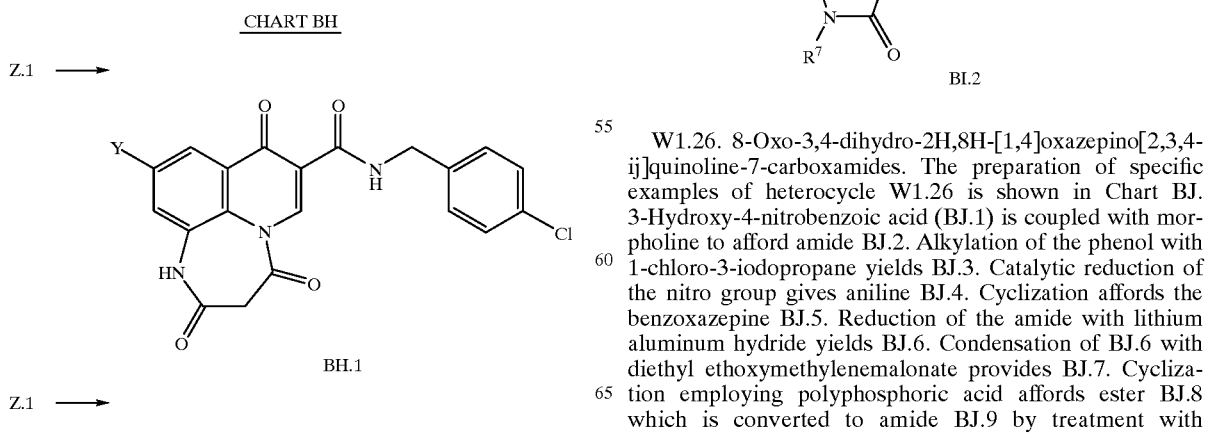

BH.1

Z.1 →

-continued

[structure BH.2]

BH.2

W1.25. 2,6-dioxo-1,2-dihydro-6H-imidazo[4,5,1-ij]quinoline-5-carboxamides. The preparation of specific examples of heterocycle W1.25 is described in Chart BI. Compounds of the formula Z.1 react with 1,1'-carbonyl diimidazole in DMF to give 2,6-dioxo-1,2-dihydro-6H-imidazo[4,5,1-ij]quinoline-5-carboxamides BI.1 (Y=morpholinomethyl, 3-hydroxypropyl or 3-hydroxypropynyl) which are converted to the anion with sodium hydride and alkylated with 1-(2-chloroethyl)pyrrolidine or 1-(2-chloroethyl)-4-methylpiperazine to give the products BI.2.

CHART BI

Z.1 →

[structure BI.1]

BI.1

[structure BI.2]

BI.2

W1.26. 8-Oxo-3,4-dihydro-2H,8H-[1,4]oxazepino[2,3,4-ij]quinoline-7-carboxamides. The preparation of specific examples of heterocycle W1.26 is shown in Chart BJ. 3-Hydroxy-4-nitrobenzoic acid (BJ.1) is coupled with morpholine to afford amide BJ.2. Alkylation of the phenol with 1-chloro-3-iodopropane yields BJ.3. Catalytic reduction of the nitro group gives aniline BJ.4. Cyclization affords the benzoxazepine BJ.5. Reduction of the amide with lithium aluminum hydride yields BJ.6. Condensation of BJ.6 with diethyl ethoxymethylenemalonate provides BJ.7. Cyclization employing polyphosphoric acid affords ester BJ.8 which is converted to amide BJ.9 by treatment with 4-chlorobenzylamine at elevated temperature.

CHART BJ

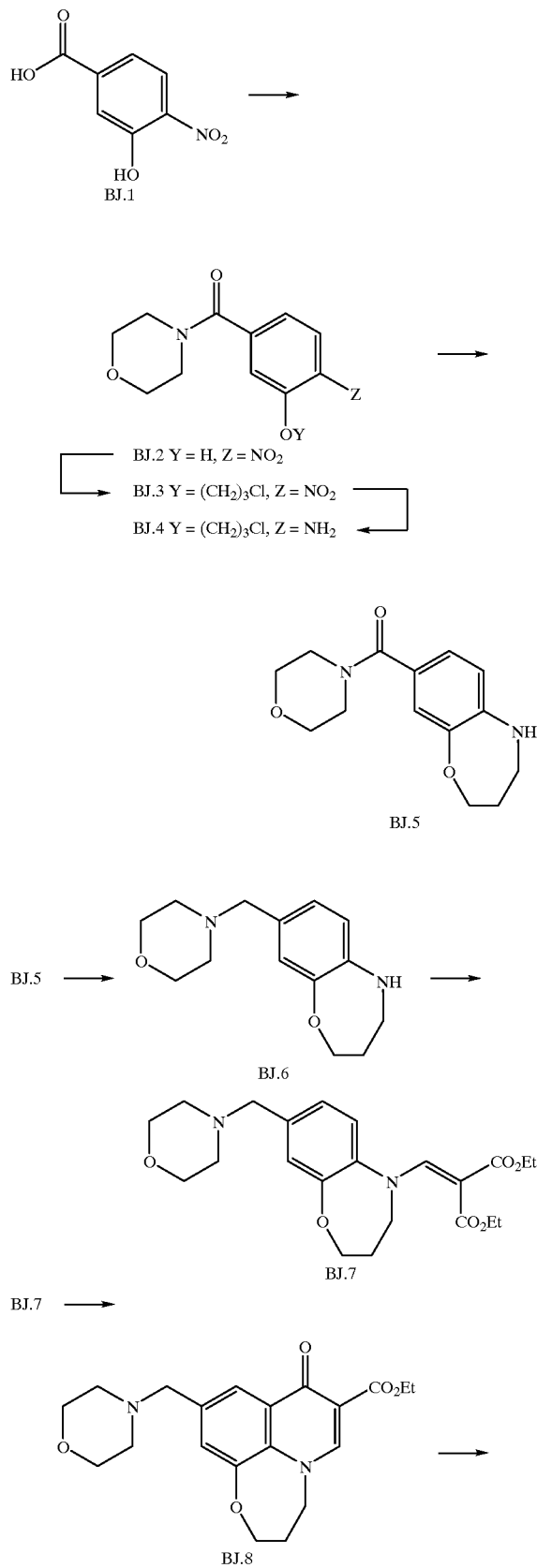

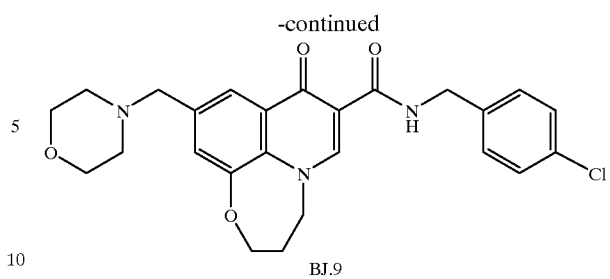

W1.52. 7-Oxo-7H-[1,4]oxazino[2,3,4-ij]quinoline-6-carboxamide. Representative examples of heterocycle W1.52 are prepared as described in Chart BK in analogy to reported pyridobenzoxazino ring synthesis (Augeri, D. J.; Fray, A. H.; Kleinman, E. F. *J. Heterocyclic Chem.* 1990, 27, 1509). Intermediates of the formula O.3 (Y=iodo, morpholinylmethyl, or tetrahydropyranylmethyl) are treated with a base (e.g. sodium hydride) to afford tricycles of the formula BK.1. The resulting ester is saponified under dilute acid conditions and coupled with a substituted benzylamine (e.g. 4-chlorobenzylamine) mediated by 1,1'-carbonyldiimidazole (or other suitable carboxylic acid activating agent) to provide amides of the general formula BK.3. In the case where Y=iodo, compounds of the general formula BK.3 are further derivatized as described in Chart BL. Sonogashira coupling between BK.3 (Y=iodo) and an electron-rich acetylene (e.g. propargyl alcohol, Z=CH$_2$OH) catalyzed by PdCl$_2$(PPh$_3$)$_2$ and copper(I) iodide either in diethylamine (Sonogashira, K.; Tohada, Y.; Hagihara, N. *Tetrahedron Lett.* 1975, 50, 4467.) or in a mixture of DMF and triethylamine (Fisher, M. J. et. al. *J. Med. Chem.* 1997, 40, 2085.) provides the corresponding alkynyl derivatives of formula BL.1 (Z=CH$_2$OH). Saturation of the alkyne by hydrogenation catalyzed by palladium on carbon in alcoholic solvents affords alkyl derivatives of formula BL.2 (Z=CH$_2$OH).

CHART BK

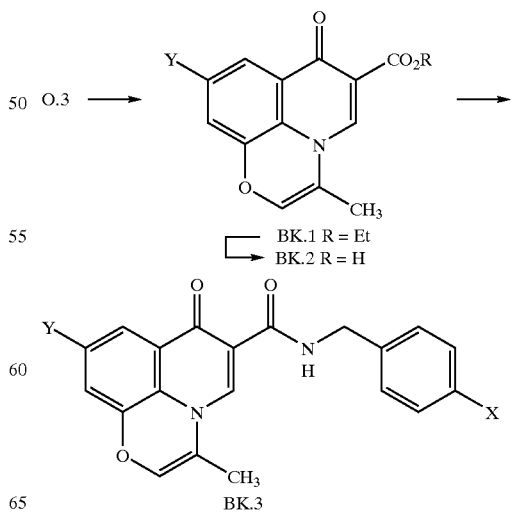

CHART BL

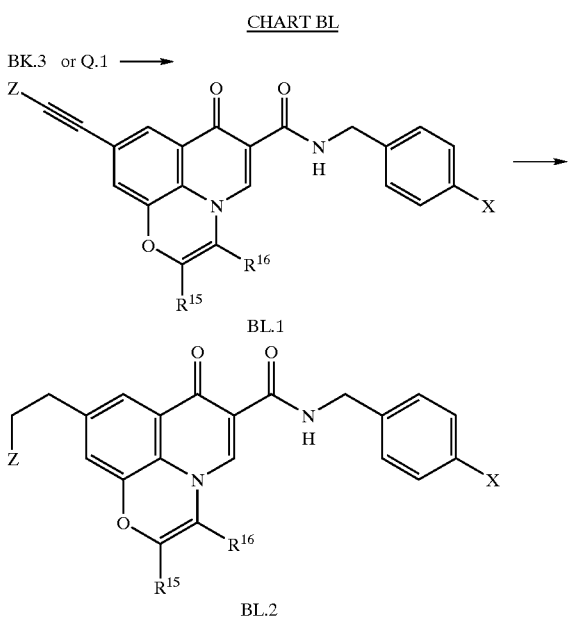

Alternatively, intermediates of the formula Q.4, cyclize in the presence of a base to afford tricycles of the formula BM.1. Employing conditions analogous to that previously described in Chart BL, intermediate BM.1 is transformed to the corresponding derivatives where G is optionally unsaturated $C_{1-4}$alkyl substituted by hydroxy (BL.1, BL.2). Alternatively, BM.1 is formylated employing carbon monoxide, a palladium catalyst, and an appropriate reducing agent to provide carboxaldehydes of the formula BM.2. Subsequent reductive amination between BM.2 and a primary or secondary amine (e.g. morpholine) affords compounds of the formula BM.3.

CHART BM

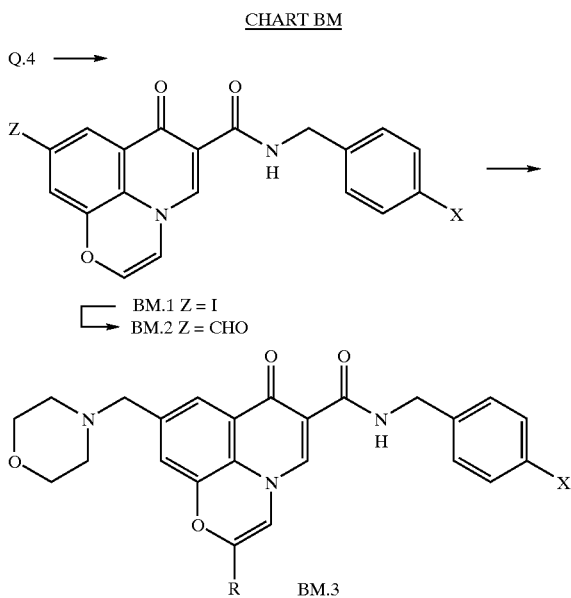

W1.57. 8-Oxo-1,2,3,4-tetrahydro-8H-[1,4]diazepino[6,7,1-ij]quinoline-7-carboxamide. Representative examples of heterocycle W1.57 are prepared as described in Chart BN. Intermediate AV.8 (R is as defined by $R^7$ above for optionally substituted alkyl, optionally substituted cycloalkyl, aryl, or het) is reacted with bromoacetic anhydride and a tertiary amine base (e.g. triethylamine) in N-methylpyrrolidinone to afford compounds of the general formula BN.1.

CHART BN

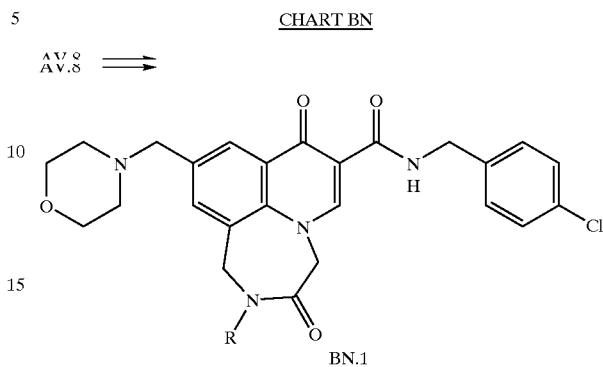

W3.1. 4,7-dioxo-1,4,7,8-tetrahydro[1,8]naphthyridine-3-carboxamides. The preparation of specific examples of heterocycle W3.1 follows established precedent as shown in Chart BO. 2-Amino-4-bromopyridine (BO.1) is reacted with Boc-anhydride in dichloromethane to afford the Boc-protected amine BO.2 which is then oxidized with peroxybenzoic acid (*Justus Liebigs Ann. Chem.* 1972, 758, 111) to provide BO.3. The nitrogen is then alkylated with 2-bromoethyl trimethylsilyl ether in the presence of potassium carbonate in acetone to provide BO.4. The Boc group is then removed under standard deprotection conditions to afford BO.5. The pyrimidone BO.5 is then cyclized with methyl 2-(((4-chlorobenzyl)amino)carbonyl)-3-methoxy-2-propenoate to give BO.6. Deprotection of the TMS ether followed by alkylation under Mitsunobu conditions (triphenyl phosphine and DEAD) affords BO.7. Naphthyridine BO.7 is then coupled under modified Negishi coupling with vinylzinc in the presence of $Pd(PPh_3)_4$ (Palmgren, A.; et.al *J. Org. Chem.* 1998, 63, 3764), followed by standard functional group manipulation involving oxidative cleavage with osmium tetroxide and sodium periodiate to give the aldehyde BO.8. This aldehyde is then reacted with a primary or secondary amine (e.g. morpholine) in the presence of acetic acid and sodium cyanoborohydride to afford BO.9.

CHART BO

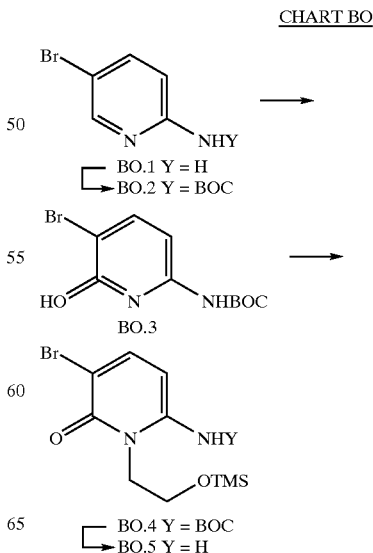

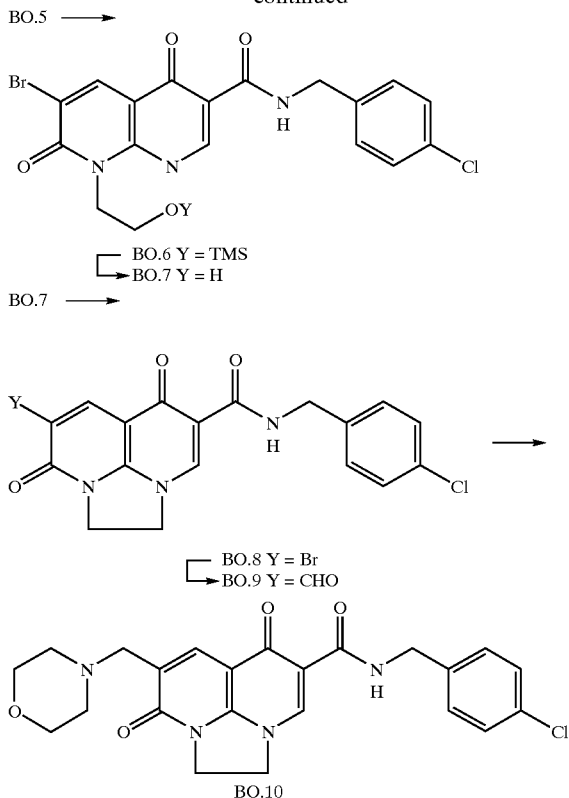

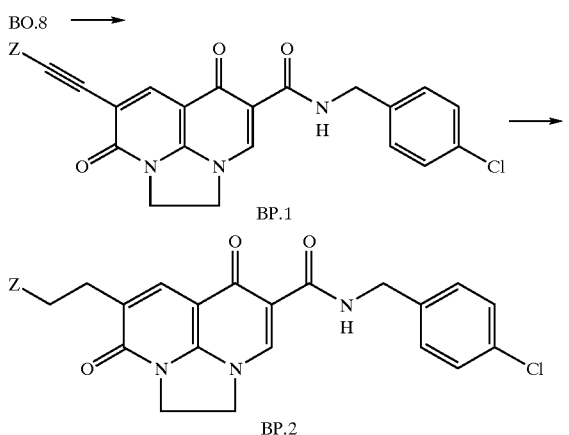

Specific examples in which G=3-hydroxypropyl or 3-hydroxy-1-propynyl are prepared as described in Chart BP. Bromide BO.8 is coupled with an electron-rich acetylene (e.g. propargyl alcohol) through a modified Sonogashira coupling (Linstrumelle, G.; et.al, *Tetrahedron Lett*, 1993, 34 6403) to afford BP.1 (Z=CH$_2$OH). Saturation of the alkyne by hydrogenation catalyzed by palladium on carbon in alcoholic solvents affords alkyl derivatives of the formula BP.2 (Z=CH$_2$OH).

W4.1. 3-Oxo-9,10-dihydro-3H,8H-pyrido[3,2,1-ij] quinoline-2-carboxamides. The preparation of specific examples of heterocycle W4.1 is described in Chart BQ. Reduction of 5,6,7,8-tetrahydroquinoline-3-carbonitrile (BQ.1) with DIBAL affords the corresponding carboxaldehyde BQ.2. Reductive amination between BQ.2 and a secondary amine (e.g. morpholine) affords a pyridyl derivative such as BQ.3. Treatment of BQ.3 with tert-butyl lithium followed by condensation of the resulting anion with diethyl ethoxymethylenemalonate provides the malonate BQ.4. Subsequent cyclization mediated by triethylamine affords BQ.5, and the resulting ester is condensed with a substituted benzylamine (e.g. 4-chlorobenzylamine) mediated by trimethylaluminum to afford a corresponding carboxamide of the formula BQ.6.

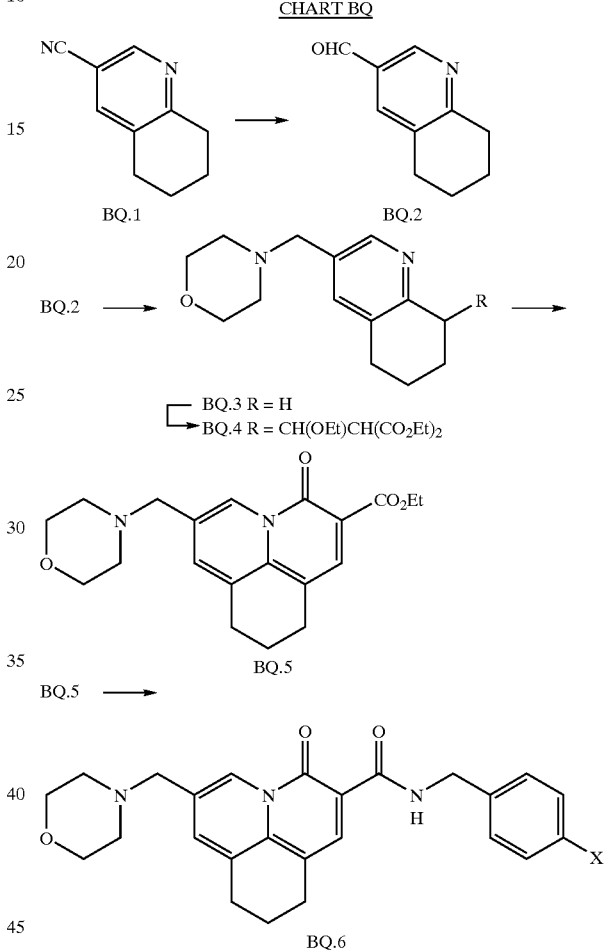

The inventive compounds may be used in their native form or as salts. In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, glutarate, and glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally (for example, by intravenous, intraperitoneal or intramuscular injection), topically (including but not limited to surface treatment, transdermal application, and nasal application), intravaginally, orally, or rectally, depending on whether the preparation is used to treat internal or external viral infections.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially nontoxic in the amounts employed. In addition, the active compound may be incorporated into sustained-release preparations and devices such as the osmotic release type devices developed by the Alza Corporation under the OROS trademark.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing 5 to 1000 mg, conveniently 10 to 750 mg, most conveniently, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

For internal infections, the compositions can be administered orally or parenterally at dose levels, calculated as the free base, of about 0.1 to 300 mg/kg, preferably 1.0 to 30 mg/kg of mammal body weight, and can be used in man in a unit dosage form, administered one to four times daily in the amount of 1 to 1000 mg per unit dose.

For parenteral administration or for administration as drops, as for eye infections, the compounds are presented in aqueous solution in a concentration of from about 0.1 to about 10%, more preferably about 0.1 to about 7%. The solution may contain other ingredients, such as emulsifiers, antioxidants or buffers.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The exact regimen for administration of the compounds and compositions disclosed herein will necessarily be dependent upon the needs of the individual subject being treated, the type of treatment and, of course, the judgment of the attending practitioner. The compounds of the present invention can be administered to an animal in need of treatment. In most instances, this will be a human being, but the treatment of livestock and companion animals is also specifically contemplated as falling within the scope of the instant invention.

The compounds of formula (I) and pharmaceutically acceptable salts thereof are useful as antiviral agents. Thus, they are useful to combat viral infections in animals, including man. The compounds are generally active against herpes viruses, and are particularly useful against the varicella zoster virus, the Epstein-Barr Virus, the herpes simplex virus types 1 and 2 (HSV-1 and 2), the human herpes virus types 6, 7 and 8 (HHV-6, 7 and 8) and the human cytomegalovirus (HCMV).

The invention will be further described by the following non-limiting examples.

EXAMPLE 1

N-(4-Chlorobenzyl)-10-(4-morpholinylmethyl)-8-oxo-3,4-dihydro-2H,8H-[1,4]oxazepino [2,3,4-ij] quinoline-7-carboxamide [BJ.9]

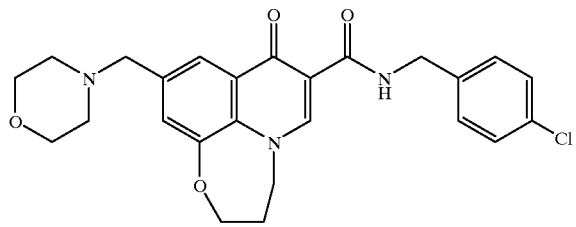

A suspension of 3-hydroxy-4-nitrobenzoic acid (18.3 g) and EDC hydrochloride (23.0 g) in 250 mL of dichloromethane at 0° C. is treated with morpholine (15.0 mL). The reaction is allowed to warm to room temperature. After 2 days, the resulting solution is washed with phosphate buffer (pH~6). The aqueous layer is extracted with two portions of dichloromethane. The combined organic layer is washed with phosphate buffer (pH~7), brine, dried over sodium sulfate, filtered and concentrated under reduced pressure. The resulting solid is crystallized from ethyl acetate in hexane to yield 21.1 g of the intermediate amide (BJ.2). A solution of this amide (2.52 g) in dry DMF (25 mL) is treated with cesium carbonate (6.51 g) followed by 1-chloro-3-iodopropane (1.89 mL). The resulting suspension is heated to 65° C. After 2 days, the resulting mixture is cooled to room temperature and then partitioned between ethyl acetate (150 mL) and water (100 mL). The organic layer is washed with saturated aqueous sodium carbonate. The combined aqueous layer is back-extracted with ethyl acetate (50 mL). The combined organic layer is washed with brine, dried over sodium sulfate, filtered and concentrated under reduced pressure. The resulting residue is purified by flash column chromatography on silica gel eluting with ethyl acetate to yield 1.80 g of the intermediate ether (BJ.3). A solution of this ether (1.8 g) in THF (50 mL) is treated with 5% platinum on carbon (0.35 g) and placed under 40 psi of hydrogen gas. The resulting suspension is shaken overnight and then filtered through Celite with THF washes of the filter cake. The filtrate is concentrated under reduced pressure to yield 1.68 g of the crude intermediate aniline (BJ.4). A mixture of this crude aniline (1.7 g) in toluene (25 mL) is treated with cesium iodide (0.08 g) and diisopropylethylamine (0.55 mL). The mixture is heated to 100° C. for 3 days and then cooled to room temperature. The mixture is concentrated under reduced pressure then partitioned between dichloromethane and aqueous sodium bicarbonate. The organic layer is washed with brine, dried over sodium sulfate, filtered and concentrated under reduced pressure. The resulting residue is purified by flash column chromatography on silica gel eluting with ethyl acetate to yield 0.17 g of the intermediate benzoxazepine (BJ.5). A solution of this benzoxazepine (0.17 g) in THF (5 mL) is cooled to 0° C. and treated with lithium aluminum hydride (LAH (0.06 g)). After 0.5 hrs, the mixture is allowed to warm to room temperature. After 1 hr, the reaction is quenched with water (0.07 mL), 15% aqueous sodium hydroxide (0.07 mL), and finally water (0.21 mL). The mixture is vigorously stirred for 0.5 hrs, filtered, and the resulting precipitate is washed with THF and dichloromethane. The filtrate is concentrated under reduced pressure and the resulting residue is purified by flash column chromatography on silica gel eluting with 1% to 3% methanol in ethyl acetate to yield 0.08 g of the reduced amide (BJ.6). A portion of this material (0.08 g) is treated with diethyl ethoxymethylenemalonate (0.45 mL) and heated to 160° C. in a tightly capped flask. After 2 hrs, the mixture is cooled to room temperature. The reaction mixture is purified by flash column chromatography on silica gel eluting with 1% to 4% methanol in dichloromethane to yield 0.10 g of the intermediate enamine (BJ.7). A solution of this enamine (0.10 g) in toluene (2 mL) is treated with polyphosphoric acid (0.6 g) and heated to 130° C. under a flow of nitrogen gas. After 1.5 hrs, the mixture is cooled to room temperature. The reaction mixture is quenched with saturated aqueous sodium bicarbonate and partitioned with dichloromethane. The basic aqueous layer is extracted with additional portions of dichloromethane. The combined organic layer is washed with brine, dried over sodium sulfate, filtered, and concentrated under reduced pressure to yield 0.09 g of the crude ester (BJ.8). A solution of this crude ester (0.09 g) in 4-chlorobenzylamine (0.5 mL) is heated to 180° C. After 2 hrs, the mixture is cooled to room temperature and concentrated under reduced pressure.

The residue is purified by flash column chromatography on silica gel eluting with 2% to 5% methanol in dichloromethane and then by crystallization from acetonitrile to yield 0.08 g of the title compound as a white solid. Physical characteristics: M.p. 195–197° C.; $^1$H NMR (DMSO-d$_6$) δ10.3, 8.8, 7.9, 7.4–7.3, 4.6, 4.5, 4.3, 3.6, 3.5, 2.3; MS (ESI+) m/z 468 (M+H)$^+$; Anal. Found: C, 64.05; H, 5.61; N, 8.97.

PREPARATION 1

Ethyl 4-hydroxy-6-(4-morpholinylmethyl)-8-nitro-3-quinolinecarboxylate [AA.5]

N-Bromosuccinimide (3.52 g) is added to a solution of ethyl 4-hydroxy-6-methyl-8-nitro-3-quinolinecarboxylate (2.76 g) in 1,2 dichloroethane (250 mL). The refluxing solution is irradiated with a sun lamp (625 watt) for 20 min. The crude ethyl 6-bromomethyl-4-hydroxy-8-nitro-3-quinolinecarboxylate thus formed is reacted with morpholine (5 mL). After evaporation, the product is partitioned between ethyl acetate and water. Evaporation of the ethyl acetate gives a solid, which is dissolved in chloroform and is chromatographed on silica gel with 1% methanol/chloroform as the initial eluant. Elution of the column with 10% methanol/chloroform gives the title compound, which is crystallized from methanol. Physical characteristics: M.p. 214–216° C. $^1$H NMR (CDCl$_3$) δ1.41, 2.50, 3.68, 3.74, 4.42, 8.69, 8.73, 8.78, 11.6. Anal. Found: C, 56.30; H, 5.32; N, 11.56.

PREPARATION 2

Ethyl 8-amino-4-hydroxy-6-(4-morpholinylmethyl)-3-quinolinecarboxylate [AA.6]

A solution of ethyl 4-hydroxy-6-(4-morpholinylmethyl)-8-nitro-3-quinolinecarboxylate (Preparation 1, 1.36 g) in DMF (50 mL) is hydrogenated at 50 psi hydrogen pressure in the presence of 10% Pd/C (400 mg) for 15 min. The catalyst is filtered off and the filtrate is evaporated. The residual solid is triturated with methanol to afford 1.12 g of the title compound. Physical characteristics. $^1$H NMR (DMSO-d$_6$) δ1.28, 2.35, 3.44, 3.57, 4.21, 5.59, 6.98, 7.33, 8.41.

PREPARATION 3

8-Amino-N-(4-chlorobenzyl)-4-hydroxy-6-(4-morpholinylmethyl)-3-quinolinecarboxamide [Z.1]

A mixture of ethyl 8-amino-4-hydroxy-6-(4-morpholinylmethyl)-3-quinolinecarboxylate (Preparation 2, 1.0 g) and 4-chlorobenzylamine (4 mL) is heated at 180° C. The solution is cooled and stirred with ether (6 mL) and water (6 mL). The resulting precipitate is removed by filtration, washed with water followed by ether and dried to afford 1.05 g of the title compound. Physical characteristics: $^1$H NMR (DMSO-d$_6$) δ2.35, 3.45, 3.57, 4.54, 5.65, 7.02, 7.39, 8.62, 10.6, 11.1.

EXAMPLE 2

N-(4-Chlorobenzyl)-8-(4-morpholinylmethyl)-2,6-dioxo-1,2-dihydro-6H-imidazo[4,5,1-ij]quinoline-5-carboxamide [BI.1]

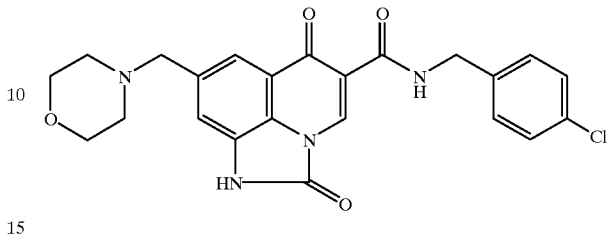

A mixture of 8-amino-N-(4-chlorobenzyl)-4-hydroxy-6-(4-morpholinylmethyl)-3-quinolinecarboxamide (Preparation 3, 331 mg) and 1,1'-carbonyl diimidazole (215 mg) in DMF (2.5 mL) is heated at 80° C. for 1 h. A second portion of 1,1'-carbonyl diimidazole (167 mg) is added and heating is continued for an additional 1 h. After cooling, water (8 mL) is added and the resulting precipitate is filtered off, washed with water and dried to afford 261 mg of the title compound. Physical characteristics: M.p. 286° C. (dec); $^1$H NMR (300 MHz, DMSO-d$_6$) δ2.39, 3.57, 3.62, 4.57, 7.39, 7.61, 8.88, 10.0, 12.0. Anal. Found: C, 60.37; H, 4.78; N, 12.49.

EXAMPLE 3

N-(4-Chlorobenzyl)-9-(4-morpholinylmethyl)-2,7-dioxo-2,3-dihydro-1H,7H-pyrido[1,2,3-de]quinoxaline-6-carboxamide [AC.1]

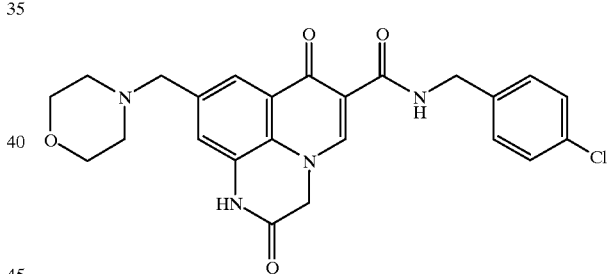

Bromoacetic anhydride (290 mg) is added to a stirred solution of 8-amino-N-(4-chlorobenzyl)-4-hydroxy-6-(4-morpholinylmethyl)-3-quinolinecarboxamide (Preparation 3, 426 mg) in anhydrous DMF (5.0 mL). After 30 min, triethylamine (100 mg) and additional bromoacetic anhydride (100 mg) are added. After 1 h, triethylamine (300 mg) is added and the solution is heated briefly at 80° C. Methanol (8 mL) is added and the resulting precipitate is filtered off, washed with water and dried to afford 262 mg of the title compound as a DMF solvate. Physical characteristics: $^1$H NMR (DMSO-d$_6$) δ2.37, 2.73, 2.89, 3.53, 3.57, 4.56, 5.11, 7.23, 7.35, 7.40, 7.72, 7.95, 8.72, 10.35, 11.2.

PREPARATION 4

Ethyl 9-(4-morpholinylmethyl)-2,7-dioxo-2,3-dihydro-1H,7H-pyrido[1,2,3-de]quinoxaline-6-carboxylate Bromoacetic anhydride (280 mg) is added to ethyl 8-amino-4-hydroxy-6-(4-morpholinylmethyl)-3- quinolinecarboxylate (Preparation 2, 330 mg) in DMF (4.0 mL). Triethylamine (400 mg) is added and the reaction is heated for 10 min at 60° C. After 1 h, the DMF is removed and the product is chromatographed on silica gel with 10% methanol as the eluant to give 310 mg of the title compound as a mixture with triethylamine hydrobromide. Physical characteristics: $^1$H NMR (DMSO-$d_6$) δ1.40, 2.45, 3.56, 3.69, 4.39, 4.88, 7.49, 7.97, 8.34.

EXAMPLE 4

N-(4-Chlorobenzyl)-2-[(4-chlorobenzyl)amino]-9-(4-morpholinylmethyl)-7-oxo-3H,7H-pyrido[1,2,3-de]quinoxaline-6-carboxamide [BG.1, Y=morpholinylmethyl, $R^{10}$=4-chlorobenzyl]

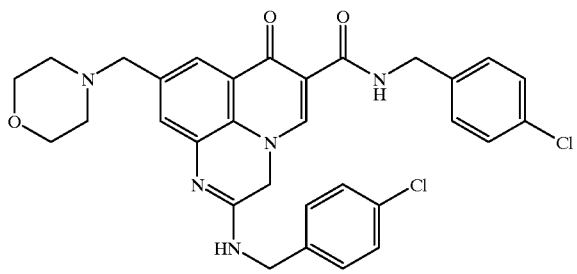

A mixture of ethyl 9-(4-morpholinylmethyl)-2,7-dioxo-2,3-dihydro-1H,7H-pyrido[1,2,3-de]quinoxaline-6-carboxylate (Preparation 4, 280 mg) and 4-chlorobenzylamine (1 mL) is heated at 180° C. The solution is cooled, diluted with methanol (2 mL), and the precipitate is filtered off. The resulting solid is washed with methanol followed by ether and dried to give 117 mg of the title compound. Physical characteristics: $^1$H NMR (DMSO-$d_6$) δ2.35, 3.49, 3.57, 4.56, 4.60, 5.08, 7.20, 7.34–7.40, 7.64, 8.21, 8.62, 10.6. Anal. Found: C, 62.90; H, 4.99; N, 11.81; Cl, 12.03.

PREPARATION 5

2,3-Dihydro-1H-indol-2-ylmethanol [G.2]

A slurry of racemic indoline-2-carboxylic acid (5.00 g) and anhydrous THF (60 mL) is cooled to 0° C. under an atmosphere of nitrogen. To this slurry is added 1.0 M borane-THF complex (100 mL) via syringe over 40 minutes. The resulting solution is allowed to warm to room temperature while stirring overnight. Water (ca. 400 mL) is slowly added to quench the reaction. The mixture is extracted with diethyl ether (400 mL). The combined organic layers are washed with saturated sodium bicarbonate solution followed by brine, dried (Na$_2$SO$_4$), filtered, and concentrated to afford 4.31 g (94%) of the title compound as a colorless foam. Physical characteristics: MS (ESI+) m/z 150 (M+H)$^+$.

PREPARATION 6

Benzyl 2-(Hydroxymethyl)-1-indolinecarboxylate [G.3]

A solution containing 2,3-dihydro-1H-indol-2-ylmethanol (Preparation 5, 4.31 g) and THF (60 mL) is added to a flask containing sodium bicarbonate (24.27 g) and water (15 mL). Benzylchloroformate (4.5 mL) is slowly added. Once addition is complete, the mixture is stirred overnight. The crude mixture is filtered and washed with a large amount of CH$_2$Cl$_2$. The filtrate is poured into water and the separated organic phase is washed with 5% HCl and brine. The organic layer is dried (Na$_2$SO$_4$), filtering, and concentrated to give a yellow oil. The crude product is chromatographed eluting with EtOAc/heptane (1/1) to give 8.11 g (99%) of the title compound as a pale colored oil. Physical characteristics: MS (ESI+) m/z 284 (M+H)$^+$.

PREPARATION 7

Benzyl 2-(Hydroxymethyl)-5-iodo-1-indolinecarboxylate [G.4]

A solution containing benzyl 2-(hydroxymethyl)-1-indolinecarboxylate (Preparation 6, 1.78 g), N-iodosuccinimide (2.83 g), and anhydrous DMF (12 mL) is stirred overnight at 60° C. in a foil-covered flask. This solution is cooled and concentrated to half volume with a stream of nitrogen. The resulting brown solution is partitioned between water (50 mL) and CH$_2$Cl$_2$ (150 mL). The organic phase is washed with brine, dried (Na$_2$SO$_4$), filtered, and concentrated to give a brown oil. The crude product is chromatographed eluting with 0–40% EtOAc in heptane (300 mL each 10%) to give 2.03 g (79%) of the title compound as a peach solid. Physical characteristics: M.p. 110–111° C.; HRMS (FAB) m/z 410.0270 (C$_{17}$H$_{16}$INO$_3$+H). Anal. Found: C, 49.83; H, 3.95; N, 3.37.

PREPARATION 8

(5-Iodo-2,3-dihydro-1H-indol-2-yl)methyl acetate [G.5]

A 30% wt solution containing HBr in acetic acid (25 mL) is added to a flask containing benzyl 2-(hydroxymethyl)-5-iodo-1-indolinecarboxylate (Preparation 8, 6.03 g). All of the solids are dissolved and the solution is concentrated to give a brown solid. The crude product is taken into CH$_2$Cl$_2$ with a small amount of methanol and triethylamine and purified by column chromatography eluting with heptane (250 mL), 20% EtOAc in heptane (500 mL), and 40% EtOAc in heptane to give 3.92 g (84%) of the title compound as a red solid. Physical characteristics: M.p. 64–66° C.; HRMS (FAB) m/z 318.0006 (C$_{11}$H$_{12}$INO$_2$+H). Anal. Found: C, 41.91; H, 3.85; N, 4.35.

PREPARATION 9

Ethyl 2-((Acetyloxy)methyl)-8-iodo-6-oxo-1,2-dihydro-6H-pyrrolo[3,2,1-ij]quinoline-5-carboxylate [G.6]

A mixture of diethyl ethoxymethylenemalonate (2.73 mL) and (5-iodo-2,3-dihydro-1H-indol-2-yl)methyl acetate (Preparation 8, 3.90 g) is heated to 120° C. under a stream of nitrogen. After starting material is consumed, the mixture is cooled and diluted with EtOAc. The crude product is chromatographed eluting with 20, 40, and 60% EtOAc in heptane (500 mL each) to give 5.28 g (88%) of the corresponding enamine as a brown oil. A portion of this material (4.61 g) is dissolved in Eaton's Reagent (10 mL) and heated to 80° C. for 1 h. Upon cooling, the crude mixture is poured into a cold beaker and a 50% NaOH solution is slowly added until pH=7. The cloudy solution is then poured into CH$_2$Cl$_2$. The organic layer is separated and washed with brine, dried (Na$_2$SO$_4$), filtered, and concentrated to give a brown solid. The crude product is chromatographed eluting with 0–4% methanol in CH$_2$Cl$_2$ to give 880 mg (21%) of the title compound as a brown solid. Physical characteristics: MS (ESI+) m/z 442 (M+H)$^+$, 464 (M+Na)$^+$.

PREPARATION 10

N-(4-Chlorobenzyl)-2-(hydroxymethyl)-8-iodo-6-oxo-1,2-dihydro-6H-pyrrolo[3,2,1-ij]quinoline-5-carboxamide [G.7, X=Cl]

A mixture of 4-chlorobenzylamine (2 mL) and ethyl 2-((acetyloxy)methyl)-8-iodo-6-oxo-1,2-dihydro-6H-pyrrolo[3,2,1-ij]quinoline-5-carboxylate (Preparation 9, 0.70 g) is heated to 120° C. under a stream of nitrogen for 7 h, to 100° C. for 18 h, and then to 130° C. for 8 hours. Upon cooling, the mixture is diluted with a mixture of CH$_2$Cl$_2$, EtOAc, and methanol (2/2/1) and absorbed onto silica gel. This material is chromatographed eluting with 0–4% methanol in CH$_2$Cl$_2$ to give a wet brown solid. The crude product is recrystallized by dissolving in hot acetic acid and slowly adding water until cloudiness persisted. Upon standing, crystals form which are collected to provide 340 mg (43%) of the title compound as a tan solid. Physical characteristics: M.p. 222–223° C.; MS (ESI+) m/z 495 (M+H)$^+$.

EXAMPLE 5

N-(4-Chlorobenzyl)-2-(hydroxymethyl)-8-(3-hydroxy-1-propynyl)-6-oxo-1,2-dihydro-6H-pyrrolo[3,2,1-ij]quinoline-5-carboxamide [G.8, X=Cl]

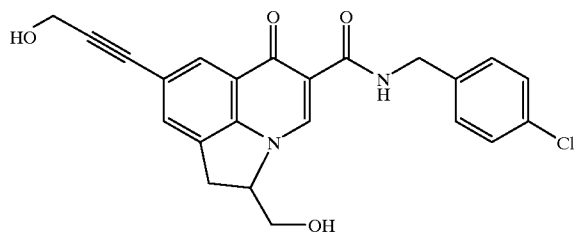

A solution containing N-(4-chlorobenzyl)-2-(hydroxymethyl)-8-iodo-6-oxo-1,2-dihydro-6H-pyrrolo[3,2,1-ij]quinoline-5-carboxamide (Preparation 10, 0.15 g), anhydrous DMF (6 mL), and triethylamine (0.8 mL) is purged with nitrogen three times before adding propargyl alcohol (19 µL), copper(I)iodide (14 mg), and PdCl$_2$(PPh$_3$)$_2$ (8 mg). The solution is heated to 65° C. and then is cooled, diluted with CH$_2$Cl$_2$ (25 mL), and poured into water (30 mL). The organic layer is washed with brine, dried (Na$_2$SO$_4$), filtered, and concentrated to give a brown residue. The crude product is chromatographed eluting with 0–6% methanol in CH$_2$Cl$_2$ (250 mL each) to give 90 mg (70%) of the title compound as a white solid. Physical characteristics: M.p. 224–225° C.; MS (ESI+) m/z 423 (M+H)$^+$.

PREPARATION 11

Diethyl 2-((2,2-Dimethyl-2,3-dihydro-1H-indol-1-yl)methylene)malonate [C.2]

A mixture of 2,2-dimethylindoline (1.47 g) and diethyl ethoxymethylenemalonate (2.0 ml) is heated to 105° C. for 17 hours to afford the title compound as a pale yellow oil. Physical characteristics: $^1$H NMR (CDCl$_3$) δ7.76, 7.18, 7.12, 6.97, 6.74, 4.24, 3.16, 1.50, 1.34.

PREPARATION 12

Ethyl 2,2-Dimethyl-6-oxo-1,2-dihydro-6H-pyrrolo[3,2,1-ij]quinoline-5-carboxylate [C.3]

Diethyl 2-((2,2-dimethyl-2,3-dihydro-1H-indol-1-yl)methylene)malonate (Preparation 11, 3.14 g) is dissolved in Eaton's Reagent (3.5 mL) and slowly heated to 100° C. The reaction is cooled and poured into EtOAc (350 mL). The separated organic layer is washed with water (2×200 mL). The aqueous extracts are extracted further with CH$_2$Cl$_2$ (2×100 mL). The organic extracts are washed with brine and dried over MgSO$_4$, filtered and concentrated to a brown oil which is purified by chromatography over silica gel, eluting with 5% methanol in CH$_2$Cl$_2$ to give 2.3 g (85%) of the title compound as a pale yellow oil that slowly crystallizes. Physical characteristics: M.p. 117–119° C.; $^1$H NMR (DMSO-d$_6$) δ8.73, 7.83, 7.61, 7.41, 4.22, 3.41, 1.63, 1.29; IR (diffuse reflectance) 1933, 1677, 1640, 1624, 1601, 1544, 1459, 1367, 1310, 1213, 1176, 1144, 1032, 773, 757 cm$^{-1}$; MS (EI) m/z 271 (M$^+$). Anal. Found: C, 70.48; H, 6.36; N, 5.12.

PREPARATION 13

Ethyl 8-Bromo-2,2-dimethyl-6-oxo-1,2-dihydro-6H-pyrrolo[3,2,1-ij]quinoline-5-carboxylate [C.4]

Ethyl 2,2-dimethyl-6-oxo-1,2-dihydro-6H-pyrrolo[3,2,1-ij]quinoline-5-carboxylate (Preparation 12, 1.03 g) is dissolved in acetic acid (10 mL) and bromine (213 µL) is added dropwise. The reaction is stirred an additional 30 min and then poured into water (50 mL). The resulting precipitate is filtered and then washed with ether to give 506 mg (38%) of the title compound as white crystals. Physical characteristics: M.p. 227–228° C.; $^1$H NMR (DMSO-d$_6$) δ8.76, 7.90, 7.79, 4.23, 3.41, 1.63, 1.29; IR (diffuse reflectance) 1727, 1636, 1612, 1592, 1547, 1505, 1393, 1373, 1327, 1303, 1217, 1171, 1167, 1128, 804 cm$^{-1}$; HRMS (FAB) 350.0386 (C$_{16}$H$_{16}$BrNO$_3$+H).

PREPARATION 14

Ethyl 8-(3-Hydroxyprop-1-ynyl)-2,2-dimethyl-6-oxo-1,2-dihydro-6H-pyrrolo[3,2,1-ij]quinoline-5-carboxylate [C.5, Z=CH$_2$OH]

A solution of palladium acetate (73 mg) and triphenyl phosphine (191 mg) in dry THF (6.0 mL) under nitrogen is cooled to 0° C. A solution of n-butyllithium (1.6 M in hexanes, 444 µL) is added dropwise and after 15 min, the solution is warmed to 22° C. for 15 min. The solution is then canulated into a mixture of ethyl 8-bromo-2,2-dimethyl-6-oxo-1,2-dihydro-6H-pyrrolo[3,2,1-ij]quinoline-5-carboxylate (Preparation 13, 350 mg), copper iodide (84 mg) and propargyl alcohol (75 µL) in diethylamine (6.0 mL). The reaction is warmed to 45° C. for 2 hours. The reaction is filtered, diluted with CH$_2$Cl$_2$ (100 mL), and washed with water. The organic layer is dried (MgSO$_4$), filtered, and concentrated. The crude product is chromatographed over silica gel, eluting with 5% MeOH in CHCl$_3$ and recrystallized from EtOAc to afford 229 mg of the title compound as white crystals. Physical characteristics: M.p. 237° C. (dec); $^1$H NMR (DMSO-d$_6$) δ8.74, 7.81, 7.60, 5.37, 4.33, 4.23, 3.39, 1.63 (s, 6 H), 1.29 (t, J=7 Hz, 3 H); IR (diffuse reflectance) 2391, 2222, 2058, 1921, 1680, 1637, 1595, 1542, 1510, 1317, 1216, 1186, 1040, 1031, 808 cm$^{-1}$; MS (EI) m/z 325 (M+). HRMS (FAB) m/z 326.1385 (C$_{19}$H$_{19}$NO$_4$+H).

EXAMPLE 6

N-(4-Chlorobenzyl)-8-(3-hydroxyprop-1-ynyl)-2,2-dimethyl-6-oxo-1,2-dihydro-6H-pyrrolo[3,2,1-ij]quinoline-5-carboxamide [C.6, X=chloro, Z=CH₂OH]

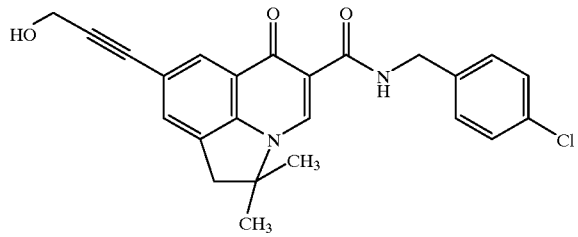

4-Chlorobenzylamine (110 µL) and sodium methoxide (25 mg) are added to a solution of ethyl 8-(3-hydroxyprop-1-ynyl)-2,2-dimethyl-6-oxo-1,2-dihydro-6H-pyrrolo[3,2,1-ij]quinoline-5-carboxylate (Preparation 14, 153 mg) in methanol (12 mL). The reaction is warmed to 50° C. for 48 hours. The reaction mixture is cooled in a freezer and the resulting white precipitate is filtered and washed with cold methanol, hexane, and ether to give 150 mg of the title compound as white crystals. Physical characteristics: M.p. 228° C. (dec); $^1$H NMR (DMSO-d$_6$) δ10.43, 8.98, 7.90, 7.66, 7.40, 5.39, 4.54, 4.34, 3.44, 1.66; IR (diffuse reflectance) 2226, 1907, 1646, 1618, 1568, 1538, 1510, 1493, 1434, 1318, 1307, 1223, 1033, 1012, 808 cm$^{-1}$; MS (EI) m/z 420 (M+); HRMS (FAB) 421.1332 ($C_{24}H_{21}ClN_2O_3$+H).

PREPARATION 15

5,6,7,8-Tetrahydroquinoline-3-carbaldehyde [BQ.2]

A 350 mL three neck rounded bottom flask equipped with a nitrogen inlet, bubbler, magnetic stir bar, and rubber septum is charged with 5,6,7,8-tetrahydroquinoline-3-carbonitrile (5.03 g) and 100 mL anhydrous toluene. The resulting solution is cooled to 5° C. with a water/ice bath, and a solution of DIBAL (35 mL of a 1M methylene chloride solution) is delivered over a 30 min period. After 3.5 hours at 0–5° C., the reaction mixture is quenched with 60 mL Na$_2$CO$_3$ solution, and the resulting biphasic solution is stirred for two hours before extracting with CH$_2$Cl$_2$ (100 mL). The organic layers are dried with Na$_2$SO$_4$ and concentrated in vacuo. The crude product is purified by flash chromatography (4% MeOH/CH$_2$Cl$_2$) to afford 3.02 g (60%) of the title compound as a light yellow oil. Physical characteristics: $^1$H NMR (CDCl$_3$) δ9.99, 8.75, 7.78, 2.96, 2.81, 1.90, 1.82; $^{13}$C NMR (CDCl$_3$) δ190.8, 164.2, 149.2, 136.0, 133.0, 129.4, 33.1, 28.6, 22.6, 22.8.

PREPARATION 16

3-(Morpholin-4-ylmethyl)-5,6,7,8-tetrahydroquinoline [BQ.3]

A 100 mL three-neck round bottom flask equipped with a nitrogen inlet, bubbler, and glass stopper is charged with 1,2-dichloroethane (45 mL), 5,6,7,8-tetrahydroquinoline-3-carbaldehyde (Preparation 15, 2.39 g) and morpholine (1.42 mL). To the above solution is added NaBH(OAc)$_3$ (5.01 g) in one portion. After 1 hour at room temperature, the reaction is quenched via slow addition of Na$_2$CO$_3$ (50 mL of a saturated aqueous solution). The resulting biphasic solution is stirred for two hours at room temperature then poured into methylene chloride (100 mL). The resulting layers are separated, and the organic layer is dried with Na$_2$SO$_4$, filtered, and concentrated in vacuo. The crude product is purified by flash chromatography (10% methanol/CH$_2$Cl$_2$) to give 2.60 g (76%) of the title compound as an oil which crystallizes on standing. Physical characteristics: M.p. 40.9° C.; $^1$H NMR (CDCl$_3$): δ8.24, 7.31, 3.68, 3.41, 2.88, 2.74, 2.41, 1.87, 1.78; $^{13}$C NMR (CDCl$_3$) δ156.4, 147.5, 137.6, 131.9, 130.1, 66.9, 60.4, 53.5, 32.2, 28.7, 23.1, 22.7.

PREPARATION 17

Diethyl 2-(Ethoxy(3-(morpholin-4-ylmethyl)-5,6,7,8-tetrahydroquinolin-8-yl)methyl)malonate [BQ.4]

A 500 mL round bottom flask equipped with stir bar, nitrogen inlet and bubbler is evacuated with nitrogen three times prior to being charged with 3-(morpholin-4-ylmethyl)-5,6,7,8-tetrahydroquinoline (Preparation 16, 1.53 g) and anhydrous THF (35 mL). Upon dissolution, the reaction is cooled to −78° C. (external temp). Tert-butyllithium (4.50 mL of a 1.7 M THF solution) is added dropwise to the solution over a ten minute period. The solution is stirred at −78° C. for one hour, diethyl ethoxymethylenemalonate (1.53 g) is added drop-wise, and the contents of the flask are allowed to slowly warm to room temperature overnight (dry ice/acetone bath is not removed). The reaction mixture is quenched with 1N HCl and stirred. After the reaction mixture is stirred at room temperature for 30 min, the pH is adjusted to ca. 12 with 1 N NaOH (litmus), and the aqueous layer is extracted with MTBE (2×100 mL) and CH$_2$Cl$_2$ (1×100 mL). The combined organic layers are dried over Na$_2$SO$_4$, filtered, and concentrated. The crude product is flashed through a short plug of silica gel (2.5% methanol/CH$_2$Cl$_2$) to provide 1.8 g (80%) of the title compound as a yellow oil which is carried on into the next reaction without further characterization.

PREPARATION 18

Ethyl 6-(Morpholin-4-ylmethyl)-3-oxo-9,10-dihydro-3H,8H-pyrido[3,2,1-ij]quinoline-2-carboxylate [BQ.5]

A 250 mL round bottom flask equipped with a condenser is charged with ethanol (150 mL), triethylamine (0.93 mL) and diethyl 2-(ethoxy(3-(morpholin-4-ylmethyl)-5,6,7,8-tetrahydroquinolin-8-yl)methyl)malonate (Preparation 17, 750 mg). The solution is heated to reflux. After 12 h, the mixture is concentrated to give a yellow solid, which is purified by flash chromatography (silica gel, 6% MeOH:methylene chloride) to give 603 mg of the title compound. Physical characteristics: $^1$H NMR (DMSO-d$_6$): δ9.02, 8.04, 7.58, 4.24, 3.59, 3.57, 3.01, 2.88, 2.42, 1.89, 1.30; $^{13}$C NMR (DMSO-d$_6$): δ165.3, 154.1, 141.6, 138.3, 134.4, 132.8, 126.9, 125.3, 110.0, 104.3, 66.1, 59.7, 59.1, 52.9, 29.2, 27.8, 20.7, 14.3; IR (KBr) 3079, 3037, 2958, 2931, 2913, 2850, 2828, 1731, 1679, 1647, 1628, 1600, 1509, 1462, 1450, 1297, 1270, 1251, 1227, 1206, 1114, 1097, 1079; HRMS m/z 357.1818.

EXAMPLE 7

N-(4-Chlorobenzyl)-6-(morpholin-4-ylmethyl)-3-oxo-9,10dihydro-3H,8H-pyrido[3,2,1-ij]quinoline-2-carboxamide [BQ.6]

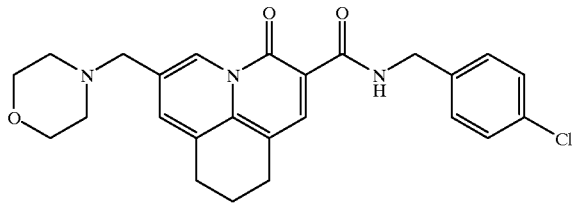

To a solution of 4-chlorobenzylamine (142 mg, delivered as a 1M methylene chloride solution) in anhydrous $CH_2Cl_2$ (3 mL), is added trimethylaluminum (482 μL, 2 M solution in heptane). After two hours at room temperature, ethyl 6-(morpholin-4-ylmethyl)-3-oxo-9,10-dihydro-3H,8H-pyrido[3,2,1-ij]quinoline-2-carboxylate (Preparation 18, 327 mg) is added as a solid in one portion. Stirring is continued for 2.5 hours before quenching with 10 mL of a 35% aqueous solution of Rochelle's salt. This biphasic, gelatinous mixture is stirred for two hours before separating the layers and extracting the aqueous layer five times with $CH_2Cl_2$. The resulting solution is concentrated in vacuo to give a bright yellow solid which is recrystallized from acetone (reflux, 62 mL/g) to afford 251 mg (73%) of the title compound as a canary yellow solid. Physical characteristics: M.p. 200–201° C.; $^1H$ NMR ($CDCl_3$); δ10.2, 9.07, 8.54, 7.41, 7.33, 7.28, 4.67, 3.71, 3.53, 3.02, 2.48, 2.02; $^{13}C$ NMR ($CDCl_3$): δ165.5, 157.5, 140.6, 138.6, 137.7, 134.7, 132.7, 130.9, 129.0, 128.6, 127.1, 125.2, 113.1, 109.2, 66.8, 60.4, 53.6, 42.9, 30.4, 28.7, 21.3; HRMS m/z 452.1747 ($C_{25}H_{26}ClN_3O_3$+H).

EXAMPLE 8

N-(4-Chlorobenzyl)-3-methyl-9-(4-morpholinylmethyl)-2,7-dioxo-2,3-dihydro-1H,7H-pyrido[1,2,3-de]quinoxaline-6-carboxamide hydrobromide [AC.1, R=methyl]

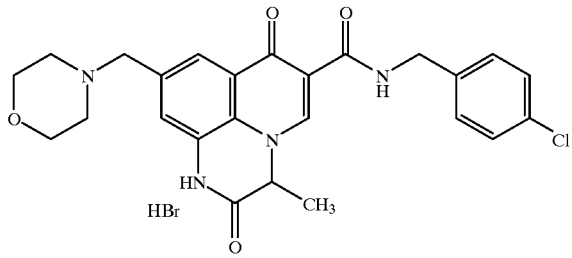

2-Bromopropionyl bromide (320 mg) is slowly added to a solution of 8-amino-N-(4-chlorobenzyl)-4-hydroxy-6-(4-morpholinomethyl)-3-quinolinecarboxamide (Preparation 3, 130 mg) and pyridine (50 mg) in NMP (1 mL). After 30 min, methanol (1 mL) and triethylamine (500 mg) are added. Water (2 mL) is added and the precipitate (103 mg) of the title compound is filtered off and washed with water and ether and dried under vacuum. Physical characteristics: $^1H$ NMR (DMSO-$d_6$) δ1.59, 3.18, 3.36, 3.65, 3.95, 4.52, 4.57, 5.39, 7.3–7.45, 8.03, 8.94, 10.0, 10.2,11.5. Anal. Found ($C_{31}H_{29}ClN_4O_6$.HBr.$H_2O$): C, 52.03; H, 4.95; N, 9.64; Cl, 6.09.

EXAMPLE 9

N-(4-Chlorobenzyl)-10-(4-morpholinylmethyl)-2,8-dioxo-1,2,3,4-tetrahydro-8H-[1,4]diazepino[3,2,1-ij]quinoline-7-carboxamide [BH.2]

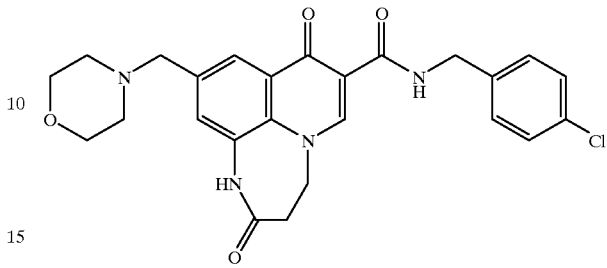

Acryloyl chloride (600 mg) is slowly added to a solution of 8-amino-N-(4-chlorobenzyl)-4-hydroxy-6-(4-morpholinomethyl)-3-quinolinecarboxamide (Preparation 3, 142 mg). After 30 min, the product is partitioned between ethyl acetate and water. The aqueous phase is extracted repeatedly with chloroform, and the organic extracts are evaporated to give 123 mg of 8-(acryloylamino)-N-(4-chlorobenzyl)-4-hydroxy-6-(4-morpholinylmethyl)-3-quinolinecarboxamide. A portion of this product (90 mg) is heated in Dowtherm A (0.8 mL) at 220° C. for 90 min. The reaction mixture is applied to a silica gel column, which is eluted with 1 to 6% methanol/chloroform to give 45 mg of the title compound, which is crystallized from ethyl acetate. Physical characteristics: M.p. 235–240° C.; $^1H$ NMR ($CDCl_3$) δ2.51, 3.16, 3.63, 3.72, 4.61, 4.66, 7.34, 7.51, 8.27, 8.48, 8.79, 10.3.

EXAMPLE 10

2-(Benzylamino)-N-(4-chlorobenzyl)-9-(4-morpholinylmethyl)-7-oxo-3H,7H-pyrido[1,2,3-de]quinoxaline-6-carboxamide [BG.1, Y=morpholinylmethyl, $R^{10}$=benzyl]

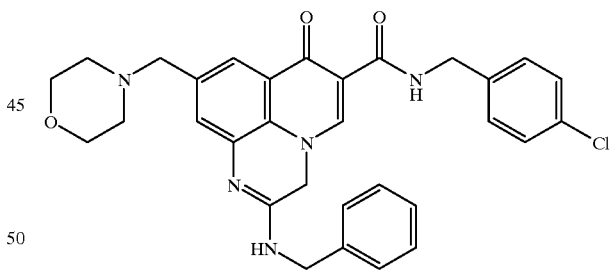

N-(4-Chlorobenzyl)-9-(4-morpholinylmethyl)-2,7-dioxo-2,3-dihydro-1H,7H-pyrido[1,2,3-de]quinoxaline-6-carboxamide (Example 3, 30 mg) is heated under reflux with benzylamine (0.5 mL) for 18 h. The benzylamine is evaporated and the product is triturated with ether to give the title compound (18 mg), which is crystallized from ethyl acetate. Physical characteristics: M.p. 235–240° C.; $^1H$ NMR ($CDCl_3$) δ2.36, 3.51, 3.57, 4.55, 4.63, 7.2–7.5, 7.64, 8.20, 8.62, 10.5; HRMS m/z 555.2128 ($C_{31}H_{30}ClN_5O_3$).

PREPARATION 19

2,3-Difluoro-5-iodobenzoic acid [J.2]

A 500 mL, 3 neck round bottom flask, equipped with an overhead stirrer is charged with trifluoromethanesulfonic acid (100 g), cooled to 0–5° C. in an ice bath, and treated with 2,3-difluorobenzoic acid (18.96 g). To this mixture is added N-iodosuccinimide (32.4 g) portion-wise over a 10 min period. After an additional 3 min, the cooling bath is removed and the reaction mixture is allowed to warm to room temperature. After a total of 5 h, the reaction mixture is poured into 600 mL of vigorously stirred crushed ice/water containing 100 mL of 10% sodium sulfite solution. The beige colored precipitate is collected, washed with ice water and dried at 50° C. in a vacuum oven overnight to produce 28.2 g (83%) of the title compound. Physical characteristics: $^1$H NMR (CDCl$_3$) δ10.35, 8.12, 7.76; MS (ESI−) m/z 283 (M−H)$^−$.

PREPARATION 20

Ethyl 3-(2,3-Difluoro-5-iodophenyl)-3-oxopropanoate [H.1, Y=Iodo]

2,3-Difluoro-5-iodobenzoic acid (Preparation 19, 18.2 g) in tetrahydrofuran (100 mL) at room temperature is treated with 1,1'-carbonyldiimidazole (12.46 g) portion-wise over a one minute period under a nitrogen atmosphere and the mixture is stirred for 6 h. In a separate flask, ethyltrimethylsilyl malonate (14.38 g) in tetrahydrofuran (40 mL) is cooled to 0–5° C. and DBU (11.20 g) is added dropwise over a period of 15 minutes. After 5.5 h, this solution is cannulated into the ice cooled imidazolide solution over a 7 minute period with vigorous stirring. The mixture is allowed to slowly warm to room temperature overnight. The reaction mixture is poured into 600 mL of ice/water containing 41 mL of 6N HCl. The mixture is extracted 3 times with ethyl acetate. The combined organic extracts are dried (Na$_2$SO$_4$) and concentrated in vacuo. The crude product is purified by chromatography, using 600 g of silica gel, packed and eluted with methylene chloride/heptane/ethyl acetate/acetic acid (3/7/0.5%/0.5%), to afford the title compound in 65% yield as an orange oily solid. Physical characteristics: $^1$H NMR (CDCl$_3$) δ12.65, 8.00, 7.94, 7.73, 7.58, 5.81, 4.35–4.19, 3.96, 1.35, 1.28; IR (diffuse reflectance) 2986, 1647, 1622, 1573, 1489, 1420, 1383, 1293, 1275, 1240, 1215, 1037, 958, 882, 801 cm$^{-1}$; MS (EI) m/z 354 (M$^+$); HRMS (FAB) m/z 354.9648 (C$_{11}$H$_9$F$_2$IO$_3$+H). Anal. Found: C, 37.34; H, 2.50; N, 0.15.

PREPARATION 21

Ethyl 2-(2,3-Difluoro-5-iodobenzoyl)-3-ethoxy-2-propenoate [AE.1]

A flask equipped with a Dean-Stark trap and cold water condenser, is charged with ethyl 3-(2,3-difluoro-5-iodophenyl)-3-oxopropanoate (Preparation 20, 14.8 g), triethylorthoformate (12.4 g), and acetic anhydride (14.92 g). The contents are placed in an oil bath initially at 115° C. and the temperature quickly raised to 150° C. where it is maintained until the volume of ethyl acetate and ethanol distillate collected remained constant (ca. 1.25 h). The reaction mixture is cooled and concentrated at reduced pressure to obtain 16.86 g (98.5%) of the title compound as a dark golden oil. Physical characteristics: $^1$H NMR (CDCl$_3$) δ8.98, 7.87–7.75, 7.71, 7.69–7.51, 4.36, 4.29–4.08, 3.75, 1.48, 1.35, 1.26, 1.21–1.02; MS (ESI+) m/z 411 (M+H)$^+$.

PREPARATION 22

Ethyl 9-iodo-1-methyl-2,7-dioxo-2,3-dihydro-1H,7H-pyrido[1,2,3-de]quinoxaline-6-carboxylate. [AG.1]

Glycine methylamide (1.0 g) is added at room temperature to a solution of ethyl 2-(2,3-difluoro-5-iodobenzoyl)-3-ethoxy-2-propenoate (Preparation 21, 2.0 g) in NMP (20 mL). Sodium hydride (400 mg, 60% dispersion in mineral oil) is added in two portions to the solution, and the solution is heated at 100° C. for 30 min. The product is partitioned between chloroform and water, the chloroform phase is concentrated and applied to a silica gel column with 1–2% methanol chloroform as the eluant. The purified fractions are triturated with ether to give 1.22 g of the title compound. Physical characteristics: M.p. 278–283° C.; $^1$H NMR (DMSO-d$_6$) δ1.29, 3.63, 4.23, 5.10, 7.65, 8.09, 8.55. Anal. Found: C, 43.49; H, 3.18; N, 6.75.

PREPARATION 23

N-(4-Chlorobenzyl)-9-iodo-1-methyl-2,7-dioxo-2,3-dihydro-1H,7H-pyrido[1,2,3-de]quinoxaline-6-carboxamide. [AG.2]

A mixture of ethyl 9-iodo-1-methyl-2,7-dioxo-2,3-dihydro-1H,7H-pyrido[1,2,3-de]quinoxaline-6-carboxylate (Preparation 22, 400 mg) is stirred at 180° C. in 4-chlorobenzylamine (2.0 mL) for 1 h. The mixture is cooled and diluted with acetonitrile to give 412 mg of the title compound. Physical characteristics: M.p. 278–283° C.; $^1$H NMR (DMSO-d$_6$) δ3.38, 4.55, 5.21, 7.35, 7.39, 7.69, 8.18, 8.76, 10.12. Anal. Found: C, 47.43; H, 3.01; N, 8.32; Cl, 7.14.

EXAMPLE 11

N-(4-Chlorobenzyl)-9-(3-hydroxy-1-propynyl)-1-methyl-2,7-dioxo-2,3-dihydro-1H,7H-pyrido[1,2,3-de]quinoxaline-6-carboxamide. [AH.1]

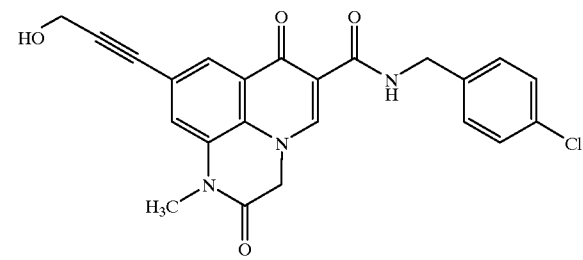

Propargyl alcohol (50 mg), cuprous iodide (50 mg) and a solution of PdCl$_2$(PPh$_3$)$_2$ (1 mL, 0.15 M in THF) are added to a suspension of N-(4-chlorobenzyl)-9-iodo-1-methyl-2,7-dioxo-2,3-dihydro-1H,7H-pyrido[1,2,3-de]quinoxaline-6-carboxamide (Preparation 23, 250 mg) in diethylamine (2.0 mL). The reaction is stirred for 90 min and the product is then extracted into chloroform and is chromatographed on silica gel. The desired product is eluted with 20% methanol/chloroform. Physical characteristics: $^1$H NMR (DMSO-d$_6$) δ3.40, 4.36, 4.56, 5.22, 5.42, 7.36, 7.40, 7.44, 7.88, 8.76, 10.2. HRMS m/z 436.1064 (C$_{23}$H$_{18}$ClN$_3$O$_4$).

PREPARATION 24

Diethyl 2-((2-(Hydroxymethyl)-4-methylanilino)methylene)malonate. [AV.2]

A mixture of 2-(hydroxymethyl)-4-methylaniline (10.0 g) and diethyl ethoxymethylenemalonate (18.5 g) is heated at 110° C. for 1 h. Crystallization from ether/hexane afforded 19.5 g of the title compound. Physical characteristics: M.p. 92–95° C.; Anal. Found: C, 62.49; H, 6.88; N, 4.60.

PREPARATION 25

Ethyl 8-((Acetyloxy)methyl)-4-hydroxy-6-methyl-3-quinolinecarboxylate [AV.4]

A mixture of diethyl 2-((2-(hydroxymethyl)-4-methylanilino)methylene)malonate (Preparation 24, 5.0 g) and acetic anhydride (5.0 mL) is heated at 130° C. for 1 h. The acetic anhydride is evaporated, and the residual solid is heated at reflux in diphenyl ether (20 ml) for 1 h. The solution is cooled and diluted with acetonitrile (5 mL) and ether (15 mL). The resulting precipitate is filtered to afford 1.8 g of the title compound.

PREPARATION 26

3-Ethyl 1-Isobutyl 8-((acetyloxy)methyl)-6-methyl-4-oxo-1,3(4H)-quinolinedicarboxylate [AV.5]

Sodium hydride (3.1 g, 60% dispersion) is added at 0° C. to a stirred solution of ethyl 8-((acetyloxy)methyl)-4-hydroxy-6-methyl-3-quinolinecarboxylate (Preparation 25, 29.6 g) in N-methylpyrrolidinone (250 ml). The solution is allowed to warm to room temperature over 10 min and isobutyl chloroformate (25.5 g) is then added. After 30 min, acetic acid (3.6 g) is added. The solvent is evaporated under reduced pressure, and the residual oil is partitioned between ethyl acetate and water. The ethyl acetate layer is concentrated to give an oil. The crude product is dissolved in ethyl acetate (50 ml) and is chromatographed on silica gel with 10% ethyl acetate/hexane as the initial eluant to give 19.5 g of the title compound. A sample is recrystallized from ethyl acetate/hexane for analysis. Physical characteristics: M.p. 101–103° C.; $^1$H NMR (CDCl$_3$) δ1.05, 1.44, 2.12, 2.18, 2.59, 4.15, 4.45, 5.82, 7.74, 7.88, 9.40. Anal. Found: C, 62.42; H, 6.34; N, 3.45.

PREPARATION 27

Ethyl 8-Formyl-4-hydroxy-6-(4-morpholinylmethyl)-3-quinolinecarboxylate [AV.6]

A stirred solution of 3-ethyl 1-isobutyl 8-((acetyloxy)methyl)-6-methyl-4-oxo-1,3-(4H)-quinolinedicarboxylate (Preparation 26, 3.0 g) and N-bromosuccinimide (3.0 g) in dichloromethane (300 mL) is irradiated with a 650 watt sun lamp for 20 min. Morpholine (15 mL) is added to the solution. After 10 min, ethanol (20 mL) is added, and the solvents are removed at 50° C./20 mm. The reaction is repeated on the same scale. The reaction mixtures are combined and partitioned between chloroform (250 mL) and water (150 mL). The chloroform layer is washed twice with water, and the chloroform is evaporated. The residual oil is chromatographed on silica gel (1% methanol/chloroform) to give 2.15 g of the title compound. Physical characteristics: M.p. 202–204° C.; $^1$H NMR (CDCl$_3$) δ1.43, 2.50, 3.69, 3.74, 4.42, 8.19, 8.59, 8.67, 10.18, 11.8. Anal. Found: C, 62.42; H, 5.92; N, 8.03.

PREPARATION 28

Ethyl 8-((Benzylamino)methyl)-4-hydroxy-6-(4-morpholinylmethyl)-3-quinolinecarboxylate [AV.7]

Sodium triacetoxyborohydride (1.0 g) is added to a stirred solution of ethyl 8-formyl-4-hydroxy-6-(4-morpholinylmethyl)-3-quinolinecarboxylate (Preparation 27, 515 mg), benzylamine (340 mg) and acetic acid (360 mg) in a mixture of ethanol/THF (10 mL, 1/1). The solution is stirred for 90 min. The solvents are evaporated. The residue is taken up in chloroform and is applied to a silica gel column which is eluted with 1–3% methanol/chloroform followed by 4% methanol/chloroform to afford 697 mg of the title compound which is crystallized from methanol/ether. Physical characteristics: $^1$H NMR (CDCl$_3$) δ1.43, 2.47, 3.59, 3.72, 3.90, 4.26, 4.42, 7.34, 7.51, 8.23, 8.59. Anal. Found: C, 68.59; H, 6.65; N, 9.64.

PREPARATION 29

8-((Benzylamino)methyl)-N-(4-chlorobenzyl)-4-hydroxy-6-(4-morpholinylmethyl)-3-quinolinecarboxamide [AV.8]

A mixture of ethyl 8-((benzylamino)methyl)-4-hydroxy-6-(4-morpholinylmethyl)-3-quinolinecarboxylate (Preparation 28, 513 mg) and 4-chlorobenzylamine (2.5 mL) is heated at 200° C. for 20 min. The mixture is concentrated, and the remaining oil is taken up in chloroform and applied to a silica gel column. The column is eluted with 1% methanol/chloroform followed by 2–4% methanol/chloroform to afford 483 mg of the title compound after crystallization from ethyl acetate/ether. Physical characteristics: M.p. 214–216° C.; $^1$H NMR (CDCl$_3$) δ2.46, 3.59, 3.71, 3.86, 4.28, 4.67, 7.28–7.43, 7.53, 8.25, 8.84, 10.5. Anal. Found: C, 67.68; H, 5.89; N, 10.52; Cl, 6.64.

EXAMPLE 12

2-Benzyl-N-(4-chlorobenzyl)-9-(4-morpholinylmethyl)-7-oxo-2,3-dihydro-1H,7H-pyrido[3,2,1-ij]quinazoline-6-carboxamide [AV.9]

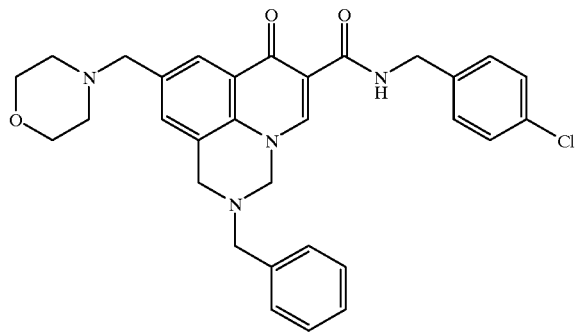

Aqueous formaldehyde (0.25 ml, 37% solution) is added to a solution of 8-((benzylamino)methyl)-N-(4-chlorobenzyl)-4-hydroxy-6-(4-morpholinylmethyl)-3-quinolinecarboxamide (Preparation 29, 60 mg) in methanol (2.5 mL) at 50° C. The solution is allowed to cool and the resulting precipitate is filtered and washed with methanol to give 38 mg of the title compound. Physical characteristics: M.p. 203–205° C.; $^1$H NMR (DMSO-d$_6$) δ2.38, 3.57, 3.73, 4.20, 4.57, 5.29, 7.2–7.4, 7.51, 8.08, 8.74, 10.4. Anal. Found: C, 68.50; H, 5.72; N, 10.29.

EXAMPLE 13

2-Benzyl-N-(4-chlorobenzyl)-9-(4-morpholinylmethyl)-3,7-dioxo-2,3-dihydro-1H,7H-pyrido[3,2,1-ij]quinazoline-6-carboxamide [AW.1]

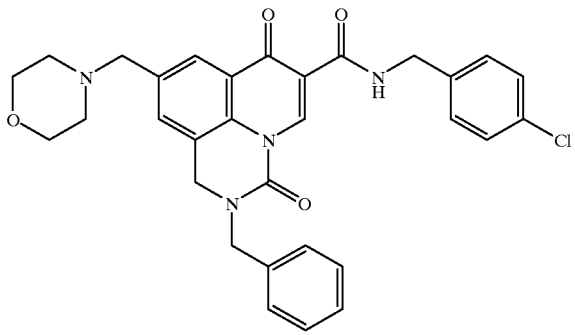

A solution of 1,1'-carbonyldiimidazole (82 mg) in NMP (2.0 mL) is added over 15 min to a solution of 8-((benzylamino)methyl)-N-(4-chlorobenzyl)-4-hydroxy-6-(4-morpholinylmethyl)-3-quinolinecarboxamide (Preparation 29, 106 mg) in NMP (6 mL). After an additional 15 min, the solvent is removed under reduced pressure and the residual solid is triturated with methanol to afford 93 mg of the title compound. Physical characteristics: M.p. 201–204° C.; $^1$H NMR (CDCl$_3$) δ2.44, 3.58, 3.70, 4.67, 4.73, 4.87, 7.3–7.45, 7.51, 8.19, 9.90, 10.1; Anal. Found: C, 66.67; H, 5.31; N, 9.99; Cl, 6.35.

EXAMPLE 14

2-Benzyl-N-(4-chlorobenzyl)-10-(4-morpholinylmethyl)-3,8-dioxo-1,2,3,4-tetrahydro-8H-[1,4]diazepino[6,7,1-ij]quinoline-7-carboxamide [BN.1]

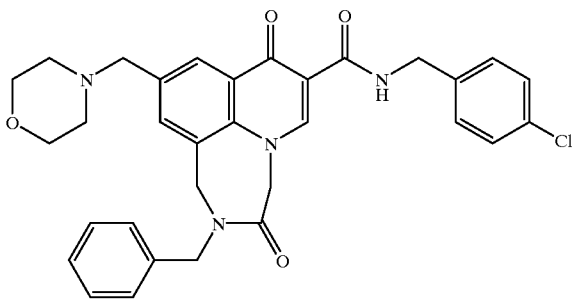

Bromoacetic anhydride (40 mg) is added to a stirred solution of 8-((benzylamino)methyl)-N-(4-chlorobenzyl)-4-hydroxy-6-(4-morpholinylmethyl)-3-quinolinecarboxamide (Preparation 29, 53 mg) in NMP (0.3 mL). After 30 min, triethylamine (50 mg) is added. The solution is diluted with water and the resulting precipitate is filtered and dried under vacuum to give 44 mg of the title compound. Physical characteristics: HRMS m/z 571.2104 (C$_{32}$H$_{31}$ClN$_4$O$_4$).

PREPARATION 30

Ethyl 2-(2,3-Difluoro-5-iodobenzoyl)-3-(2-formyl-2-methylhydrazino)prop-2-enoate [H.2]

A solution of 1-formyl-1-methylhydrazine (0.217 g) in toluene (0.5 mL) is added to a solution of ethyl 2-(2,3-difluoro-5-iodobenzoyl)-3-ethoxy-2-propenoate (Preparation 21, 1.00 g) in toluene (2.5 mL) at 33° C. After stirring at ambient temperature for 20 minutes, a precipitate formed and an additional 1.5 mL of toluene is added. After an additional 1.75 h, solid anhydrous Na$_2$CO$_3$ (0.285 g) is added and the reaction mixture is heated to reflux. After 1 h, the reaction mixture is concentrated at reduced pressure and the residue suspended in 8 mL of water which is used as is in the following step. Physical characteristics: MS (ESI+) m/z 419 (M+H)$^+$.

PREPARATION 31

9-Iodo-3-methyl-7-oxo-2,3-dihydro-7H-[1,3,4]oxadiazino[6,5,4-ij]quinoline-6-carboxylic acid [H.3]

Ethyl 2-(2,3-difluoro-5-iodobenzoyl)-3-(2-formyl-2-methylhydrazino)prop-2-enoate (Preparation 30, 1.02 g) in 8 mL of water is treated with KOH pellets (0.410 g) and the reaction mixture is heated in an oil bath, under a nitrogen atmosphere, at 105° C. for 1.75 h while volatiles were condensed into a Dean-Stark trap. At this time, the Dean-Stark trap was removed, 1 mL of an aqueous solution of KOH (0.956 g) is added to the mixture, and heating is continued at 105° C. for 4 days. The mixture is cooled to room temperature, treated with formic acid (1.68 g), and is warmed to 45–50° C. A 37% aqueous formaldehyde (0.396 g) is added and the mixture is heated at 70° C. for 30 minutes. The resulting slurry is cooled in an ice bath at 0–5° C., reacted with 29% aqueous ammonium hydroxide (1.46 mL), and allowed to warm to room temperature where it is stirred for 35–40 minutes. Charcoal (44 mg) is added to the mixture which is stirred for 30 minutes and filtered through a pad of solka-floc rinsing with water. The filtrate is diluted with saturated brine and a mixture of chloroform/methanol (95/5) and filtered through a pad of solka-floc. The organic layer is separated, dried with anhydrous sodium sulfate, and concentrated at reduced pressure to obtain 252 mg (28%) of the title compound. Physical characteristics: MS (ESI+) m/z 373 (M+H)$^+$.

PREPARATION 32

N-(4-Chlorobenzyl)-9-iodo-3-methyl-7-oxo-2,3-dihydro-7H-[1,3,4]oxadiazino[6,5,4-ij]quinoline-6-carboxamide [H.4]

A solution of 9-iodo-3-methyl-7-oxo-2,3-dihydro-7H-[1,3,4]oxadiazino[6,5,4-ij]quinoline-6-carboxylic acid (Preparation 31, 0.900 g) in tetrahydrofuran (25 mL) is refluxed with 1,1'-carbonyldiimidazole (0.631 g) for 5 h. The reaction mixture is cooled to room temperature and treated with 4-chlorobenzylamine (0.828 g). The reaction mixture is diluted with ether (75 mL), filtered, and the filtrate is concentrated at reduced pressure. The crude product is purified by chromatography, using 75 g of silica gel packed and eluted with EtOAc/CH$_2$Cl$_2$/heptane (1/4/5), to afford a 57% yield of the title compound. Physical characteristics: $^1$H NMR (DMSO-d$_6$) δ10.15, 8.67, 8.12, 7.75, 7.37, 5.29, 4.54, 2.98; MS (EI) m/z 495 (M+); HRMS (FAB) m/z 495.9935 (C$_{19}$H$_{15}$ClIN$_3$O$_3$+H). Anal. Found: C, 45.97; H, 3.14; N, 8.39.

EXAMPLE 15

N-(4-Chlorobenzyl)-9-(3-hydroxyprop-1-ynyl)-3-methyl-7-oxo-2,3-dihydro-7H-[1,3,4]oxadiazino[6,5,4-ij]quinoline-6-carboxamide [I.1, $R^7$=methyl]

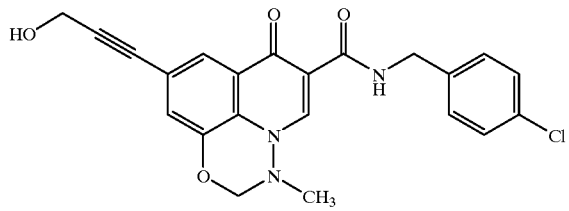

A dry flask is charged with N-(4-chlorobenzyl)-9-iodo-3-methyl-7-oxo-2,3-dihydro-7H-[1,3,4]oxadiazino[6,5,4-ij]quinoline-6-carboxamide (Preparation 32, 0.100 g), cuprous iodide (0.012 g), dichlorobistriphenylphosphine palladium (0.0072 g), propargyl alcohol (0.022 g), and diethylamine (4 mL). The reaction mixture is stirred at room temperature for 5 h and concentrated at reduced pressure. The residue is chromatographed, using 20 g of silica gel packed and eluted with EtOAc/CH$_2$Cl$_2$ (1/1), to obtain the title compound in 80% yield. Physical characteristics: M.p. 231–233° C.; MS (ESI+) m/z 424.0 (M+H$^+$); HRMS (FAB) m/z 424.1078 (C$_{22}$H$_{18}$ClN$_3$O$_4$+H).

PREPARATION 33 tert-Butyl 2-(2-(2,3-difluoro-5-iodobenzoyl)-3-ethoxy-3-oxoprop-1-enyl)-1-methylhydrazinecarboxylate [AM.1, Y=iodo]

A solution of ethyl 2-(2,3-difluoro-5-iodobenzoyl)-3-ethoxy-2-propenoate (Preparation 21, 7.80 g) in tert-butanol (40 mL) is cooled with a cold water bath and a solution of tert-butyl 1-methylhydrazinecarboxylate (2.92 g) in tert-butanol (4 mL) is added. The cooling bath is removed, the mixture is stirred for 5 min at ambient temperature, and then is heated in an oil bath at 45° C. for 40 min. The reaction mixture is poured into 100 mL of crushed ice/water and extracted two times with ethyl acetate. The combined organic layers are dried (Na$_2$SO$_4$) and concentrated in vacuo. The crude product is purified by chromatography, using 300 g of silica gel, packed and eluted with EtOAc/heptane (1/3), to afford 8.95 g (92%) of the title compound as a yellow oily foam. Physical characteristics: $^1$H NMR (CDCl$_3$) δ8.14, 8.07, 7.59–7.49, 7.46–7.41, 4.07, 3.30, 3.26, 1.50, 1.09, 0.97; MS (ESI+) m/z 511 (M+H)$^+$.

PREPARATION 34

Ethyl 1-((tert-Butoxycarbonyl)(methyl)amino)-8-fluoro-6-iodo-4-oxo-1,4-dihydroquinoline-3-carboxylate [AM.2, Y=iodo]

Sodium hydride (0.256 g, 60% oil dispersion) is added to a solution of tert-butyl 2-(2-(2,3-difluoro-5-iodobenzoyl)-3-ethoxy-3-oxoprop-1-enyl)-1-methylhydrazinecarboxylate (Preparation 33, 3.20 g) in N,N-dimethylformamide (18 mL) at room temperature, and the mixture is stirred for 2 h. The reaction mixture is poured into a mixture of 100 mL of ice water and 100 mL of saturated brine. The mixture is extracted 3 times with ethyl acetate. The combined organic layers are dried (Na$_2$SO$_4$) and concentrated under a nitrogen stream overnight. The crude product is purified by chromatography, using 200 g of silica gel packed and eluted with acetone/CH$_2$Cl$_2$/heptane (1/3/6), provided 2.76 g (90%) of the title compound as a white foam. Physical characteristics: $^1$H NMR (CDCl$_3$) δ8.50, 8.31, 7.67, 4.32, 3.37, 1.49, 1.34, 1.25; $^{13}$C NMR (CDCl$_3$) δ168.87, 163.97, 160.01, 155.50, 141.76, 131.84, 131.37, 128.46, 127.24, 110.98, 86.73, 78.64, 61.47, 36.09, 28.00, 14.64; MS (ESI+) m/z 491 (M+H)$^+$; TLC (silica gel GF): R$_f$=0.44 acetone/CH$_2$Cl$_2$/hexane (1/1/3).

PREPARATION 35

Ethyl 8-Fluoro-6-iodo-1-(methylamino)-4-oxo-1,4-dihydroquinoline-3-carboxylate [AM.3, Y=iodo]

A solution of trifluroacetic acid (6.40 g) in methylene chloride (5 mL) is added dropwise over a 4 minute period to a solution of ethyl 1-((tert-butoxycarbonyl)(methyl)amino)-8-fluoro-6-iodo-4-oxo-1,4-dihydroquinoline-3-carboxylate (Preparation 34, 1.10 g) in methylene chloride (20 mL) at room temperature. After 3.5 h, the mixture is poured into a mixture of saturated sodium bicarbonate solution (125 mL) and water (50 mL), and extracted two times with ethyl acetate. The combined organic extracts are dried (Na$_2$SO$_4$) and concentrated at reduced pressure. The resulting gummy solid is stirred with diethyl ether at room temperature to afford 0.857 g (98%) of the title compound as a white solid.

PREPARATION 36

Ethyl 8-Fluoro-1-((hydroxymethyl)(methyl)amino)-6-iodo-4-oxo-1,4-dihydroquinoline-3-carboxylate [AM.4, Y=iodo]

A mixture of ethyl 1-((tert-butoxycarbonyl)(methyl)amino)-8-fluoro-6-iodo-4-oxo-1,4-dihydroquinoline-3-carboxylate (Preparation 35, 0.200 g), 37% aqueous formaldehyde (4.0 mL), and water (2.0 mL) is heated in an oil bath for 2.5 h at 85° C. The mixture is cooled, diluted with ice water (30 mL), and the resulting precipitate is collected, rinsed with ice water and partially air dried. The solid is dissolved in a mixture of acetone and CH$_2$Cl$_2$, dried (Na$_2$SO$_4$), and concentrated at reduced pressure to yield 0.194 g (90%) of the title compound as a white solid. Physical characteristics: MS (ESI+) m/z 421 (M+H)$^+$; TLC (silica gel GF): R$_f$=0.32 acetone/CH$_2$Cl$_2$ (1/4).

PREPARATION 37

Di(tert-butyl) 2-(((3-(ethoxycarbonyl)-8-fluoro-6-iodo-4-oxoquinolin-1(4H)-yl](methyl)amino)methyl)malonate [AM.5, Y=iodo]

Thionyl chloride (0.122 g) is added to a solution of ethyl 8-fluoro-1-((hydroxymethyl) (methyl)amino)-6-iodo-4-oxo-1,4-dihydroquinoline-3-carboxylate (Preparation 36, 0.194 g) suspended in tetrahydrofuran (4 mL) at room temperature, and the mixture is stirred for 4.5 h. The reaction mixture is twice suspended in toluene and concentrated on a rotary evaporator, and the remaining volatiles removed at high vacuum. The resulting white solid is suspended in tetrahydrofuran (3 mL), cooled to 0–5° C. in an ice bath, and treated with sodium hydride (0.040 g, 60% oil dispersion) under a nitrogen atmosphere. After 30 min, the reaction mixture is treated with a separately prepared mixture of the anion of di-tert-butylmalonate by treating di-tert-butylmalonate (0.116 g) with sodium hydride (0.021 g) at 0–5° C. for a period of 1 h. The combined intermediates are stirred at 0–5° C. for 1.5 h. The mixture is diluted with 20 mL of pH 7 buffer, treated with 6N HCl to bring the pH to 7, and extracted once with ethyl acetate. The organic layer is washed with saturated brine, dried (Na$_2$SO$_4$), and concentrated at reduced pressure. Chromatography with 30 g of silica gel, packed and eluted with EtOAc/CH$_2$Cl$_2$ (1/5), gives 0.227 g (80%) of the title compound. Physical characteristics: $^1$H NMR (CDCl$_3$) δ8.60, 7.68, 4.41, 3.60, 3.28, 3.00, 1.42, 1.42; MS (ESI+) m/z 619 (M+H)$^+$; TLC (silica gel GF): R$_f$=0.46 EtOAc/CH$_2$Cl$_2$ (1/4).

PREPARATION 38

3,3-Di(tert-butyl) 8-Ethyl 5-iodo-1-methyl-7-oxo-1,2-dihydro-3H,7H-pyrido[3,2,1-ij]cinnoline-3,3,8-tricarboxylate [AM.6, Y=iodo]

Cesium carbonate (0.367 g) is added to a solution of di(tert-butyl) 2-(((3-(ethoxycarbonyl)-8-fluoro-6-iodo-4-oxoquinolin-1(4H)-yl)(methyl)amino)methyl)malonate (Preparation 37, 0.517 g) in dimethylsulfoxide (5 mL) and the mixture is heated at 85° C. in an oil bath under a nitrogen atmosphere for 2 h. The mixture is cooled in an ice bath, diluted with 65 mL of water containing 2.5 mL of acetic acid, stirred, and the resultant yellow precipitate collected and dried in a vacuum oven to provide the title compound in 75% yield as a golden oil. Physical characteristics: $^1$H NMR (CDCl$_3$) δ8.79, 8.54, 8.29, 4.40, 4.16, 2.78, 1.51, 1.41; MS (ESI+) m/z 599 (M+H)$^+$; TLC (silica gel GF): R$_f$=0.59 acetone/CH$_2$Cl$_2$ (1/4).

PREPARATION 39

5-Iodo-1-methyl-7-oxo-2,3-dihydro-1H,7H-pyrido[3,2,1-ij]cinnoline-8-carboxylic acid [AM.7, Y=iodo]

A mixture of acetic acid (1 mL), 6N HCl (1 mL), and 3,3-di(tert-butyl) 8-ethyl 5-iodo-1-methyl-7-oxo-1,2-dihydro-3H,7H-pyrido[3,2,1-ij]cinnoline-3,3,8-tricarboxylate (Preparation 38, 0.165 g) is heated in an oil bath at 110° C. for 1.5 h. Additional acetic acid (1 mL) and 6N HCl (1 mL) is added and heating continued for 2 h. The reaction vessel is purged with a strong nitrogen stream while heating in the oil bath at 115° C. until dry solid remains. Dimethylsulfoxide (2 mL) is then added and the temperature raised to 150° C. for 1 h. The mixture is allowed to cool slowly overnight. The mixture is diluted with chloroform, treated with 2 g of silica gel, and concentrated at reduced pressure. The residue is chromatographed using 35 g of silica gel, packed and eluted with acetone/chloroform/methanol/acetic acid (3/6.6/0.4/0.5%), to obtain 53 mg (52%) of the title compound as a tan colored solid. Physical characteristics: $^1$H NMR (DMSO-d$_6$) δ14.88, 8.80, 8.49, 8.18, 3.50, 3.15, 2.88; MS (ESI+) m/z 371 (M+H)$^+$; TLC (silica gel GF): R$_f$=0.46 acetone/chloroform/methanol/acetic acid (3/6.5/0.5/0.5%).

PREPARATION 40

N-(4-Chlorobenzyl)-5-iodo-1-methyl-7-oxo-2,3-dihydro-1H,7H-pyrido[3,2,1-ij]cinnoline-8-carboxamide [AM.8, Y=iodo, X=chloro]

A solution of 5-Iodo-1-methyl-7-oxo-2,3-dihydro-1H,7H-pyrido[3,2,1-ij]cinnoline-8-carboxylic acid (Preparation 39, 0.900 g) in tetrahydrofuran (25 mL) is refluxed with 1,1'-carbonyldiimidazole (0.631 g) for 5 h. The reaction mixture is cooled to room temperature and treated with 4-chlorobenzylamine (0.828 g). The reaction mixture is diluted with ether (75 mL), filtered, and the filtrate is concentrated at reduced pressure. The crude product is purified by chromatography, using 75 g of silica gel packed and eluted with EtOAc-CH$_2$Cl$_2$-heptane (1:4:5), to afford the title compound. Physical characteristics: $^1$H NMR (CDCl$_3$) δ8.91, 8.70, 7.87, 7.32, 4.65, 3.51, 3.13, 2.90; MS (ESI+) m/z 494.0; HRMS (FAB) m/z 494.0142 (C$_{20}$H$_{17}$ClIN$_3$O$_2$+H); TLC (silica gel GF): R$_f$=0.27 EtOAc/CH$_2$Cl$_2$ (1/6).

EXAMPLE 16

N-(4-Chlorobenzyl)-5-(3-hydroxyprop-1-ynyl)-1-methyl-7-oxo-2,3-dihydro-1H,7H-pyrido[3,2,1-ij]cinnoline-8-carboxamide [AN.1, X=chloro, Z=CH$_2$OH]

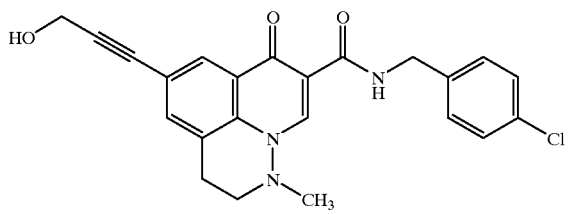

A dry flask is charged with N-(4-chlorobenzyl)-5-iodo-1-methyl-7-oxo-2,3-dihydro-1H,7H-pyrido[3,2,1-ij]cinnoline-8-carboxamide (Preparation 40, 0.100 g), cuprous iodide (0.012 g), dichlorobistriphenylphosphine palladium (0.0072 g), propargyl alcohol (0.022 g), and diethylamine (4 mL). The reaction mixture is stirred at room temperature for 5 h and concentrated at reduced pressure. The residue is chromatographed, using 20 g of silica gel packed and eluted with EtOAc/CH$_2$Cl$_2$ (1/1), to obtain the title compound in 74% yield as a tan colored solid. Physical characteristics: M.p. 165–167° C.; $^1$H NMR (DMSO-d$_6$) δ10.21, 8.67, 8.13, 7.74, 7.38, 5.41, 4.55, 4.35, 3.49, 3.12, 2.85; $^{13}$C NMR (DMSO-d$_6$) δ173.69, 162.80, 144.92, 137.79, 133.56, 132.88, 130.54, 128.44, 127.97, 127.49, 126.10, 124.99, 117.98, 109.97, 90.12, 81.73, 48.60, 47.63, 43.24, 40.64, 17.64; MS (ESI+) m/z 422 (M+H)$^+$; HRMS (FAB) m/z 422.1282 (C$_{23}$H$_{20}$ClN$_3$O$_3$+H); TLC (silica gel GF): R$_f$=0.22 acetone/chloroform (1/4).

Testing of Inventive Compounds

The antiviral activity of a compound of the invention can be determined using pharmacological models which are well known to the art, or using the test described below.

While many of the compounds of the present invention can demonstrate activity against the CMV polymerase, these compounds may be active against the cytomegalovirus by this or other mechanisms of action. Thus, the description below of these compounds' activity against the CMV polymerase is not meant to limit the present invention to a specific mechanism of action.

The HCMV polymerase assay is performed using a scintillation proximity assay (SPA) as described in several references, such as N. D. Cook, et al., Pharmaceutical Manufacturing International, pages 49–53 (1992); K. Takeuchi, Laboratory Practice, September issue (1992); U.S. Pat. No. 4,568,649 (1986); which are incorporated by reference herein. Reactions are performed in 96-well plates. The assay is conducted in 100 µl volume with 5.4 mM HEPES (pH 7.5), 11.7 mM KCl, 4.5 mM MgCl$_2$, 0.36 mg/ml BSA, and 90 nM $^3$H-dTTP. Assays are run with and without CHAPS, (3-[(3-Cholamidopropyl)-dimethylammonio]-1- propane-sulfonate) at a final concentration of 2 mM. HCMV polymerase is diluted in enzyme dilution buffer containing 50% glycerol, 250 mM NaCl, 10 mM HEPES (pH 7.5), 100 μg/ml BSA, and 0.01% sodium azide. The HCMV polymerase, which is expressed in recombinant baculovirus-infected SF-9 cells and purified according to literature procedures, is added at 10% (or 10 μl) of the final reaction volume, i.e., 100 μl. Compounds are diluted in 50% DMSO and 10 μl are added to each well. Control wells contain an equivalent concentration of DMSO. Unless noted otherwise, reactions are initiated via the addition of 6 nM biotinylated poly(dA)-oligo(dT) template/primer to reaction mixtures containing the enzyme, substrate, and compounds of interest. Plates are incubated in a 25° C. or 37° C. H$_2$O bath and terminated via the addition of 40 μl/reaction of 0.5 M EDTA (pH 8) per well. Reactions are terminated within the timeframe during which substrate incorporation is linear and varied depending upon the enzyme and conditions used, i.e., 30 min. for HCMV polymerase. Ten μl of streptavidin-SPA beads (20 mg/ml in PBS/10% glycerol) are added following termination of the reaction. Plates are incubated 10 min. at 37° C., then equilibrated to room temperature, and counted on a Packard Topcount. Linear regressions are performed and IC$_{50}$'s are calculated using computer software.

A modified version of the above HCMV polymerase assay is performed as described above, but with the following changes: Compounds are diluted in 100% DMSO until final dilution into assay buffer. In the previous assay, compounds are diluted in 50% DMSO. 4.5 mM dithiothreitol (DTT) is added to the polymerase buffer. Also, a different lot of CMV polymerase is used, which appears to be more active resulting in a more rapid polymerase reaction. Results of the testing of representative compounds of formula I in this assay are shown in Table 1 below.

TABLE 1

| Example | Polymerase IC$_{50}$ (μM) | | |
|---|---|---|---|
| | HCMV | HSV | VZV |
| 1 | 0.65 | nd | nd |
| 2 | 0.77 | 0.74 | 0.52 |
| 3 | 0.14 | <0.51 | 0.06 |
| 4 | 0.16 | nd | 0.18 |
| 5 | 3.2 | nd | nd |
| 6 | 4.0 | nd | nd |
| 7 | 4.0 | nd | nd |
| 8 | 0.43 | 0.2 | 0.09 |
| 9 | 0.67 | 0.28 | 0.17 |
| 10 | 0.31 | 0.31 | 0.12 |
| 11 | 1.16 | nd | nd |
| 12 | 1.67 | nd | nd |
| 13 | 39% @ 20 μM† | nd | nd |
| 14 | 6.0 | nd | nd |
| 15 | 4.19 | nd | nd |
| 16 | 7.95 | nd | nd | nd not determined.
†Percent inhibition at the given concentration.

Having described the invention in detail and by reference to the preferred embodiments thereof, it will be apparent that modifications and variations are possible without departing from the scope of the appended claims.

What is claimed is:
1. A compound of formula I,

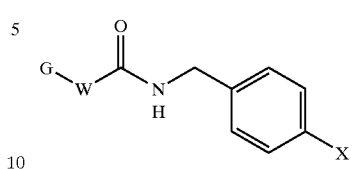

or a pharmaceutically acceptable salt thereof wherein,

X is Cl, Br, F, CN or NO$_2$;

G is
(a) C$_{1-4}$alkyl which is fully saturated or partially unsaturated and is substituted by hydroxy, or
(b) C$_{1-4}$alkyl substituted by NR$^1$R$^2$ or 4-tetrahydropyran;

R$^1$ is C$_{2-7}$alkyl substituted by hydroxy, C$_{1-4}$alkoxy, aryl, or heteroaryl;

R$^2$ is hydrogen or C$_{1-7}$alkyl; or

R$^1$ and R$^2$ together with the nitrogen to which they are attached form (a) a morpholine which may be optionally substituted by aryl or C$_{1-7}$alkyl, or (b) a pyrrolidine ring substituted by hydroxy;

W is a heterocycle of formula W1

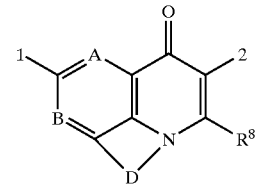

A is CR$^4$ or nitrogen;

B is CR$^5$ or nitrogen;

D is
(a) —(CR$^{13}$R$^{14}$)$_a$—, where a is 2 or 3
(b) —(CR$^{15}$R$^{16}$)$_4$—,
(c) —Y—CR$^{13}$R$^{14}$—CR$^{13}$R$^{14}$—,
(d) —CR$^{13}$R$^{14}$—Y—CR$^{13}$R$^{14}$—,
(e) —Y—CR$^{13}$R$^{14}$—Y—,
(f) —CR$^{13}$R$^{14}$—CR$^{13}$R$^{14}$—Y—,
(g) —Y—(CR$^{15}$R$^{16}$)$_n$—,
(h) —Y—CR$^{15}$=CR$^{15}$—,
(i) —Y—CR$^{15}$=N—,
(j) —CR$^{15}$=CR$^{15}$—Y—,
(k) —N=CR$^{15}$—Y—,
(l) —(CR$^{15}$R$^{16}$)$_b$—N=CR$^{15}$—, where b is 0 or 1
(m) —CR$^{15}$=N—(CR$^{15}$R$^{16}$)$_b$—, where b is 0 or 1
(n) —N=N—,
(o) —N=CR$^{15}$—(CR$^{15}$R$^{16}$)$_b$—, where b is 0 or 1
(p) —CR$^{15}$=CR$^{15}$—,
(q) —N=N—Y—,
(r) —Y—N=N—,
(s) —Y—N=CR$^{15}$—, or
(t) —CR$^{15}$R$^{16}$—Y—CR$^{15}$R$^{16}$—CR$^{15}$R$^{16}$—;

Y is oxygen, $S(O)_m$, or $NR^7$;
with the provisos that:
when G is $C_{1-4}$ alkyl which is fully saturated and is substituted by hydroxy or morpholinyl, in which morpholinyl is attached through nitrogen; A is $CR^4$; B is $CR^5$; and $R^8$ is hydrogen then at least one of $R^{13}$, $R^{14}$, or $R^7$ is not hydrogen or $C_{1-7}$alkyl;
when A is $CR^4$, B is $CR^5$, D is $—Y—CR^{13}R^{14}—CR^{13}R^{14}—$, and $R^8$ is hydrogen or $C_{1-7}$ alkyl then Y is not oxygen;
when A is $CR^4$, and B is $CR^5$ then D is not $—CR^{15l}=CR^{15}—$;
$R^4$ is H, halogen, or $C_{1-4}$alkyl optionally substituted by one to three halogens;
$R^5$ is
  (a) H,
  (b) halo,
  (c) $OR^{12}$,
  (d) $SR^{12}$,
  (e) $C_{1-7}$alkyl which may be partially unsaturated and optionally substituted by one or more substituents selected from $OR^{12}$, $SR^{12}$, $NR^{10}R^{11}$, or halo,
  (f) $C_{3-8}$cycloalkyl which may be partially unsaturated and is optionally substituted by one or more substituents selected from halogen, $OR^{12}$, $SR^{12}$, or $NR^{10}R^{11}$,
  (g) $(C=O)R^9$,
  (h) $S(O)_mR^9$,
  (i) $(C=O)OR^2$,
  (j) $NHSO_2R^9$,
  (k) nitro, or
  (l) cyano;
$R^7$ is
  (a) H,
  (b) $C_{1-7}$alkyl which may be partially unsaturated and optionally substituted by one or more substituents selected from $OR^{12}$, $SR^{12}$, $NR^{10}R^{11}$, or halo,
  (c) $C_{3-8}$cycloalkyl which may be partially unsaturated and is optionally substituted by one or more substituents selected from halogen, $OR^{12}$, $SR^{12}$, or $NR^{10}R^{11}$,
  (d) aryl,
  (e) het,
  (f) $(C=O)R^9$, or
  (g) $S(O)_mR^9$;
$R^8$ is
  (a) H,
  (b) $C_{1-7}$ alkyl which may be partially unsaturated and optionally substituted by one or more substituents selected from $OR^{12}$, $SR^{12}$, $NR^{10}R^{11}$, or halo,
  (c) $OR^{12}$, or
  (d) $SR^{12}$;
$R^9$ is
  (a) $C_{1-7}$alkyl optionally substituted by $OR^{12}$ or $NR^2R^2$,
  (b) $C_{3-8}$cycloalkyl optionally substituted by $OR^{12}$ or $NR^2R^2$,
  (c) $NR^{10}R^{11}$,
  (d) aryl, or
  (e) het, wherein said het is bound through a carbon atom;
$R^{10}$ and $R^{11}$ are independently
  (a) H,
  (b) aryl,
  (c) $C_{1-7}$alkyl which may be partially unsaturated and is optionally substituted by one or more substituents selected from $CONR^2R^2$, $CO_2R_2$, het, aryl, cyano, or halo,
  (d) $C_{2-7}$alkyl which may be partially unsaturated and is substituted by one or more substituents selected from $NR^2R^2$, $OR^2$, or $SR^2$,
  (e) $C_{3-8}$cycloalkyl which may be partially unsaturated and is optionally substituted by one or more substituents selected from halogen, $OR^2$, $SR^2$, or $NR^2R^2$, or
  (f) $R^{10}$ and $R^{11}$ together with the nitrogen to which they are attached form a het;
$R^{12}$ is
  (a) H,
  (b) aryl,
  (c) het
  (d) $C_{1-7}$alkyl optionally substituted by aryl, or halogen,
  (e) $C_{2-7}$alkyl substituted by $OR^2$, $SR^2$, or $NR^2R^2$, or
  (f) $C_{3-8}$cycloalkyl which may be partially unsaturated and is optionally substituted by one or more substituents selected from halogen, $OR^2$, $SR^2$, or $NR^2R^2$;
$R^{13}$, $R^{14}$, $R^{15}$, and $R^{16}$ are independently
  (a) H
  (b) $C_{1-7}$alkyl which may be partially unsaturated and optionally substituted by one or more $OR^{12}$, $SR^{12}$, $NR^{10}R^{11}$, or halo groups,
  (c) $C_{3-8}$cycloalkyl which may be partially unsaturated and is optionally substituted by one or more substituents selected from halogen, $OR^{12}$, $SR^{12}$, or $NR^{10}R^{11}$,
  (d) aryl,
  (e) het, wherein said het is bound through a carbon atom,
  (f) $OR^{12}$,
  (g) $SR^{12}$,
  (h) $NR^{10}R^{11}$;
  (i) $(C=O)OR^2$, or
  (j) $R^{13}$ and $R^{14}$ or $R^{15}$ and $R^{16}$ together with the carbon to which they are attached form $(C=O)$;
each m is independently 0, 1 or 2;
each n is independently 1 or 3;
aryl is a phenyl radical or an ortho-fused bicyclic carbocyclic radical wherein at least one ring is aromatic, and aryl may be optionally substituted with one or more substituents selected from halo, OH, cyano, $NR^2R^2$, $CO_2R^2$, $CF_3$, $C_{1-6}$alkoxy, and $C_{1-6}$ alkyl which maybe further substituted by one to three $SR^2$, $NR^2R^2$, $OR^2$, or $CO_2R^2$ groups;
het is a four- (4), five- (5), six- (6), or seven- (7) membered saturated or unsaturated heterocyclic ring having 1, 2, or 3 heteroatoms selected from oxygen, sulfur, or nitrogen, which is optionally fused to a benzene ring, or any bicyclic heterocycle group, and het may be optionally substituted with one or more substituents selected from halo, OH, cyano, phenyl, $CO_2R^2$, $CF_3$, $C_{1-6}$alkoxy, oxo, oxime, and $C_{1-6}$ alkyl which may be further substituted by one to three $SR^2$, $NR^2R^2$, $OR^2$, or $CO_2R^2$ groups;
halo or halogen is F, Cl, Br, I;
1 represents the point of attachment between W and G;
2 represents the point of attachment between W and the carbonyl group of Formula (I).

2. A compound of claim 1 wherein W1 is of the formula W1.1

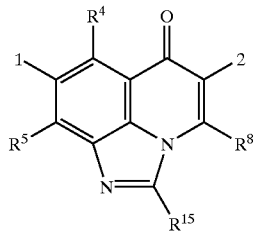
W1.1.

3. A compound of claim 1 wherein W1 is of the formula W1.3

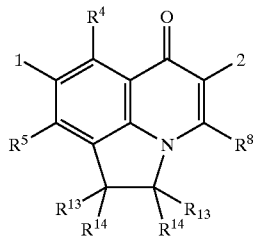
W1.3.

4. A compound of claim 1 wherein W1 is of the formula W1.5

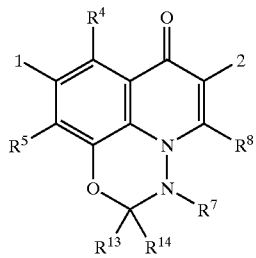
W1.5.

5. A compound of claim 1 wherein W1 is of the formula W1.6

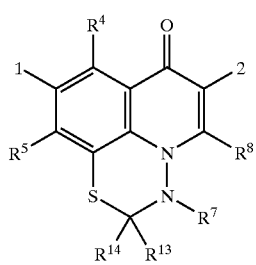
W1.6.

6. A compound of claim 1 wherein W1 is of the formula W1.7

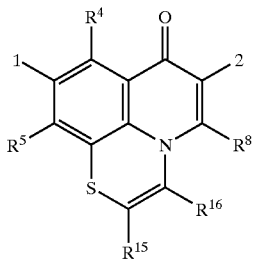
W1.7.

7. A compound of claim 1 wherein W1 is of the formula W1.8

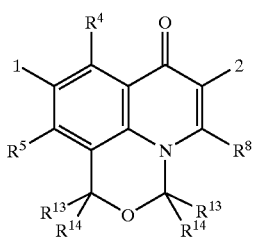
W1.8.

8. A compound of claim 1 wherein W1 is of the formula W1.9

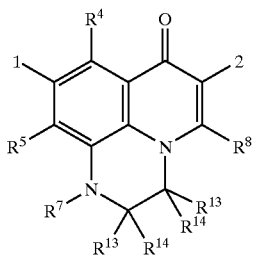
W1.9.

9. A compound of claim 1 wherein W1 is of the formula W1.10

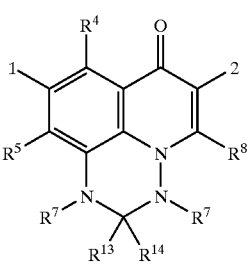
W1.10.

10. A compound of claim 1 wherein W1 is of the formula W1.11

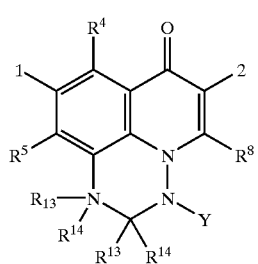

W1.11.

11. A compound of claim 1 wherein W1 is of the formula W1.14

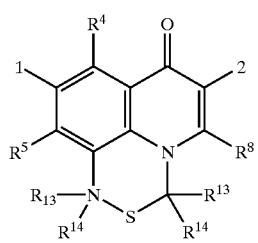

W1.14.

12. A compound of claim 1 wherein W1 is of the formula W1.15

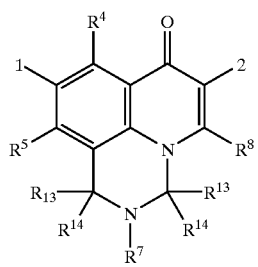

W1.15.

13. A compound of claim 1 wherein W1 is of the formula W1.17

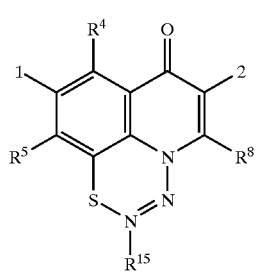

W1.17.

14. A compound of claim 1 wherein W1 is of the formula W1.18

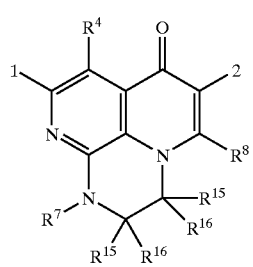

W1.18.

15. A compound of claim 1 wherein W1 is of the formula W1.19

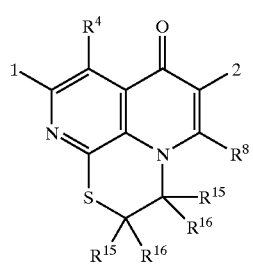

W1.19.

16. A compound of claim 1 wherein W1 is of the formula W1.20

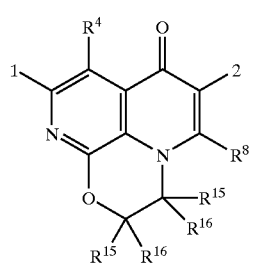

W1.20.

17. A compound of claim 1 wherein W is of the formula W1.23

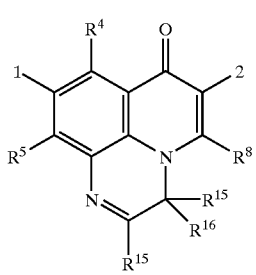

W1.23.

18. A compound of claim 1 wherein W is of the formula W1.24

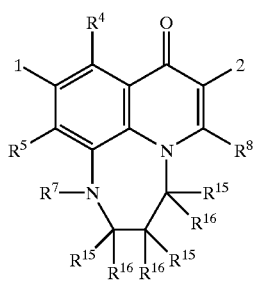
W1.24.

19. A compound of claim 1 wherein W is of the formula W1.25

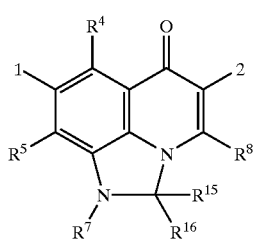
W1.25.

20. A compound of claim 1 wherein W is of the formula W1.26

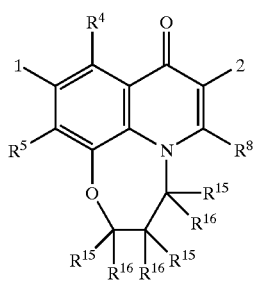
W1.26.

21. A compound of claim 1 wherein W is of the formula W1.52

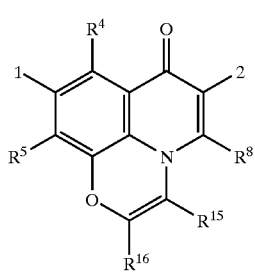
W1.52.

22. A compound according to claim 1 wherein X is Cl.
23. A compound according to claim 1 wherein G is 4-morpholinylmethyl.
24. A compound according to claim 1 wherein G is 3-hydroxypropyl.
25. A compound according to claim 1 wherein G is 3-hydroxy-1-propynyl.
26. A compound according to claim 1 wherein G is tetrahydro-2H-pyran-4-ymethyl.
27. A compound of claim 1 wherein $R^8$ hydrogen.
28. A compound of claim 27 where A is $CR^4$ and B is $CR^5$.
29. A compound 28 where $R^4$ is hydrogen and $R^5$ is hydrogen.
30. A compound of formula I according to claim 1 wherein W is selected from W1.2, W1.4, W1.12, W1.13, W1.16, W1.21, W1.22, W1.27, W1.30, W1.31, W1.32, W1.33, W1.34, W1.35, W1.36, W1.37, W1.38, W1.39, W1.40, W1.41, W1.42, W1.43, W1.44, W1.45, W1.46, W1.47, W1.48, W1.49, W1.50, W1.51, W1.52, W1.53, W1.54, W1.55, W1.56, W1.57, W1.58, W1.59, W1.60, W1.61, W1.62, W1.63, W1.64, or W1.65

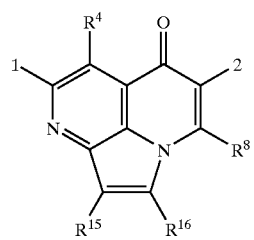
W1.2

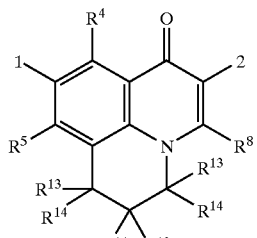
W1.4

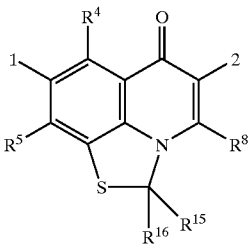
W1.12

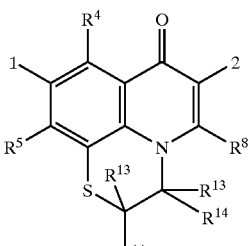
W1.13

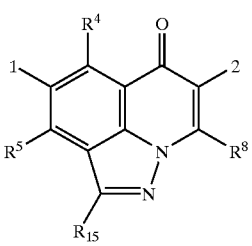
W1.16

-continued
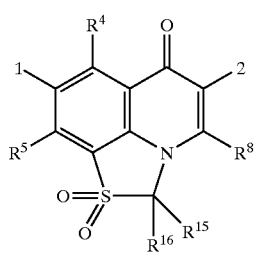
W1.21
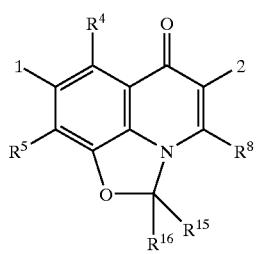
W1.22
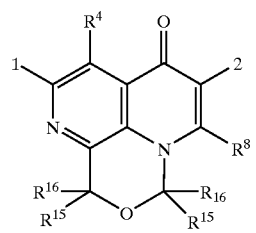
W1.27
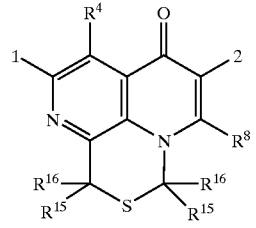
W1.28
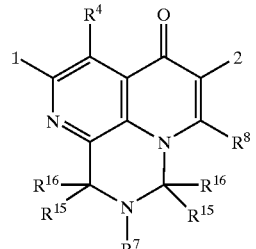
W1.29
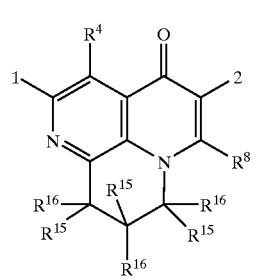
W1.30
-continued
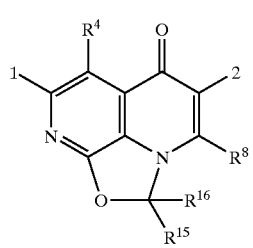
W1.31
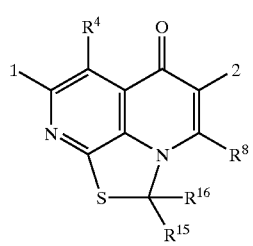
W1.32
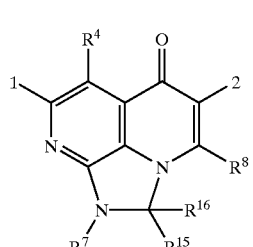
W1.33
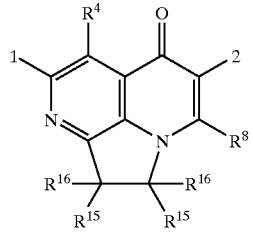
W1.34
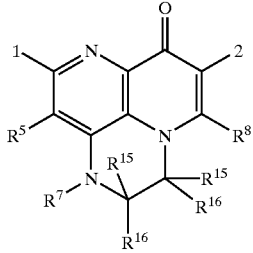
W1.35
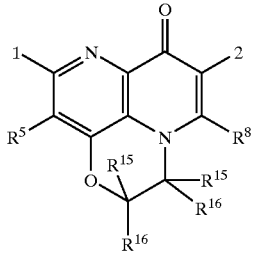
W1.36

-continued
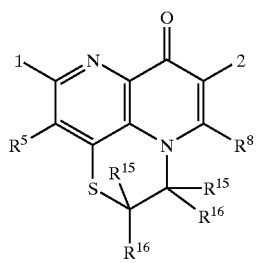
W1.37
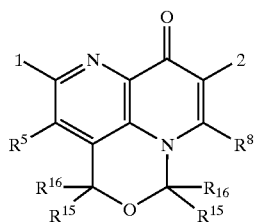
W1.38
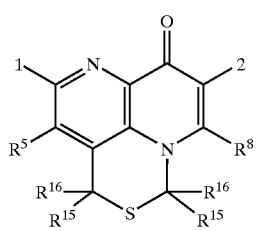
W1.39
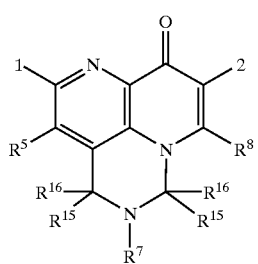
W1.40
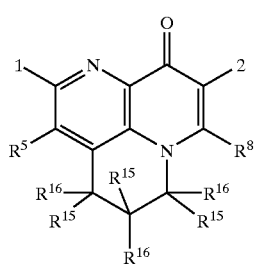
W1.41
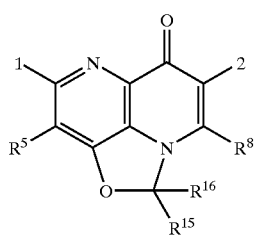
W1.42
-continued
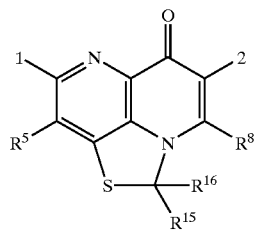
W1.43
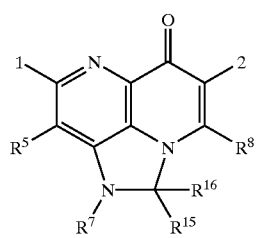
W1.44
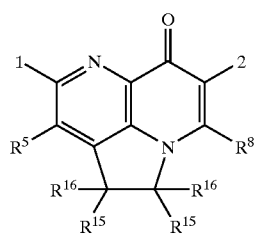
W1.45
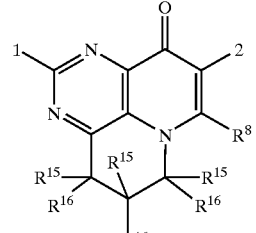
W1.46
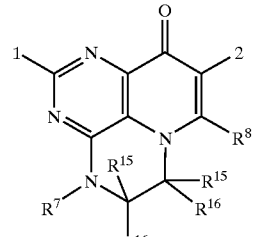
W1.47
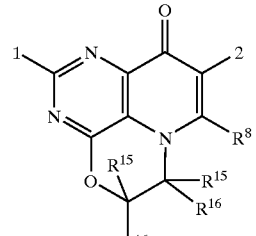
W1.48

W1.49
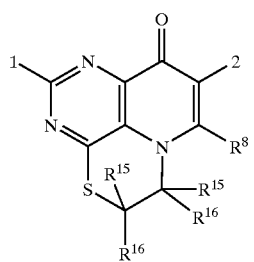
W1.50
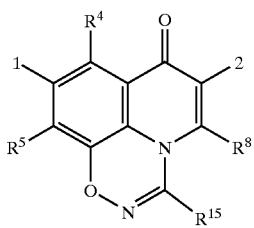
W1.51
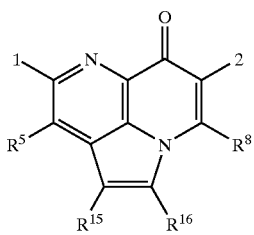
W1.52
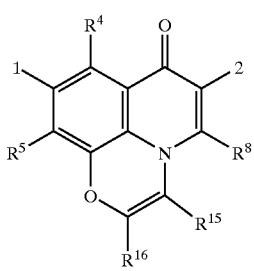
W1.53
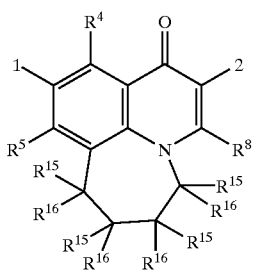
W1.54
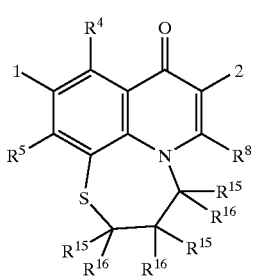
W1.55
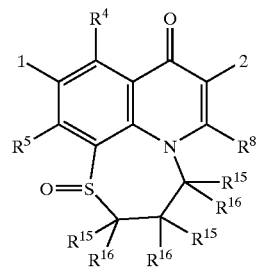
W1.56
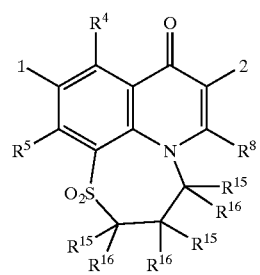
W1.57
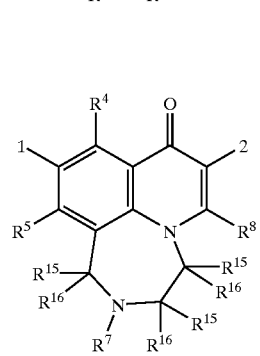
W1.58
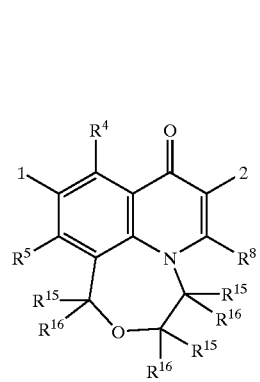
W1.59
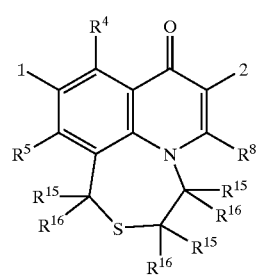

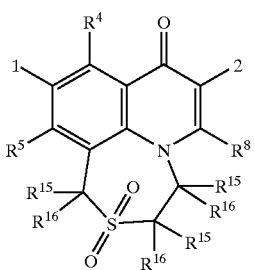

W1.60

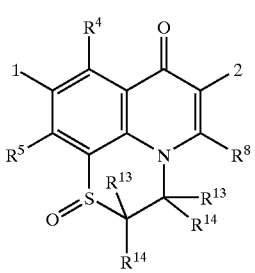

W1.61

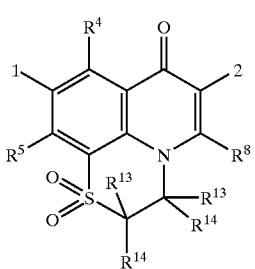

W1.62

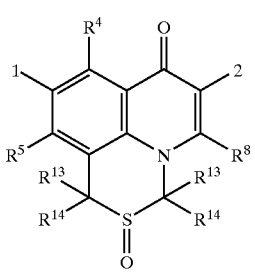

W1.63

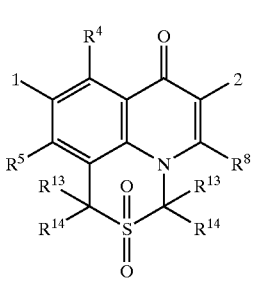

W1.64

OR

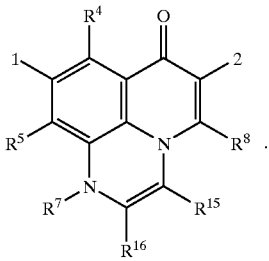

W1.65

31. A compound according to claim 1 which is
N-(4-chlorobenzyl)-8-(4-morpholinylmethyl)-6-oxo-6H-imidazo[4,5,1-ij]quinoline-5-carboxamide;
N-(4-chlorobenzyl)-8-(3-hydroxy-1-propynyl)-6-oxo-6H-imidazo[4,5,1-ij]quinoline-5-carboxamide;
N-(4-chlorobenzyl)-8-(3-hydroxypropyl)-6-oxo-6H-imidazol[4,5,1-ij]quinoline-5-carboxamide;
1-amino-N-(4-chlorobenzyl)-8-(3-hydroxy-1-propynyl)-6-oxo-1,2-dihydro-6H-pyrrolo[3,2,1-ij]quinoline-5-carboxamide;
1-amino-N-(4-chlorobenzyl)-8-(3-hydroxypropyl)-6-oxo-1,2-dihydro-6H-pyrrolo[3,2,1-ij]quinoline-5-carboxamide;
1-amino-N-(4-chlorobenzyl)-8-(4-morpholinylmethyl)-6-oxo-1,2-dihydro-6H-pyrrolo[3,2,1-ij]quinoline-5-carboxamide;
N-(4-chlorobenzyl)-2-(hydroxymethyl)-8-(3-hydroxy-1-propynyl)-6-oxo-1,2-dihydro-6H-pyrrolo[3,2,1-ij]quinoline-5-carboxamide;
N-(4-chlorobenzyl)-8-(3-hydroxyprop-1-ynyl)-2,2-dimethyl-6-oxo-1,2-dihydro-6H-pyrrolo[3,2,1-ij]quinoline-5-carboxamide;
3-benzyl-N-(4-chlorobenzyl)-9-(3-hydroxy-1-propynyl)-7-oxo-2,3-dihydro-7H-[1,3,4]oxadiazino[6,5,4-ij]quinoline-6-carboxamide;
3-benzyl-N-(4-chlorobenzyl)-9-(3-hydroxypropyl)-7-oxo-2,3-dihydro-7H-[1,3,4]-oxadiazino[6,5,4-ij]quinoline-6-carboxamide;
3-benzyl-N-(4-chlorobenzyl)-9-(4-morpholinylmethyl)-7-oxo-2,3-dihydro-7H-[1,3,4]oxadiazino[6,5,4-ij]quinoline-6-carboxamide;
3-benzyl-N-(4-chlorobenzyl)-9-(tetrahydro-2H-pyran-4-ylmethyl)-7-oxo-2,3-dihydro-7H-[1,3,4]oxadiazino[6,5,4-ij]quinoline-6-carboxamide;
N-(4-chlorobenzyl)-9-(3-hydroxyprop-1-ynyl)-3-methyl-7-oxo-2,3-dihydro-7H-[1,3,4]oxadiazino[6,5,4-ij]quinoline-6-carboxamide;
3-benzyl-N-(4-chlorobenzyl)-9-(3-hydroxy-1-propynyl)-7-oxo-2,3-dihydro-7H-[1,3,4]thiadiazino[6,5,4-ij]quinoline-6-carboxamide;
3-benzyl-N-(4-chlorobenzyl)-9-(3-hydroxypropyl)-7-oxo-2,3-dihydro-7H-[1,3,4]-thiadiazino[6,5,4-ij]quinoline-6-carboxamide;
3-benzyl-N-(4-chlorobenzyl)-9-(4-morpholinylmethyl)-7-oxo-2,3-dihydro-7H-[1,3,4]thiadiazino[6,5,4-ij]quinoline-6-carboxamide;
3-benzyl-N-(4-chlorobenzyl)-9-(tetrahydro-2H-pyran-4-ylmethyl)-7-oxo-2,3-dihydro-7H-[1,3,4]thiadiazino[6,5,4-ij]quinoline-6-carboxamide;
N-(4-chlorobenzyl)-3-methyl-9-(morpholin-4-ylmethyl)-7-oxo-7H-[1,4]thiazino[2,3,4-ij]quinoline-6-carboxamide;

N-(4-chlorobenzyl)-3-methyl-7-oxo-9-(tetrahydro-2H-pyran-4-ylmethyl)-7H-[1,4]thiazino[2,3,4-ij]quinoline-6-carboxamide;

N-(4-chlorobenzyl)-9-(3-hydroxypropyl)-3-methyl-7-oxo-7H-[1,4]thiazino[2,3,4-ij]quinoline-6-carboxamide;

N-(4-chlorobenzyl)-9-(3-hydroxyprop-1-ynyl)-3-methyl-7-oxo-7H-[1,4]thiazino[2,3,4-ij]quinoline-6-carboxamide;

N-(4-chlorobenzyl)-9-(morpholin-4-ylmethyl)-7-oxo-2-pyridin-3-yl-7H-[1,4]thiazino[2,3,4-ij]quinoline-6-carboxamide;

N-(4-chlorobenzyl)-9-(3-hydroxy-1-propynyl)-7-oxo-3-phenyl-1H,7H-[1,3]oxazino[5,4,3-ij]quinoline-6-carboxamide;

N-(4-chlorobenzyl)-9-(3-hydroxypropyl)-7-oxo-3-phenyl-1H,7H-[1,3]oxazino[5,4,3-ij]quinoline-6-carboxamide;

N-(4-chlorobenzyl)-7-oxo-3-phenyl-9-(tetrahydro-2H-pyran-4-ylmethyl)-1H,7H-[1,3]oxazino[5,4,3-ij]quinoline-6-carboxamide;

N-(4-chlorobenzyl)-9-(4-morpholinylmethyl)-7-oxo-3-phenyl-1H,7H-[1,3]oxazino[5,4,3-ij]quinoline-6-carboxamide;

N-(4-chlorobenzyl)-9-(3-hydroxy-1-propynyl)-1-methyl-7-oxo-3-phenyl-2,3-dihydro-1H,7H-pyrido[1,2,3-de]quinoxaline-6-carboxamide;

N-(4-chlorobenzyl)-9-(3-hydroxypropyl)-1-methyl-7-oxo-3-phenyl-2,3-dihydro-1H,7H-pyrido[1,2,3-de]quinoxaline-6-carboxamide;

N-(4-chlorobenzyl)-9-(tetrahydro-2H-pyran-4-ylmethyl)-1-methyl-7-oxo-3-phenyl-2,3-dihydro-1H,7H-pyrido[1,2,3-de]quinoxaline-6-carboxamide;

N-(4-chlorobenzyl)-9-(4-morpholinylmethyl)-1-methyl-7-oxo-3-phenyl-2,3-dihydro-1H,7H-pyrido[1,2,3-de]quinoxaline-6-carboxamide;

N-(4-chlorobenzyl)-9-(3-hydroxy-1-propynyl)-2,3,7-trioxo-2,3-dihydro-1H,7H-pyrido[1,2,3-de]quinoxaline-6-carboxamide;

N-(4-chlorobenzyl)-9-(3-hydroxypropyl)-2,3,7-trioxo-2,3-dihydro-1H,7H-pyrido[1,2,3-de]quinoxaline-6-carboxamide;

N-(4-chlorobenzyl)-9-(4-morpholinylmethyl)-2,3,7-trioxo-2,3-dihydro-1H,7H-pyrido[1,2,3-de]quinoxaline-6-carboxamide;

N-(4-chlorobenzyl)-9-(3-hydroxy-1-propynyl)-2,7-dioxo-2,3-dihydro-1H,7H-pyrido[1,2,3-de]quinoxahne-6-carboxamide;

N-(4-chlorobenzyl)-9-(3-hydroxypropyl)-2,7-dioxo-2,3-dihydro-1H,7H-pyrido[1,2,3-de]quinoxaline-6-carboxamide;

N-(4-chlorobenzyl)-9-(3-hydroxy-1-propynyl)-3,7-dioxo-2,3-dihydro-1H,7H-pyrido[1,2,3-de]quinoxaline-6-carboxamide;

N-(4-chlorobenzyl)-9-(3-hydroxypropyl)-3,7-dioxo-2,3-dihydro-1H,7H-pyrido[1,2,3-de]quinoxaline-6-carboxamide;

N-(4-chlorobenzyl)-9-(4-morpholinylmethyl)-3,7-dioxo-2,3-dihydro-1H,7H-pyrido[1,2,3-de]quinoxaline-6-carboxamide;

N-(4-chlorobenzyl)-9-(4-morpholinylmethyl)-2,7-dioxo-2,3-dihydro-1H,7H-pyrido[1,2,3-de]quinoxaline-6-carboxamide;

N-(4-chlorobenzyl)-9-(3-hydroxy-1-propynyl)-1-methyl-2,7-dioxo-2,3-dihydro-1H,7H-pyrido[1,2,3-de]quinoxaline-6-carboxamide;

3-benzyl-N-(4-chlorobenzyl)-9-(3-hydroxy-1-propynyl)-1-methyl-7-oxo-2,3-dihydro-1H,7H-[1,2,4]triazino[5,6,1-ij]quinoline-6-carboxamide;

3-benzyl-N-(4-chlorobenzyl)-9-(3-hydroxypropyl)-1-methyl-7-oxo-2,3-dihydro-1H,7H-[1,2,4]triazino[5,6,1-ij]quinoline-6-carboxamide;

3-benzyl-N-(4-chlorobenzyl)-9-(4-morpholinylmethyl)-1-methyl-7-oxo-2,3-dihydro-1H,7H-[1,2,4]triazino[5,6,1-ij]quinoline-6-carboxamide;

3-benzyl-N-(4-chlorobenzyl)-9-(tetrahydro-2H-pyran-4-ylmethyl)-1-methyl-7-oxo-2,3-dihydro-1H,7H-[1,2,4]triazino[5,6,1-ij]quinoline-6-carboxamide;

1-benzyl-N-(4-chlorobenzyl)-5-(3-hydroxy-1-propynyl)-2,7-dioxo-2,3-dihydro-1H,7H-pyrido[3,2,1-ij]cinnoline-8-carboxamide;

1-benzyl-N-(4-chlorobenzyl)-5-(3-hydroxypropyl)-2,7-dioxo-2,3-dihydro-1H,7H-pyrido[3,2,1-ij]cinnoline-8-carboxamide;

1-benzyl-N-(4-chlorobenzyl)-5-(4-morpholinylmethyl)-2,7-dioxo-2,3-dihydro-1H,7H-pyrido[3,2,1-ij]cinnoline-8-carboxamide;

1-benzyl-N-(4-chlorobenzyl)-5-(tetrahydro-2H-pyran-4-ylmethyl)-2,7-dioxo-2,3-dihydro-1H,7H-pyrido[3,2,1-ij]cinnoline-8-carboxamide;

N-(4-Chlorobenzyl)-5-(3-hydroxyprop-1-ynyl)-1-methyl-7-oxo-2,3-dihydro-1H,7H-pyrido[3,2,1-ij]cinnoline-8-carboxamide;

N-(4-chlorobenzyl)-9-(3-hydroxy-1-propynyl)-7-oxo-3-phenyl-1H,7H-[1,3]thiazino[5,4,3-ij]quinoline-6-carboxamide;

N-(4-chlorobenzyl)-9-(3-hydroxypropyl)-7-oxo-3-phenyl-1H,7H-[1,3]thiazino[5,4,3-ij]quinoline-6-carboxamide;

N-(4-chlorobenzyl)-9-(tetrahydro-2H-pyran-4-ylmethyl)-7-oxo-3-phenyl-1H,7H-[1,3]thiazino[5,4,3-ij]quinoline-6-carboxamide;

N-(4-chlorobenzyl)-9-(4-morpholinylmethyl)-7-oxo-3-phenyl-1H,7H-[1,3]thiazino[5,4,3-ij]quinoline-6-carboxamide;

N-(4-chlorobenzyl)-9-(3-hydroxypropyl)-2-methyl-7-oxo-3-phenyl-2,3-dihydro-1H,7H-pyrido[3,2,1-ij]quinazoline-6-carboxamide;

N-(4-chlorobenzyl)-9-(3-hydroxy-1-propynyl)-2-methyl-7-oxo-3-phenyl-2,3-dihydro-1H,7H-pyrido[3,2,1-ij]quinazoline-6-carboxamide;

N-(4-chlorobenzyl)-9-(4-morpholinylmethyl)-2-methyl-7-oxo-3-phenyl-2,3-dihydro-1H,7H-pyrido[3,2,1-ij]quinazoline-6-carboxamide;

N-(4-chlorobenzyl)-9-(tetrahydro-2H-pyran-4-ylmethyl)-2-methyl-7-oxo-3-phenyl-2,3-dihydro-1H,7H-pyrido[3,2,1-ij]quinazoline-6-carboxamide;

2-benzyl-N-(4-chlorobenzyl)-9-(4-morpholinylmethyl)-7-oxo-2,3-dihydro-1H,7H-pyrido[3,2,1-ij]quinazoline-6-carboxamide;

2-benzyl-N-(4-chlorobenzyl)-9-(4-morpholinylmethyl)-3,7-dioxo-2,3-dihydro-1H,7H-pyrido[3,2,1-ij]quinazoline-6-carboxamide;

N-(4-chlorobenzyl)-9-(3-hydroxy-1-propynyl)-2-(4-morpholinyl)-7-oxo-7H-[1,3,4]-thiadiazino[6,5,4-ij]quinoline-6-carboxamide, N-(4-chlorobenzyl)-9-(3-hydroxypropyl)-2-(4-morpholinyl)-7-oxo-7H-[1,3,4]thiadiazino[6,5,4-ij]quinoline-6-carboxamide;

N-(4-chlorobenzyl)-2-(4-morpholinyl)-9-(4-morpholinylmethyl)-7-oxo-7H-[1,3,4]-thiadiazino[6,5,4-ij]quinoline-6-carboxamide;

N-(4-chlorobenzyl)-2-(4-morpholinyl)-7-oxo-9-(tetrahydro-2H-pyran-4-ylmethyl)-7H-[1,3,4]thiadiazino[6,5,4-ij]quinoline-6-carboxamide;

N-(4-chlorobenzyl)-9-(3-hydroxypropyl)-7-oxo-2,3-dihydro-1H,7H-pyrazino[3,2,1-ij][1,7]naphthyridine-6-carbaxmide;

N-(4-chlorobenzyl)-9-(4-morpholinylmethyl)-7-oxo-2,3-dihydro-1H,7H-pyrazino[3,2,1-ij][1,7]naphthyridine-6-carboxamide;

N-(4-chlorobenzyl)-9-(3-hydroxy-1-propynyl)-7-oxo-2,3-dihydro-1H,7H-pyrazino[3,2,1-ij][1,7]naphthyridine-6-carboxamide;

N-(4-chlorobenzyl)-9-(3-hydroxypropyl)-7-oxo-2,3-dihydro-7H-[1,4]thiazino[2,3,4-ij][1,7]naphthyridine-6-carboxamide;

N-(4-chlorobenzyl)-9-(4-morpholinylmethyl)-7-oxo-2,3-dihydro-7H-[1,4]thiazino[2,3,4-ij][1,7]naphthyridine-6-carboxamide;

N-(4-chlorobenzyl)-9-(3-hydroxy-1-propynyl)-7-oxo-2,3-dihydro-7H-[1,4]thiazino[2,3,4-ij][1,7]naphthyridine-6-carboxamide;

N-(4-chlorobenzyl)-9-(3-hydroxy-1-propynyl)-7-oxo-2,3-dihydro-7H-[1,4]oxazino[2,3,4-ij][1,7]naphthyridine-6-carboxamide; N-(4-chlorobenzyl)-9-(4-morpholinylmethyl)-7-oxo-2,3-dihydro-7H-[1,4]oxazino[2,3,4-ij][1,7]naphthyridine-6-carboxamide;

N-(4-chlorobenzyl)-9-(3-hydroxypropyl)-7-oxo-2,3-dihydro-7H-[1,4]oxazino[2,3,4-ij][1,7]naphthyridine-6-carboxamide;

N-(4-chlorobenzyl)-9-(3-hydroxypropyl)-3,7-dioxo-3H,7H-pyrido[1,2,3-de]quinoxaline-6-carboxamide;

N-(4-chlorobenzyl)-9-(3-hydroxy-1-propynyl)-3,7-dioxo-3H,7H-pyrido[1,2,3-de]quinoxaline-6-carboxamide;

N-(4-chlorobenzyl)-9-(4-morpholinylmethyl)-3,7-dioxo-3H,7H-pyrido[1,2,3-de]quinoxaline-6-carboxamide;

N-(4-chlorobenzyl)-2-[(4-chlorobenzyl)amino]-9-(4-morpholinylmethyl)-7-oxo-3H,7H-pyrido[1,2,3-de]quinoxaline-6-carboxamide;

2-(benzylamino)-N-(4-chlorobenzyl)-9-(4-morpholinylmethyl)-7-oxo-3H,7H-pyrido[1,2,3-de]quinoxaline-6-carboxamide;

N-(4-chlorobenzyl)-10-(3-hydroxypropyl)-2,4,8-trioxo-1,2,3,4-tetrahydro-8H-[1,4]-diazepino [3,2,1-ij]quinoline-7-carboxamide;

N-(4-chlorobenzyl)-10-(3-hydroxy-1-propynyl)-2,4,8-trioxo-1,2,3,4-tetrahydro-8H-[1,4]diazepino[3,2,1-ij]quinoline-7-carboxamide;

N-(4-chlorobenzyl)-10-(4-morpholinylmethyl)-2,4,8-trioxo-1,2,3,4-tetrahydro-8H-[1,4]diazepino[3,2,1-ij]quinoline-7-carboxamide;

N-(4-chlorobenzyl)-10-(4-morpholinylmethyl)-2,8-dioxo-1,2,3,4-tetrahydro-8H-[1,4]diazepino[3,2,1-ij]quinoline-7-carboxamide;

N-(4-chlorobenzyl)-8-(4-morpholinylmethyl)-2,6-dioxo-1,2-dihydro-6H-imidazo[4,5,1-ij]quinoline-5-carboxamide;

N-(4-chlorobenzyl)-8-(3-hydroxy-1-propynyl)-2,6-dioxo-1,2-dihydro-6H-imidazo[4,5,1-ij]quinoline-5-carboxamide;

N-(4-chlorobenzyl)-8-(3-hydroxypropyl)-2,6-dioxo-1,2-dihydro-6H-imidazo[4,5,1-ij]quinoline-5-carboxamide;

N-(4-chlorobenzyl)-8-(4-morpholinylmethyl)-2,6-dioxo-1-[2-(1-piperidinyl)ethyl]-1,2-dihydro-6H-imidazo[4,5,1-ij]quinoline-5-carboxamide;

N-(4-chlorobenzyl)-1-[2-(4-methyl-1-piperazinyl)ethyl]-8-(4-morpholinylmethyl)-2,6-dioxo-1,2-dihydro-6H-imidazo[4,5,1-ij]quinoline-5-carboxamide;

N-(4-chlorobenzyl)-10-(4-morpholinylmethyl)-8-oxo-3,4-dihydro-2H,8H-[1,4]oxazepino[2,3,4-ij]quinoline-7-carboxamide;

N-(4-chlorobenzyl)-3-methyl-9-(morpholin-4-ylmethyl)-7-oxo-7H-[1,4]oxazino[2,3,4-ij]quinoline-6-carboxamide;

N-(4-chlorobenzyl)-3-methyl-7-oxo-9-(tetrahydro-2H-pyran-4-ylmethyl)-7H-[1,4]oxazino[2,3,4-ij]quinoline-6-carboxamide;

N-(4-chlorobenzyl)-9-(3-hydroxypropyl)-3-methyl-7-oxo-7H-[1,4]oxazino[2,3,4-ij]quinoline-6-carboxamide;

N-(4-chlorobenzyl)-9-(3-hydroxyprop-1-ynyl)-3-methyl-7-oxo-7H-[1,4]oxazino[2,3,4-ij]quinoline-6-carboxamide;

N-(4-chlorobenzyl)-9-(morpholin-4-ylmethyl)-7-oxo-2-pyridin-3-yl-7H-[1,4]oxazino[2,3,4-ij]quinoline-6-carboxamide;

2-benzyl-N-(4-chlorobenzyl)-10-(4-morpholinylmethyl)-3,8-dioxo-1,2,3,4-tetrahydro-8H-[1,4]diazepino[6,7,1-ij]quinoline-7-carboxamide; or a pharmaceutically acceptable salt thereof.

32. A compound according to claim 1 which is

N-(4-chlorobenzyl)-10-(4-morpholinylmethyl)-8-oxo3,4-dihydro-2H,8H-[1,4]oxazepino [2,3,4-ij]quinoline-7-carboxamide;

N-(4-chlorobenzyl)-8-(4-morpholinylmethyl)-2,6-dioxo-1,2-dihydro-6H-imidazo[4,5,1-ij]quinoline-5-carboxamide;

N-(4-chlorobenzyl)-9-(4-morpholinylmethyl)-2,7-dioxo-2,3-dihydro-1H,7H-pyrido[1,2,3-de]quinoxaline-6-carboxamide;

N-(4-chlorobenzyl)-2-[(4-chlorobenzyl)amino]-9-(4-morpholinylmethyl)-7-oxo-3H,7H-pyrido[1,2,3-de]quinoxaline-6-carboxamide;

N-(4-chlorobenzyl)-2-(hydroxymethyl)-8-(3-hydroxy-1-propynyl)-6-oxo-1,2-dihydro-6H-pyrrolo[3,2,1-ij]quinoline-5-carboxamide;

N-(4-chlorobenzyl)-8-(3-hydroxyprop-1-ynyl)-2,2-dimethyl-6-oxo-1,2-dihydro-6H-pyrrolo[3,2,1-ij]quinoline-5-carboxamide;

N-(4-chlorobenzyl)-10-(4-morpholinylmethyl)-2,8-dioxo-1,2,3,4-tetrahydro-8H-[1,4]diazepino[3,2,1-ij]quinoline-7-carboxamide;

2-(benzylamino)-N-(4-chlorobenzyl)-9-(4-morpholinylmethyl)-7-oxo-3H,7H-pyrido[1,2,3-de]quinoxaline-6-carboxamide;

N-(4-chlorobenzyl)-9-(3-hydroxy-1-propynyl)-1-methyl-2,7-dioxo-2,3-dihydro-1H,7H-pyrido[1,2,3-de]quinoxaline-6-carboxamide;

2-benzyl-N-(4-chlorobenzyl)-9-(4-morpholinylmethyl)-7-oxo-2,3-dihydro-1H,7H-pyrido[3,2,1-ij]quinazoline-6-carboxamide;

2-benzyl-N-(4-chlorobenzyl)-9-(4-morpholinylmethyl)-3,7-dioxo-2,3-dihydro-1H,7H-pyrido[3,2,1-ij]quinazoline-6-carboxamide;

2-benzyl-N-(4-chlorobenzyl)-10-(4-morpholinylmethyl)-3,8-dioxo-1,2,3,4-tetrahydro-8H-[1,4]diazepino[6,7,1-ij]quinoline-7-carboxamide;

N-(4-chlorobenzyl)-9-(3-hydroxyprop-1-ynyl)-3-methyl-7-oxo-2,3-dihydro-7H-[1,3,4]oxadiazino[6,5,4-ij]quinoline-6-carboxamide;

N-(4-chlorobenzyl)-5-(3-hydroxyprop-1-ynyl)-1-methyl-7-oxo-2,3-dihydro-1H,7H-pyrido[3,2,1-ij]cinnoline-8-carboxamide; or a pharmaceutically acceptable salt thereof.

33. A compound according to claim 1 which is
N-(4-chlorobenzyl)-10-(4-morpholinylmethyl)-8-oxo-3,4-dihydro-2H,8H-[1,4]oxazepino [2,3,4-ij]quinoline-7-carboxamide;

N-(4-chlorobenzyl)-9-(4-morpholinylmethyl)-2,7-dioxo-2,3-dihydro-1H,7H-pyrido[1,2,3-de]quinoxaline-6-carboxamide;

N-(4-chlorobenzyl)-10-(4-morpholinylmethyl)-2,8-dioxo-1,2,3,4-tetrahydro-8H-[1,4]diazepino[3,2,1-ij]quinoline-7-carboxamide;

2-(benzylamino)-N-(4-chlorobenzyl)-9-(4-morpholinylmethyl)-7-oxo-3H,7H-pyrido[1,2,3-de]quinoxaline-6-carboxamide;

N-(4-chlorobenzyl)-9-(3-hydroxy-1-propynyl)-1-methyl-2,7-dioxo-2,3-dihydro-1H,7H-pyrido[1,2,3-de]quinoxaline-6-carboxamide; or a pharmaceutically acceptable salt thereof.

34. A compound according to claim 1 which is N-(4-chlorobenzyl)-9-(4-morpholinylmethyl)-2,7-dioxo-2,3-dihydro-1H,7H-pyrido[1,2,3-de]quinoxaline-6-carboxamide; or a pharmaceutically acceptable salt thereof.

35. A pharmaceutical composition comprising a compound of claim 1 and a pharmaceutically acceptable carrier.

36. A method of treating herpes virus infections comprising administering to a mammal in need of such treatment a compound of claim 1.

37. The method according to claim 36 wherein said mammal is a human.

38. The method according to claim 36 wherein said mammal is a livestock or companion animal.

39. The method according to claim 36 wherein the herpes virus infection is herpes simplex virus type 1 or 2, human herpes virus type, 6, 7, or 8, varicella zoster virus, human cytomegalovirus, or Epstein-Barr virus.

40. The method according to claim 36 wherein the infection is herpes simplex virus type 1 or 2, human herpes virus type 8, varicella zoster virus, human cytomegalovirus, or Epstein-Barr virus.

41. The method according to claim 36 wherein a compound of formula I is administered from about 0.1 to about 300 mg/kg of body weight.

42. The method according to claim 41 wherein a compound of formula I is administered from about 1 to about 30 mg/kg of body weight.

43. The method according to claim 36 wherein the compound is administered parenterally, topically, intravaginally, orally, or rectally.

44. A method for inhibiting a herpes viral DNA polymerase, comprising contacting the polymerase with an effective inhibitory amount of a compound of claim 1.

45. The method of claim 44 wherein the polymerase and the compound are contacted in vitro.

46. The method of claim 44 wherein the polymerase and the compound are contacted in vivo.

* * * * *